(12) United States Patent
Garcia et al.

(10) Patent No.: US 12,091,441 B2
(45) Date of Patent: Sep. 17, 2024

(54) PARTIAL AGONISTS OF INTERLEUKIN-2

(71) Applicant: THE BOARD OF TRUSTEES OF THE LELAND STANFORD JUNIOR UNIVERSITY, Palo Alto, CA (US)

(72) Inventors: Kenan Christopher Garcia, Palo Alto, CA (US); Sonia S. Majri, Palo Alto, CA (US); Caleb R. Glassman, Palo Alto, CA (US); Leon Lih-Ren Su, Mountain View, CA (US)

(73) Assignee: THE BOARD OF TRUSTEES OF THE LELAND STANFORD JUNIOR UNIVERSITY, Palo Alto, CA (US)

(*) Notice: Subject to any disclaimer, the term of this patent is extended or adjusted under 35 U.S.C. 154(b) by 0 days.

(21) Appl. No.: 17/320,174

(22) Filed: May 13, 2021

(65) Prior Publication Data

US 2021/0269498 A1    Sep. 2, 2021

Related U.S. Application Data

(63) Continuation of application No. 16/765,617, filed as application No. PCT/US2018/062122 on Nov. 20, 2018.

(60) Provisional application No. 62/589,497, filed on Nov. 21, 2017.

(51) Int. Cl.
| | |
|---|---|
| *A61K 38/20* | (2006.01) |
| *A61P 37/00* | (2006.01) |
| *C07K 14/55* | (2006.01) |
| *C07K 16/24* | (2006.01) |
| *C12N 15/63* | (2006.01) |
| *A61K 9/00* | (2006.01) |
| *A61K 38/00* | (2006.01) |

(52) U.S. Cl.
CPC .............. *C07K 14/55* (2013.01); *A61P 37/00* (2018.01); *C07K 16/244* (2013.01); *C12N 15/63* (2013.01); *A61K 9/0024* (2013.01); *A61K 38/00* (2013.01); *C07K 2317/74* (2013.01); *C07K 2317/92* (2013.01); *C07K 2319/30* (2013.01); *C07K 2319/31* (2013.01)

(58) Field of Classification Search
CPC ..... C07K 14/55; A61K 38/00; A61K 38/2013
See application file for complete search history.

(56) References Cited

U.S. PATENT DOCUMENTS

| 33,653 A | 11/1861 | Mark et al. |
|---|---|---|
| 4,401,756 A | 8/1983 | Gillis |
| 4,470,461 A | 9/1984 | Stapp |
| 4,518,584 A | 5/1985 | Mark et al. |
| 4,522,811 A | 6/1985 | Eppstein et al. |
| 4,530,787 A | 7/1985 | Shaked et al. |
| 4,569,790 A | 2/1986 | Koths et al. |
| 4,572,798 A | 2/1986 | Koths et al. |
| 4,588,585 A | 5/1986 | Mark et al. |
| 4,604,377 A | 8/1986 | Fernandes et al. |
| 4,656,132 A | 4/1987 | Ben-Bassat et al. |
| 4,738,927 A | 4/1988 | Taniguchi et al. |
| 4,748,234 A | 5/1988 | Dorin et al. |
| 4,752,585 A | 6/1988 | Koths et al. |
| 4,849,329 A | 7/1989 | Leung et al. |
| 4,863,727 A | 9/1989 | Zimmerman et al. |
| 4,879,111 A | 11/1989 | Chong |
| 4,931,543 A | 6/1990 | Halenbeck et al. |
| 4,931,544 A | 6/1990 | Katre et al. |
| 4,938,956 A | 7/1990 | Howard et al. |
| 4,992,271 A | 2/1991 | Hanisch et al. |
| RE33,653 E | 7/1991 | Mark et al. |
| 5,037,644 A | 8/1991 | Shaked et al. |
| 5,078,997 A | 1/1992 | Hora et al. |
| 5,089,261 A | 2/1992 | Nitecki et al. |
| 5,102,872 A | 4/1992 | Singh et al. |
| 5,116,943 A | 5/1992 | Koths et al. |
| 5,122,464 A | 6/1992 | Wilson et al. |
| 5,126,132 A | 6/1992 | Rosenberg |
| 5,206,344 A | 4/1993 | Katre et al. |
| 5,359,046 A | 10/1994 | Capon et al. |
| 5,419,899 A | 5/1995 | Koths et al. |
| 5,442,043 A | 8/1995 | Fukuta et al. |

(Continued)

FOREIGN PATENT DOCUMENTS

| CN | 105980410 A | 9/2016 |
|---|---|---|
| CN | 106659757 A | 5/2017 |

(Continued)

OTHER PUBLICATIONS

Liang et al. Characterization of human interleukin 2 derived from Escherichia coli. Biochem. J., 1985, 229: 429-439.*

(Continued)

*Primary Examiner* — Dong Jiang
(74) *Attorney, Agent, or Firm* — MINTZ, LEVIN, COHN, FERRIS, GLOVSKY AND POPEO, P.C.

(57) ABSTRACT

Provided herein, inter alia, are human interleukin-2 (IL-2) muteins or variants thereof. In particular, provided herein are IL-2 muteins that have a decreased binding capacity for IL-2Rγ. Such IL-2 muteins are useful, for example, as IL-2 partial agonist in applications where reduction or inhibition of one or more IL-2 and/or IL-15 functions is useful (e.g., in the treatment of autoimmune diseases or conditions). Also provided are nucleic acids encoding such IL-2 muteins, methods of making such IL-2 muteins, pharmaceutical compositions that include such IL-2 muteins and methods of treatment using such pharmaceutical compositions.

19 Claims, 23 Drawing Sheets

Specification includes a Sequence Listing.

(56) References Cited

U.S. PATENT DOCUMENTS

| | | |
|---|---|---|
| 5,445,090 A | 8/1995 | Conley, Jr. |
| 5,635,599 A | 6/1997 | Pastan et al. |
| 5,643,565 A | 7/1997 | Doyle et al. |
| 5,696,079 A | 12/1997 | Lane et al. |
| 5,696,234 A | 12/1997 | Zurawski et al. |
| 5,814,314 A | 9/1998 | Lando et al. |
| 5,830,452 A | 11/1998 | Bauer et al. |
| 5,874,076 A | 2/1999 | Lando et al. |
| 5,900,461 A | 5/1999 | Harris |
| 5,932,462 A | 8/1999 | Harris et al. |
| 6,168,785 B1 | 1/2001 | Theze et al. |
| 6,348,192 B1 | 2/2002 | Chan et al. |
| 6,410,008 B1 | 6/2002 | Strom et al. |
| 6,436,386 B1 | 8/2002 | Roberts et al. |
| 6,437,025 B1 | 8/2002 | Harris et al. |
| 6,448,369 B1 | 9/2002 | Bentley et al. |
| 6,451,308 B1 | 9/2002 | Strom et al. |
| 6,468,798 B1 | 10/2002 | Debs et al. |
| 6,495,659 B2 | 12/2002 | Bentley et al. |
| 6,514,491 B1 | 2/2003 | Bentley et al. |
| 6,515,100 B2 | 2/2003 | Harris |
| 6,548,055 B1 | 4/2003 | Lane et al. |
| 6,596,853 B1 | 7/2003 | Theze et al. |
| 6,617,135 B1 | 9/2003 | Gillies et al. |
| 6,689,353 B1 | 2/2004 | Wang et al. |
| 6,825,334 B1 | 11/2004 | Theze et al. |
| 6,927,043 B2 | 8/2005 | Chan et al. |
| 6,929,791 B2 | 8/2005 | Theze et al. |
| 6,955,807 B1 | 10/2005 | Shanafelt et al. |
| 7,091,321 B2 | 8/2006 | Gillies et al. |
| 7,101,965 B2 | 9/2006 | Theze et al. |
| 7,105,653 B2 | 9/2006 | Shanafelt et al. |
| 7,186,804 B2 | 3/2007 | Gillies et al. |
| 7,371,371 B2 | 5/2008 | Epstein et al. |
| 7,462,350 B2 | 12/2008 | Gillies et al. |
| 7,514,073 B2 | 4/2009 | Epstein et al. |
| 7,569,215 B2 | 8/2009 | Wittrup et al. |
| 7,662,368 B2 | 2/2010 | Theze et al. |
| 7,704,490 B2 | 4/2010 | Theze et al. |
| 7,888,071 B2 | 2/2011 | Gillies et al. |
| 7,951,360 B2 | 5/2011 | Wittrup et al. |
| 8,124,066 B2 | 2/2012 | Epstein et al. |
| 8,349,311 B2 | 1/2013 | Wittrup et al. |
| 8,759,486 B2 | 6/2014 | León Monzón et al. |
| 8,906,356 B2 | 12/2014 | Wittrup et al. |
| 9,206,243 B2 | 12/2015 | Len et al. |
| 9,266,938 B2 | 2/2016 | Ast et al. |
| 9,428,567 B2 | 8/2016 | Garcia et al. |
| 9,580,486 B2 | 2/2017 | Gavin et al. |
| 9,616,105 B2 | 4/2017 | Paulsen et al. |
| 9,669,071 B2 | 6/2017 | Klatzmann et al. |
| 9,732,134 B2 | 8/2017 | Gavin et al. |
| 9,844,582 B2 | 12/2017 | Wittrup et al. |
| 9,861,705 B2 | 1/2018 | Bossard et al. |
| 10,010,587 B2 | 7/2018 | Addepalli et al. |
| 10,035,836 B1 | 7/2018 | Greve |
| 10,086,046 B2 | 10/2018 | Paulsen et al. |
| 10,093,711 B2 | 10/2018 | Kannan |
| 10,150,802 B2 | 12/2018 | Garcia et al. |
| 10,166,257 B2 | 1/2019 | Wardell et al. |
| 10,174,091 B1 | 1/2019 | Higginson-scott et al. |
| 10,183,980 B2 | 1/2019 | Garcia et al. |
| 10,293,028 B2 | 5/2019 | Klatzmann et al. |
| 10,654,905 B2 | 5/2020 | Garcia et al. |
| 2002/0041865 A1 | 4/2002 | Austin et al. |
| 2004/0175357 A1 | 9/2004 | Shanafelt et al. |
| 2006/0008872 A1 | 1/2006 | Chung et al. |
| 2006/0199250 A1 | 9/2006 | Zhao et al. |
| 2006/0269515 A1 | 11/2006 | Denis-mize et al. |
| 2006/0292116 A1 | 12/2006 | Epstein et al. |
| 2007/0274948 A1 | 11/2007 | Hurst et al. |
| 2009/0098609 A1 | 4/2009 | Gillies et al. |
| 2010/0028350 A1 | 2/2010 | Jevnikar et al. |
| 2010/0273723 A1 | 10/2010 | Theze et al. |
| 2010/0285014 A1 | 11/2010 | Cox et al. |
| 2011/0091412 A1 | 4/2011 | Wittrup et al. |
| 2011/0091413 A1 | 4/2011 | Epstein et al. |
| 2011/0150826 A1 | 6/2011 | Paulsen et al. |
| 2012/0315245 A1 | 12/2012 | León Monzón et al. |
| 2014/0046026 A1 | 2/2014 | Garcia et al. |
| 2014/0072528 A1 | 3/2014 | Gerdes et al. |
| 2014/0328791 A1* | 11/2014 | Bossard .................. A61P 37/08 424/85.2 |
| 2014/0343252 A1 | 11/2014 | Gavin et al. |
| 2015/0017120 A1 | 1/2015 | Wittrup et al. |
| 2015/0218260 A1 | 8/2015 | Klein et al. |
| 2016/0208017 A1 | 7/2016 | Ast et al. |
| 2016/0229901 A1 | 8/2016 | Merchant |
| 2017/0015722 A1 | 1/2017 | Garcia et al. |
| 2017/0044229 A1 | 2/2017 | Garcia et al. |
| 2017/0137485 A1 | 5/2017 | Gavin et al. |
| 2017/0304402 A1 | 10/2017 | Klatzmann et al. |
| 2017/0313753 A1 | 11/2017 | Gavin et al. |
| 2018/0125941 A1 | 5/2018 | Greve |
| 2018/0142037 A1 | 5/2018 | Ast et al. |
| 2018/0228842 A1 | 8/2018 | Garcia et al. |
| 2018/0237489 A1 | 8/2018 | Kannan |
| 2018/0303754 A1 | 10/2018 | Mariau et al. |
| 2018/0319859 A1 | 11/2018 | Gavin et al. |
| 2018/0326010 A1 | 11/2018 | Codarri Deak et al. |
| 2018/0340014 A1 | 11/2018 | Viney et al. |
| 2019/0022239 A1 | 1/2019 | Hamzah et al. |
| 2019/0023760 A1 | 1/2019 | Bode et al. |
| 2019/0060407 A1 | 2/2019 | Klatzmann et al. |
| 2019/0062395 A1 | 2/2019 | Merchant et al. |
| 2019/0106488 A1 | 4/2019 | Rondon et al. |
| 2019/0202917 A1 | 7/2019 | Campbell et al. |
| 2019/0263877 A1 | 8/2019 | Yeung et al. |
| 2020/0299349 A1 | 9/2020 | Garcia et al. |
| 2021/0079055 A1 | 3/2021 | Garcia et al. |

FOREIGN PATENT DOCUMENTS

| | | |
|---|---|---|
| EP | 267795 A2 | 5/1988 |
| EP | 338841 A1 | 10/1989 |
| EP | 2279753 B1 | 9/2015 |
| EP | 2918285 A1 | 9/2015 |
| JP | 2002515247 A | 5/2002 |
| JP | 2006519170 A | 8/2006 |
| JP | 2007528728 A | 10/2007 |
| JP | 2012046552 A | 3/2012 |
| JP | 2014502967 A | 2/2014 |
| JP | 2014506116 A | 3/2014 |
| JP | 2017518361 A | 7/2017 |
| KR | 1020010043602 A | 5/2001 |
| KR | 1020070003934 A | 1/2007 |
| RU | 2531936 C2 | 10/2014 |
| WO | WO 9947178 A1 | 9/1999 |
| WO | WO 9960128 A1 | 11/1999 |
| WO | 2004060300 A2 | 7/2004 |
| WO | 2005086798 A2 | 9/2005 |
| WO | 2006081510 A2 | 8/2006 |
| WO | 2009061853 A2 | 5/2009 |
| WO | 2012065086 A1 | 5/2012 |
| WO | WO 2012088446 A1 | 6/2012 |
| WO | WO 2013177187 A2 | 11/2013 |
| WO | WO 2014153111 A2 | 9/2014 |
| WO | WO 2014201378 A1 | 12/2014 |
| WO | WO 2015164815 A1 | 10/2015 |
| WO | WO 2016014428 A2 | 1/2016 |
| WO | WO 2016025385 A1 | 2/2016 |
| WO | WO 2017068031 A1 | 4/2017 |
| WO | WO 2017093410 A1 | 6/2017 |
| WO | WO 2017220989 A1 | 12/2017 |
| WO | WO 2019104092 A1 | 5/2019 |
| WO | WO 2020069398 A1 | 4/2020 |
| WO | WO 2021146481 A1 | 7/2021 |
| WO | WO 2021146485 A2 | 7/2021 |

(56) References Cited

OTHER PUBLICATIONS

International Preliminary Report on Patentability issued in International Application No. PCT/US2014/042341, mailed on Dec. 23, 2015, 11 pages.
Zurawski (1991) "Receptor Antagonist and Selective Agonist Derivatives of Mouse Interleukin-2", The EMBO Journal, 11(11):3905-3910.
Alexander Bergmann C. (1991) "The Amphipathicity of Interleukin-2", Electronic Theses & Dissertations centre, 187 pages.
Altschul et al. (1990) "Basic Local Alignment Search Tool", Journal of Molecular Biology, 215(3):403-410.
Argos Patrick (1989) "A Possible Homology between Immunodeficiency Virus P24 Core Protein and Picornaviral VP2 Coat Protein: Prediction of HIV P24 Antigenic Sites", The EMBO Journal, 8(3):779-785.
Baldari et al. (Jan. 1987) "A Novel Leader Peptide Which Allows Efficient Secretion of a Fragment of Human Interleukin 1 beta in *Saccharomyces cerevisiae*", The EMBO Journal, 6(1):229-234.
Baldassari et al. (Oct. 2017) "Daclizumab: Development, Clinical Trials, and Practical Aspects of Use in Multiple Sclerosis", Neurotherapeutics, 14(4):842-858.
Bazan J.F. (Jul. 17, 1992) "Unraveling the Structure of IL-2", Science, 257(5068):410-413.
Berndt et al. (May 31, 1994) "Mutagenic Analysis of a Receptor Contact Site on Interleukin-2: Preparation of an IL-2 Analog with Increased Potency", Biochemistry, 33:6571-6577.
Bielekova et al. (Dec. 14, 2004) "Humanized Anti-CD25 (Daclizumab) Inhibits Disease Activity in Multiple Sclerosis Patients Failing to Respond to Interferon B", Proceedings of the National Academy of Sciences of the United States of America, 101(23):8705-8708.
Blanar et al. (May 15, 1992) "Interaction Cloning: Identification of a Helix-Loop-Helix Zipper Protein that Interacts with C-Fos", Science, 256(5059):1014-1018.
Bluestone et al. (May 19, 2015) "IL-2: Change Structure . . . Change Function", Immunity, 42(5):779-781.
Boder et al. (Jun. 1997) "Yeast Surface Display for Screening Combinatorial Polypeptide Libraries", Nature Biotechnology, 15(6):553-557.
Boozarpour et al. (Jul. 2010) "Bacterial Overexpression of the Human Interleukin-2 in Insoluble form Via the pET Trx Fusion System", Iranian Journal of Biotechnology, 8(3):270-274.
Brandhuber et al. (Sep. 5, 1987) "Crystals and a Low Resolution Structure of Interleukin-2", The Journal of Biological Chemistry, 262(25):12306-12308.
Zurawski et al. (1990) "Partial Agonist/Antagonist Mouse Interleukin-2 Proteins Indicate that a Third Component of the Receptor Complex Functions in Signal Transduction", The EMBO Journal, 9(12):3899-3905.
Bukowski Ronald M. (Oct. 1, 1997) "Natural History and Therapy of Metastatic Renal Cell Carcinoma: The Role of Interleukin-2", Cancer, 80(7):1198-1220.
Busse et al. (Sep. 11, 2008) "Daclizumab Improves Asthma Control in Patients with Moderate to Severe Persistent Asthma: A Randomized, Controlled Trial", American Journal of Respiratory and Critical Care Medicine, 178(10):1002-1008.
Buter Jan (1994) "Clinical studies with biological response modifiers in the treatment of solid tumors", Research Institute Brain and Cognition (B&C), 150 pages.
Carmenate et al. (Jun. 15, 2013) "Human IL-2 Mutein with Higher Antitumor Efficacy than Wild Type IL-2", Journal of Immunology, 190(12):6230-6238.
Carneiro et al. (Apr. 2007) "When Three is not a Crowd: a Crossregulation Model of the Dynamics and Repertoire Selection of Regulatory CD4+ T Cells", Immunological Reviews, 216:48-68.
Carnemolla et al. (2002) "Enhancement of the Antitumor Properties of Interleukin-2 by its Targeted Delivery to the Tumor Blood Vessel Extracellular Matrix", Blood, 99(5):1659-1665.
Cassell et al., (2002) "Therapeutic Enhancement of IL-2 Through Molecular Design", Current Pharmaceutical Design, 8(24):2171-2183.
Cate et al. (Jun. 6, 1986) "Isolation of the Bovine and Human Genes for Müllerian Inhibiting Substance and Expression of the Human Gene in Animal Cells", Cell, 45(5):685-698.
Chang et al., (Jan. 1995) "Structural Analogs of Interleukin-2: A Point Mutation that Facilitates Biological Response", Molecular Pharmacology, 47(1):206-211.
Chang-Cheng, (1998) "Searching for Peptide Ligands of Interleukin-2 Receptor α Chain in Phage-displayed Peptide Library", Chemical Research in Chinese Universities, 14(4):430-432.
Charych et al., (Feb. 1, 2016) "NKTR-214, an Engineered Cytokine with Biased IL2 Receptor Binding, Increased Tumor Exposure, and Marked Efficacy in Mouse Tumor Models", Clinical Cancer Research, 22(3):680-690.
Chen et al., (Sep. 24, 2018) "A Novel Human IL-2 Mutein with Minimal Systemic Toxicity Exerts Greater Antitumor Efficacy than Wild-type IL-2", Cell Death & Disease, 9(989):12 pages.
Collins et al., (Oct. 1, 1988) "Identification of Specific Residues of human interleukin 2 that affect binding to the 70-kDa subunit (p70) of the interleukin 2 receptor", Proceedings of the National Academy of Sciences of the United States of America, 85(20):7709-7713.
Conlon et al., (2018) "Cytokines in the Treatment of Cancer", Journal of Interferon & Cytokine Research, 16 pages.
Database Genbank (Jul. 28, 2020) "Cytokine Receptor Common Subunit Gamma Isoform A Precursor [Mus Musculus]", Genbank Accession No. NP_038591.1, 3 Pages.
Database Genbank (Jul. 25, 2020) "Cytokine Receptor Common Subunit Gamma Precursor [*Homo sapiens*]", Genbank Accession No. NP_000197.1, 3 Pages.
Database Genbank (Jul. 24, 2000) "*Homo sapiens* Interleukin 2 Receptor Subunit Alpha (IL2RA), Transcript Variant 1, Mrna", Genbank Accession No. NM_000417.3, 5 Pages.
Database Genbank (Jul. 23, 2020) "*Homo sapiens* Interleukin 2 Receptor Subunit Beta (IL2RB), Transcript Variant 1, Mrna", Genbank Accession No. NM_000878.5, 5 Pages.
Database Genbank (Jul. 25, 2020) "*Homo sapiens* Interleukin 2 Receptor Subunit Gamma (IL2RG), Mrna", Genbank Accession No. NM_000206.3, 5 Pages.
Database Genbank (Jul. 11, 2020) "Interleukin-2 Precursor [*Homo sapiens*]", Genbank Accession No. NP_000577.2, 3 Pages.
Database Genbank (Jul. 24, 2020) "Interleukin-2 Receptor Subunit Alpha Isoform 1 Precursor [*Homo sapiens*]", Genbank Accession No. NP_000408.1, 3 Pages.
Database Genbank (Jul. 23, 2020) "Interleukin-2 Receptor Subunit Beta Precursor [*Homo sapiens*]", Genhank Accession No. NP_000869.1, 4 Pages.
Database Genbank (Jul. 28, 2020) "Mus Musculus Interleukin 2 Receptor, Gamma Chain (Il2rg), Transcript Variant A, Mrna", Genbank Accession No. NM_013563.4, 4 Pages.
Devereux et al. (Jan. 11, 1984) "A Comprehensive Set of Sequence Analysis Programs for the VAX", Nucleic Acids Research, 12(1):387-395.
Devos et al. (Jul. 11, 1983) "Molecular Cloning of Human Interleukin 2 cDNA and its Expression in *E. coli*", Nucleic Acids Research, 11(13):4307-4323.
Zurawski et al. (Apr. 1988) "Identification of three critical regions within mouse interleukin 2 by fine structural deletion analysis", The EMBO Journal, 7(4):1061-1069.
Dhupkar Pooja (Dec. 2016) "Targeting PD-1/PDL-1 Signaling in the Treatment of Osteosarcoma Lung Metastasis", UT GSBS Dissertations and Theses, 208 pages.
Diab et al. (Aug. 2020) "Bempegaldesleukin (NKTR-214) plus Nivolumab in Patients with Advanced Solid Tumors: Phase I Dose-Escalation Study of Safety, Efficacy, and Immune Activation (PIVOT-02)", 10(8):0F1-0F16.
Drescher et al. (2009) "Surface Plasmon Resonance (SPR) Analysis of Binding Interactions of Proteins in Inner-Ear Sensory Epithelia", Methods in Molecular Biology, 493:323-343(21 pages).
Epstein et al. (May 21, 2003) "Identification of a Protein Fragment of Interleukin 2 Responsible for Vasopermeability", Journal of the National Cancer Institute, 95(10):741-749.
Frick et al. (Oct. 25, 2016) "Interleukin-2 Functionalized Nanocapsules for T Cell-Based Immunotherapy", ACS Nano, 10(10):9216-9226(2 pages).

(56) References Cited

OTHER PUBLICATIONS

Fujita et al. (Dec. 1983) "Structure of The Human Interleukin 2 Gene", Proceedings of the National Academy of Sciences of the United States of America, 80(24):7437-7441.

Fukushima et al. (2001) "Carbohydrate Recognition Mechanism of Interleukin 2 and its Physiological Significance", Experimental Glycoscience, 74(13):2 pages.

Fukushima et al. (Aug. 17, 2001) "Carbohydrate Recognition Site of Interleukin-2 in Relation to Cell Proliferation*", The Journal of Biological Chemistry, 276(33):31202-31208.

Gaffen et al. (Aug. 30, 1996) "Distinct Tyrosine Residues within the Interleukin-2 Receptor Beta Chain Drive Signal Transduction Specificity, Redundancy, and Diversity", Journal of Biological Chemistry, 271(35):21381-21390.

Gai Shuning (2012) "Engineering Persistent Interleukin-2 for Cancer Immunotherapy", Massachusetts Institute of Technology, 113 pages.

Garber Ken (May 9, 2018) "Cytokine Resurrection: Engineered IL-2 Ramps up Immuno-Oncology Responses", Nature Biotechnology, 36(5):378-379.

Georg A. (Oct. 1999) "On the Stochastic Regulation of Interleukin-2 Transcription☆", Seminars in Immunology, 11(5):2 pages.

Gerhartz et al. (May 31, 1996) "Differential Activation of Acute Phase Response Factor/STAT3 and STAT1 via the Cytoplasmic Domain of the Interleukin 6 Signal Transducer gp130. I. Definition of a Novel Phosphotyrosine Motif Mediating STAT1 Activation", Journal of Biological Chemistry, 271(22):12991-12998.

Ghasemi et al. (Sep. 21, 2016) "Selective Targeting of IL-2 To NKG2D Bearing Cells for Improved Immunotherapy", Nature Communications, 7(12878 ):15 pages.

Gillies et al. (Jun. 1, 2011) "A Low-Toxicity IL-2-Based Immunocytokine Retains Antitumor Activity Despite its High Degree of IL-2 Receptor Selectivity", Clinical Cancer Research, 17(11): 3673-3685.

Gold et al. (Apr. 4, 2013) "Daclizumab High-Yield Process in Relapsing-Remitting Multiple Sclerosis (Select): A Randomised, Double-Blind, Placebo-Controlled Trial", Lancet, 381(9884):2167-2175.

Goodson et al. (May 1990) "Site-Directed Pegylation of Recombinant Interleukin-2 at its Glycosylation Site", Biotechnology, 8(4):343-346.

He et al. (Sep. 2016) "Low-Dose Interleukin-2 Treatment Selectively Modulates Cd4(+) T Cell Subsets in Patients with Systemic Lupus Erythematosus", Nature Medicine, 22(9):991-993.

Hershberger et al. (Jun. 30, 2005) "Daclizumab to Prevent Rejection after Cardiac Transplantation", The New England Journal of Medicine, 352(26):2705-2713.

Imler (Jun. 1992) "Identification of Three Adjacent Amino Acids of Interleukin-2 Receptor Beta Chain Which Control the Affinity and the Specificity of the Interaction With Interleukin-2", The EMBO Journal, 11(6):2047-2053.

Jacques et al. (Jun.-Jul. 2016) "The Renewal of Interleukin 2", Medical Sciences Paris, 32(6-7):612-618(9 pages).

Jevsevar et al. (Jan. 2010) "PEGylation of Therapeutic Proteins", Biotechnology Journal, 5(1):113-128.

Jiang et al. (2000) "Interleukin-2: Structural and Biological Relatedness to Opioid Peptides", Neuroimmunomodulation, 8:20-24.

Jones et al. (Jan. 2019) "Designer Protein Delivers Signal of Choice", Nature, 565(7738):165-166.

Ju et al. (Apr. 25, 1987) "Structure-Function Analysis of Human Interleukin-2. Identification of Amino Acid Residues Required for Biological Activity", Journal of Biological Chemistry, 262(12)5723-5731.

Kaartinen et al. (2017) "Low Interleukin-2 Concentration Favors Generation of Early Memoryt Cells over Effector Phenotypes During Chimeric Antigen Receptor T-cell Expansion", Cytotherapy, 19:689-702.

Kagoya et al. (Mar. 2018) "A Novel Chimeric Antigen Receptor Containing a JAK-STAT Signaling Domain Mediates Superior Antitumor Effects", Nature medicine, 24(3):352-359.

Kallal et al. (Jan. 1, 2013) "Changing Partners at the Dance: Variations in STAT Concentrations for Shaping Cytokine Function and Immune Responses to Viral Infections", JAKSTAT, 2(1): e23504 (10 pages).

Kalsoom Saima (2016) "Computer-Guided Design and Synthesis of IL-2 Inhibitors as Immunomodulating Agents", Department of Chemistry, 181 pages.

Katre Nandini V. (Feb. 1990) "Immunogenicity of Recombinant IL-2 Modified by Covalent Attachment of Polyethylene Glycol", The Journal of Immunology, 144(1):209-213.

Kaufman et al. (Nov. 1982) "Construction of a Modular Dihydrofolate Reductase cDNA Gene: Analysis of Signals Utilized for Efficient Expression.", Molecular and Cellular Biology, 2(11):1304-1319.

Kaufman et al. (Jan. 1987) "Translational Efficiency of Polycistronic mRNAs and their Utilization to Express Heterologous Genes in Mammalian Cells", The EMBO Journal, 6(1):187-195.

Kim et al. (Jul. 2001) "The Basis for IL-2-Induced IL-2 Receptor a Chain Gene Regulation: Importance of Two Widely Separated IL-2 Response Elements", Immunity, 15:159-172.

Klingmüller (Aug. 6, 1996) "Multiple Tyrosine Residues in the Cytosolic Domain of the Erythropoietin Receptor Promote Activation of STAT5", Proceedings of the National Academy of Sciences, 93(16):8324-8328.

Krieg et al. (Jun. 29, 2010) "Improved IL-2 Immunotherapy by Selective Stimulation of IL-2 Receptors on Lymphocytes and Endothelial Cells", Proceedings of the National Academy of Sciences, 107(26):11906-11911.

Zurawski et al. (Dec. 15, 2013) "Definition and Spatial Location of Mouse Interleukin-2 Residues That Interact with its Heterotrimeric Receptor", The EMBO Journal, 12(13):5113-5119.

Krinks et al., "KY1043, a Novel PD-L1 IL-2 Immunocytokine Directed Towards CD25, Delivers Potent Anti-tumour Activity in Vitro and in Vivo", Kymab P625, 1 page.

Kurjan et al. (Oct. 1982) "Structure of a Yeast Pheromone Gene (MF Alpha): A Putative Alpha-Factor Precursor Contains Four Tandem Copies of Mature Alpha-Factor", Cell, 30(3):933-943.

Langowski John (Jul. 8-12, 2017) "NKTR-358: a Selective, First-in-Class IL-2 Pathway Agonist which Increases Number and Suppressive Function of Regulatory T Cells for the Treatment of Immune Inflammatory Disorders", 13 World Congress on Inflammation London, 10 pages.

Leclair et al. (Sep. 1992) "The P50 Subunit of NF-Kappa B Associates with the NF-IL6 Transcription Factor", Proceedings of the National Academy of Sciences of the United States of America, 89(17):8145-8149.

Lee et al. (Mar. 5, 1988) "Proliferin Secreted by Cultured Cells Binds to Mannose 6-Phosphate Receptors", Journal of Biological Chemistry, 263(7):3521-3527.

Leon et al. (Jan. 2018) "Combining Computational and Experimental Biology to Develop Therapeutically Valuable IL2 Muteins", Seminars in Oncology, 45(1-2):96-104.

Leon et al. (Dec. 2013) "Mathematical Models of the Impact of 112 Modulation Therapies on T Cell Dynamics", Immunology, 4(439):21 pages.

Levin et al. (2012) "Exploiting a Natural Conformational Switch to Engineer an Interleukin-2 'Superkine'", Nature, 484(7395):529-533.

Lipiainen et al., Feb. 2015, e-Pub(Dec. 9, 2014), "Formulation and Stability of Cytokine Therapeutics", Journal of Pharmaceutical Sciences, 104(2):307-326.

Liu et al. (Aug. 21, 2018) "Dual Targeting of Innate and Adaptive Checkpoints on Tumor Cells Limits Immune Evasion", Cell Reports, 24(8):2101-2111.

Liu et al. (2009) "Engineered Interleukin-2 Antagonists for the Inhibition of Regulatory T cells", Journal of Immunotherapy, 32(9):887-894.

Luckow et al. (May 1, 1989) "High Level Expression of Nonfused Foreign Genes with Autographa Californica Nuclear Polyhedrosis Virus Expression Vectors", Virology, 170(1):31-39.

Mackall et al. (Mar. 2, 2018) "Engineering a Designer Immunotherapy", Science, 359(6379):990-991.

(56) References Cited

OTHER PUBLICATIONS

Malek et al. (Aug. 27, 2010) "Interleukin-2 Receptor Signaling: At the Interface between Tolerance and Immunity", Immunity, 33(2):153-165.
Mao et al. (2018) "Study of the Molecular Mechanism of Interleukin-2 Mutein D10 Binding to IL-2 Receptors by Molecular Simulations", Molecular Simulation, 8 pages.
Marston Fiona A. (1986) "The Purification of Eukaryotic Polypeptides Synthesized in *Escherichia coli*", Biochemical Journal, 240:12 pages.
McCaffrey et al. (Jul. 4, 2002) "RNA Interference in Adult Mice", Nature, 418(6893):38-39.
Meghnem et al. (Jun. 15, 2017) "Cutting Edge: Differential Fine-Tuning of IL-2- and IL-15-Dependent Functions by Targeting Their Common IL-2/15Rβ/γc Receptor", Journal of Immunology, 198(12):4563-4568.
Meyers et al. (Mar. 1991) "A Phase I Study Including Pharmacokinetics of Polyethylene Glycol Conjugated Interleukin-2", Clinical Pharmacology & Therapeutics, 49(3):307-313.
Mitra et al. (May 19, 2015) "Interleukin-2 Activity can be Fine-Tuned with Engineered Receptor Signaling Clamps", Immunity, 42(5):826-838.
Morris et al. (Jan. 10, 2006) "Preclinical and Phase I Clinical Trial of Blockade of IL-15 Using Mikβ1 Monoclonal Antibody in T Cell Large Granular Lymphocyte Leukemia", Proceedings of the National Academy of Sciences of the United States of America, 103(2):401-406.
Naeger et al. (Jan. 22, 1999) "Identification of a STAT4 Binding Site in the Interleukin-12 Receptor Required for Signaling", Journal of Biological Chemistry, 274(4):1875-1878.
Naing et al. (2017) "Immunotherapy", Advances in Experimental Medicine and Biology, 183 pages.
Parisi et al. (2020) "Persistence of Adoptively Transferred T Cells with a Kinetically Engineered IL-2 Receptor Agonist", Nature Communications, 11(660):12 pages.
Perol et al. (2016) "New Molecular and Cellular Mechanisms of Tolerance: Tolerogenic Actions of IL-2", Methods in Molecular Biology, 1371:49 pages.
Peterson et al. (Dec. 2018) "A Long-lived IL-2 Mutein that Selectively Activates and Expands Regulatory T Cells as a Therapy for Autoimmune Disease", Journal of Autoimmunity, 95:1-14.
Plieth (Mar. 2018) "Cytokines Emerge as 2018's Immuno-oncology Stars", Evaluate, 1-7.
Pol et al. (Jan. 6, 2020) "Effects of Interleukin-2 in Immunostimulation and Immunosuppression", Journal of Experimental Medicine, 217(1):15 pages.
Putnam David A. (Jan. 15, 1996) "Antisense Strategies and Therapeutic Applications", American Journal of Health-System Pharmacy, 53(2):151-160.
Rao et al. (Aug. 9, 2005) "High-Affinity cd25-Binding IL-2 Mutants Potently Stimulate Persistent T Cell Growth", Biochemistry, 44(31):10696-10701.
Rao et al. (Oct. 2004) "Interleukin 2 (IL-2) Variants Engineered for Increased IL-2 Receptor Alpha-Subunit Affinity Exhibit Increased Potency Arising from a Cell Surface Ligand Reservoir Effect", Molecular Pharmacology, 66(4): 864-869.
Rao et al. (2003) "Interleukin-2 Mutants with Enhanced α-Receptor Subunit Binding Affnity", Protein Engineering, 16(12):1081-1087.
Rao Balaji M. (Sep. 2004) "Interleukin-2 Engineering for Improved Therapeutic Effectiveness", Massachusetts Institute of Technology, 106 pages.
Ren et al. (2016) "Structural and Functional Characterisation of Ferret Interleukin-2", Developmental and Comparative Immunology, 55:33-38.
Ring et al. (Dec. 2012) "Mechanistic and Structural Insight Into the Functional Dichotomy Between Interleukin-2 and Interleukin-15", Nature Immunology, 13(12):1187-1195.
Rodríguez-Silva (2001) "Scale-up Purification of a Mutant of Recombinant Human Interleukin 2 by Reverse-phase High Performance Liquid Chromatography", Biotecnología Aplicada, 18:159-162.
Rojas et al. (2019) "Directed Evolution of Supersecreted Variants from Phagedisplayed Human Interleukin-2", Scientific Reports, 9(800):13 pages.
Rosalia et al., (Dec. 2014) "Use of Enhanced Interleukin-2 Formulations for Improved Immunotherapy Against Cancer", Current Opinion in Chemical Biology, 23:39-46.
Rosenberg et al. (1987) "Vectors for Selective Expression of Cloned DNAs by T7 RNA Polymerase", Gene, 56(1):125-135.
Rozwarski et al. (Mar. 15, 1994) "Structural Comparisons Among the Short-Chain Helical Cytokines", Structure, 2(3):159-173.
Sambrook et al. (2012) "Molecular Cloning: A Laboratory Manual", 4th Editon, 34 pages.
Scheller et al. (Mar. 2019) "Immunoreceptor Engineering and Synthetic Cytokine Signaling for Therapeutics", Trends in Immunology, 40(3):258-272.
Schmitz et al. (Jan. 15, 2000) "The Cytoplasmic Tyrosine Motifs in Full-Length Glycoprotein 130 Have Different Roles in IL-6 Signal Transduction", The Journal of Immunology, 164(2):848-854.
Schultz et al. (1987) "Expression and Secretion in Yeast of a 400-kda Envelope Glycoprotein Derived from Epstein-Barr Virus", Gene, 54(1):113-123.
Seed B. (Oct. 29, 1987) "An LFA-3 cDNA encodes a phospholipid-linked membrane protein homologous to its receptor CD2", Nature, 329(6142):840-842.
Silva et al. (Jan. 9, 2019) "De Novo Design of Potent and Selective Mimics of IL-2 and IL-15", Nature, 565(7738):186-191.
Sim et al. (Nov. 2016) "IL2 Variant Circumvents ICOS+ Regulatory T-cell Expansion and Promotes NK Cell Activation", Cancer Immunology Research, 4(11):983-994 (13 pages).
Smith et al. (Dec. 1983) "Production of Human Beta Interferon in Insect Cells Infected with a Baculovirus Expression Vector", Molecular and Cellular Biology, 3(12):2156-2165.
Smith A K. (2006) "The Structure of IL2 Bound to the Three Chains of the IL2 Receptor and How Signaling Occurs", Medical Immunology, 5(3):5 pages.
Smith Kendall A. (Mar. 15, 1993) "Lowest Dose Interleukin-2 Immunotherapy", Blood, 81(6):1414-1423.
Zorn et al. (Sep. 1, 2006) "IL-2 Regulates FOXP3 Expression In Human Cd4+Cd25+Regulatory T Cells Through a STAT-dependent Mechanism and Induces the Expansion of these Cells In Vivo", Blood, 108(5):1571-1579.
Sockolosky et al. (Mar. 2, 2018) "Selective targeting of engineered T cells using orthogonal IL-2 cytokine-receptor complexes", Science, 359(6379):1037-1042.
Spangler et al. (May 19, 2015) "Antibodies to Interleukin-2 Elicit Selective T Cell Subset Potentiation through Distinct Conformational Mechanisms", Immunity, 42:815-825.
Spangler et al. (Oct. 1, 2018) "Engineering a Single-Agent Cytokine/Antibody Fusion That Selectively Expands Regulatory T Cells for Autoimmune Disease Therapy", The Journal of Immunology, 201(7):13 pages.
Stauber et al. (Feb. 21, 2006) "Crystal Structure of the IL-2 Signaling Complex: Paradigm for a Heterotrimeric Cytokine Receptor", Proceedings of the National Academy of Sciences, 103(8):2788-2793.
Tchao (2017) "AMG 592 is an Investigational IL-2 Mutein That Induces Highly Selective Expansion of Regulatory T Cells", Blood, 130(Supplement 1):696.
Thanos et al. (2003) "Potent Small-Molecule Binding to a Dynamic Hot Spot on IL-2", Journal of the American Chemical Society, 125(50):2 pages.
Tilley et al. (Aug. 1997) "Identification of a Small Molecule Inhibitor of the IL2/IL2Ra Receptor Interaction Which Binds to IL2", Journal of the American Chemical Society, 119(32):7589-7590.
Tkaczuk et al. (2002) "Effect of Anti-IL-2Ralpha Antibody on IL-2-Induced Jak/STAT Signaling", American Journal of Transplantation, 2(1):31-40.

(56) References Cited

OTHER PUBLICATIONS

Trotta et al. (Jul. 2018) "A Human Anti-IL-2 Antibody that Potentiates Regulatory T Cells by a Structure-based Mechanism", Nature Medicine, 24:1005-1014.
Tsytsikov et al. (Sep. 20, 1996) "Identification and Characterization of Two Alternative Splice Variants of Human Interleukin-2*", The Journal of Biological Chemistry, 271(38):23055-23060.
Vincenti et al. (Jan. 15, 1998) "Interleukin-2-Receptor Blockade with Daclizumab to Prevent Acute Rejection in Renal Transplantation. Daclizumab Triple Therapy Study Group", The New England Journal of Medicine, 338(3):161-165.
Vlasveld et al. (Jul. 1994) "Recombinant Interleukin-2 in Cancer: Basic and Clinical Aspects", Cancer Treatment Reviews, 20(3):275-311.
Wada et al., 1992, "Codon Usage Tabulated from the GenBank Genetic", Nucleic Acids Research, 20:2111-2118.
Waldmann et al. (Jan. 17, 2013) "Phase 1 Trial of IL-15 Trans Presentation Blockade Using Humanized Mik-Beta-1 Mab in Patients with T-Cell Large Granular Lymphocytic Leukemia", Blood, 121(3):476-484.
Waldmann T A. (1989) "The Multi-Subunit Interleukin-2 Receptor", Annual review of biochemistry, 58(1):875-911.
Wang et al. (Apr. 1997) "126Gln is the Residue of Human IL-2 Binding to IL-2R y Subunit", Science in China Series C: Life Sciences, 40(2):159-168.
Wang et al. (Jan. 2008) "Dual Effects of Tween 80 on Protein Stability", International Journal of Pharmaceutics, 347(1-2):31-38.
Wang et al. (Jun. 29, 1984) "Site-Specific Mutagenesis of the Human Interleukin-2 Gene: Structure-function Analysis of the Cysteine Residues", Science, 224(4656):2 pages.
Wang et al. (Nov. 18, 2005) "Structure of the Quaternary Complex of Interleukin-2 With its A, B, and Gc Receptors", American Association for the Advancement of Science, 310(5751):1159-1163.
Wang et al. (1995) "Two Partial Antagonists of Human Interleukin2",Science Abstracts, 2 pages.
Ward et al. (Nov. 1, 2018) "IL-2/CD25: A Long-Acting Fusion Protein That Promotes Immune Tolerance by Selectively Targeting the IL-2 Receptor on Regulatory T Cells", The Journal of Immunology, 201(9):2579-2592.
Wittrup Dane K. (Sep. 2017), "Anti-tumor Antibodies Can Drive Therapeutic T Cell Responses", Trends in Cancer, 3(9):615-620.
Wrangle et al., (Feb. 1, 2018) "IL-2 and Beyond in Cancer Immunotherapy", Journal of Interferon & Cytokine Research, 38(2):45-68.
Xia et al. (Sep. 16, 2002) "siRNA-Mediated Gene Silencing in Vitro and in Vivo", Nature Biotechnology, 20:1006-1010.
Yang et al. (Jan. 8, 2000) "Molecular Modeling on Some Human Interleukins Sharing yc of Interleukin-2 Receptor, and Structure-Function Relationships", Journal of Molecular Structure: Theochem, 532:1-10.
Zalipsky Samuel (Mar. 1995) "Functionalized Poly(ethylene glycols) for Preparation of Biologically Relevant Conjugates", Bioconjugate Chemistry, 6(2):150-165.
Levin, A.M. et al. (Apr. 26, 2012). "Exploiting a natural conformational switch to engineer an interleukin-2 'superkine,'" Nature, vol. 484:529-535.
Partial Supplementary European search report issued in European Application No. 18881013.9, mailed on Sep. 10, 2021, 14 pages.

* cited by examiner

| Name | Sequence | Mutations | SEQ ID |
|---|---|---|---|
| WT IL-2 | APTSSSTKKTQLQLEHLLLDLQMILNGINNYKNPKLTRMLTFKFYMPKKATELKHLQCLEEELKPLEEVLNLAQ SKNFHLRPRDLISNINVIVLELKGSETTFMCEYADETATIVEFLNRWITFCQSIISTLT | | SEQ ID NO:1 |
| H9 IL-2 | APTSSSTKKTQLQLEHLLLDLQMILNGINNYKNPKLTRMLTFKFYMPKKATELKHLQCLEEELKPLEEVLNLAQ SKNFHFDPRDVVSNINVFVLELKGSETTFMCEYADETATIVEFLNRWITFCQSIISTLT | L80F, L18R, R81D, Q22E, L85V, I86V, I92F | SEQ ID NO:2 |
| H9_REA | APTSSSTKKTQLQLEHLLRLDLEMILNGINNYKNPKLTRMLTFKFYMPKKATELKHLQCLEEELKPLEEVLNLAQ SKNFHFDPRDVVSNINVFVLELKGSETTFMCEYADETATIVEFLNRWITFCASIISTLT | L80F, L18R, R81D, Q22E, L85V, I86V, Q126A, I92F | SEQ ID NO:3 |
| H9_REC | APTSSSTKKTQLQLEHLLRLDLEMILNGINNYKNPKLTRMLTFKFYMPKKATELKHLQCLEEELKPLEEVLNLAQ SKNFHFDPRDVVSNINVFVLELKGSETTFMCEYADETATIVEFLNRWITFCCSIISTLT | L80F, L18R, R81D, Q22E, L85V, I86V, Q126C, I92F | SEQ ID NO:4 |
| H9_RED | APTSSSTKKTQLQLEHLLRLDLEMILNGINNYKNPKLTRMLTFKFYMPKKATELKHLQCLEEELKPLEEVLNLAQ SKNFHFDPRDVVSNINVFVLELKGSETTFMCEYADETATIVEFLNRWITFCDSIISTLT | L80F, L18R, R81D, Q22E, L85V, I86V, Q126D, I92F | SEQ ID NO:5 |
| H9_REE | APTSSSTKKTQLQLEHLLRLDLEMILNGINNYKNPKLTRMLTFKFYMPKKATELKHLQCLEEELKPLEEVLNLAQ SKNFHFDPRDVVSNINVFVLELKGSETTFMCEYADETATIVEFLNRWITFCESIISTLT | L80F, L18R, R81D, Q22E, L85V, I86V, Q126E, I92F | SEQ ID NO:6 |
| H9_REG | APTSSSTKKTQLQLEHLLRLDLEMILNGINNYKNPKLTRMLTFKFYMPKKATELKHLQCLEEELKPLEEVLNLAQ SKNFHFDPRDVVSNINVFVLELKGSETTFMCEYADETATIVEFLNRWITFCGSIISTLT | L80F, L18R, R81D, Q22E, L85V, I86V, Q126G, I92F | SEQ ID NO:7 |
| H9_REH | APTSSSTKKTQLQLEHLLRLDLEMILNGINNYKNPKLTRMLTFKFYMPKKATELKHLQCLEEELKPLEEVLNLAQ SKNFHFDPRDVVSNINVFVLELKGSETTFMCEYADETATIVEFLNRWITFCHSIISTLT | L80F, L18R, R81D, Q22E, L85V, I86V, Q126H, I92F | SEQ ID NO:8 |
| H9_REI | APTSSSTKKTQLQLEHLLRLDLEMILNGINNYKNPKLTRMLTFKFYMPKKATELKHLQCLEEELKPLEEVLNLAQ SKNFHFDPRDVVSNINVFVLELKGSETTFMCEYADETATIVEFLNRWITFCISIISTLT | L80F, L18R, R81D, Q22E, L85V, I86V, Q126I, I92F | SEQ ID NO:9 |
| H9_REK | APTSSSTKKTQLQLEHLLRLDLEMILNGINNYKNPKLTRMLTFKFYMPKKATELKHLQCLEEELKPLEEVLNLAQ SKNFHFDPRDVVSNINVFVLELKGSETTFMCEYADETATIVEFLNRWITFCKSIISTLT | L80F, L18R, R81D, Q22E, L85V, I86V, Q126K, I92F | SEQ ID NO:10 |

```
WT IL-2  APTSSSTKKTQLQLEHLLLDLQMILNGINNYKNPKLTRMLTFKFYMPKKATELKHLQCLEEELKPLEEVLNLAQ                  SEQ ID NO:1
         SKNFHLRPRDLISNINVIVLELKGSETTFMCEYADETATIVEFLNRWITFCQSIISTLT

H9 IL-2  APTSSSTKKTQLQLEHLLLDLQMILNGINNYKNPKLTRMLTFKFYMPKKATELKHLQCLEEELKPLEEVLNLAQ   L80F, R81D,     SEQ ID NO:2
         SKNFHEDPRDVVSNINVFVLELKGSETTFMCEYADETATIVEFLNRWITFCQSIISTLT                 L85V, I86V,
                                                                                     I92F

WT_REH   APTSSSTKKTQLQLEHLRLDLEMILNGINNYKNPKLTRMLTFKFYMPKKATELKHLQCLEEELKPLEEVLNLAQ   L18R, Q22E,     SEQ ID NO:15
         SKNFHLRPRDLISNINVIVLELKGSETTFMCEYADETATIVEFLNRWITFCHSIISTLT                 Q126H

H9_REH   APTSSSTKKTQLQLEHLRLDLEMILNGINNYKNPKLTRMLTFKFYMPKKATELKHLQCLEEELKPLEEVLNLAQ   L80F, R81D,     SEQ ID NO:8
         SKNFHEDPRDVVSNINVFVLELKGSETTFMCEYADETATIVEFLNRWITFCHSIISTLT                 L85V, I86V,
                                                                                     I92F
                                                                                     L18R, Q22E,
                                                                                     Q126H

WT_REM   APTSSSTKKTQLQLEHLRLDLEMILNGINNYKNPKLTRMLTFKFYMPKKATELKHLQCLEEELKPLEEVLNLAQ   L18R, Q22E,     SEQ ID NO:16
         SKNFHLRPRDLISNINVIVLELKGSETTFMCEYADETATIVEFLNRWITFCMSIISTLT                 Q126M
```

FIG. 2

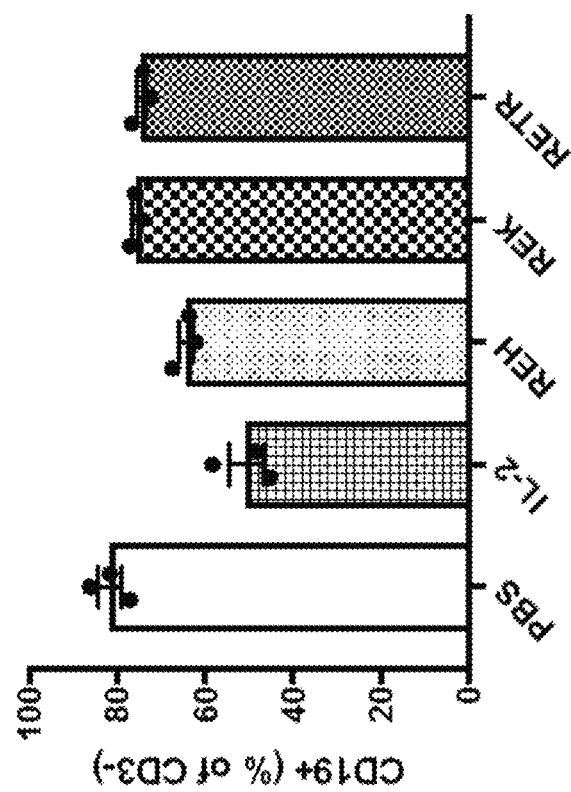
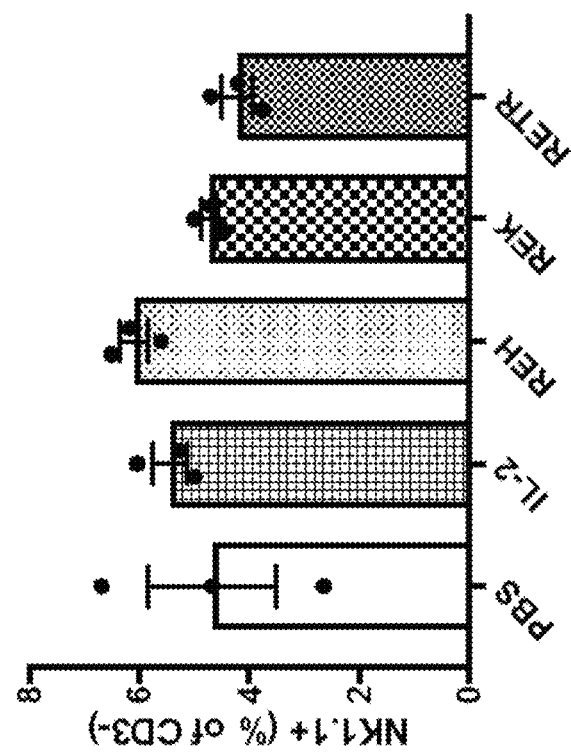
FIG. 8E
FIG. 8D

SEQUENCE LISTING

```
<160> NUMBER OF SEQ ID NOS: 22

<210> SEQ ID NO 1
<211> LENGTH: 133
<212> TYPE: PRT
<213> ORGANISM: Homo sapiens
<220> FEATURE:
<223> OTHER INFORMATION: WT IL-2

<400> SEQUENCE: 1

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 2
<211> LENGTH: 133
<212> TYPE: PRT
<213> ORGANISM: Homo sapiens
<220> FEATURE:
<223> OTHER INFORMATION: H9 IL-2
```

<400> SEQUENCE: 2

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 3
<211> LENGTH: 133
<212> TYPE: PRT
<213> ORGANISM: Artificial Sequence
<220> FEATURE:
<223> OTHER INFORMATION: IL-2 mutein H9_REA

<400> SEQUENCE: 3

Ala Pro Thr Ser Ser Ser Thr Lys Lys Thr Gln Leu Gln Leu Glu His
1               5                   10                  15

Leu Arg Leu Asp Leu Glu Met Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Ala Ser Ile
            115                 120                 125

Ile Ser Thr Leu Thr
        130

<210> SEQ ID NO 4
<211> LENGTH: 133
<212> TYPE: PRT
<213> ORGANISM: Artificial Sequence
<220> FEATURE:
<223> OTHER INFORMATION: IL-2 mutein H9_REC

<400> SEQUENCE: 4

Ala Pro Thr Ser Ser Ser Thr Lys Lys Thr Gln Leu Gln Leu Glu His
1               5                   10                  15

```
Leu Arg Leu Asp Leu Glu Met Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Phe
65                  70                  75                  80

Asp Pro Arg Asp Val Val Ser Asn Ile Asn Val Phe Val Leu Glu Leu
            85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Cys Ser Ile
            115                 120                 125

Ile Ser Thr Leu Thr
            130

<210> SEQ ID NO 5
<211> LENGTH: 133
<212> TYPE: PRT
<213> ORGANISM: Artificial Sequence
<220> FEATURE:
<223> OTHER INFORMATION: IL-2 mutein H9_RED

<400> SEQUENCE: 5

Ala Pro Thr Ser Ser Ser Thr Lys Lys Thr Gln Leu Gln Leu Glu His
1               5                   10                  15

Leu Arg Leu Asp Leu Glu Met Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Phe
65                  70                  75                  80

Asp Pro Arg Asp Val Val Ser Asn Ile Asn Val Phe Val Leu Glu Leu
            85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Asp Ser Ile
            115                 120                 125

Ile Ser Thr Leu Thr
            130

<210> SEQ ID NO 6
<211> LENGTH: 133
<212> TYPE: PRT
<213> ORGANISM: Artificial Sequence
<220> FEATURE:
<223> OTHER INFORMATION: IL-2 mutein H9_REE

<400> SEQUENCE: 6

Ala Pro Thr Ser Ser Ser Thr Lys Lys Thr Gln Leu Gln Leu Glu His
1               5                   10                  15

Leu Arg Leu Asp Leu Glu Met Ile Leu Asn Gly Ile Asn Asn Tyr Lys
            20                  25                  30

Asn Pro Lys Leu Thr Arg Met Leu Thr Phe Lys Phe Tyr Met Pro Lys
```

```
                  35                  40                  45
Lys Ala Thr Glu Leu Lys His Leu Gln Cys Leu Glu Glu Glu Leu Lys
 50                  55                  60

Pro Leu Glu Glu Val Leu Asn Leu Ala Gln Ser Lys Asn Phe His Phe
 65                  70                  75                  80

Asp Pro Arg Asp Val Val Ser Asn Ile Asn Val Phe Val Leu Glu Leu
                  85                  90                  95

Lys Gly Ser Glu Thr Thr Phe Met Cys Glu Tyr Ala Asp Glu Thr Ala
                 100                 105                 110

Thr Ile Val Glu Phe Leu Asn Arg Trp Ile Thr Phe Cys Glu Ser Ile
                 115                 120                 125

Ile Ser Thr Leu Thr
                 130

<210> SEQ ID NO 7
<211> LENGTH: 133
<212> TYPE: PRT
<213> ORGANISM: Artificial Sequence
<220> FEATURE:
<223> OTHER INFORMATION: IL-2 mutein H9_REG

<400> SEQUENCE: 7

Ala Pro Thr Ser Ser Ser Thr Lys Lys Thr Gln Leu Gln Leu Glu His
 1               5                  10                  15

Leu Arg Leu Asp Leu Glu Met Ile Leu Asn Gly Ile Asn Asn Tyr Lys
                  20                  25                  30

Asn Pro Lys Leu Thr Arg Met Leu Thr Phe Lys Phe Tyr Met Pro Lys
                  35                  40                  45

Lys Ala Thr Glu Leu Lys His Leu Gln Cys Leu Glu Glu Glu Leu Lys
 50                  55                  60

Pro Leu Glu Glu Val Leu Asn Leu Ala Gln Ser Lys Asn Phe His Phe
 65                  70                  75                  80

Asp Pro Arg Asp Val Val Ser Asn Ile Asn Val Phe Val Leu Glu Leu
                  85                  90                  95

Lys Gly Ser Glu Thr Thr Phe Met Cys Glu Tyr Ala Asp Glu Thr Ala
                 100                 105                 110

Thr Ile Val Glu Phe Leu Asn Arg Trp Ile Thr Phe Cys Gly Ser Ile
                 115                 120                 125

Ile Ser Thr Leu Thr
                 130

<210> SEQ ID NO 8
<211> LENGTH: 133
<212> TYPE: PRT
<213> ORGANISM: Artificial Sequence
<220> FEATURE:
<223> OTHER INFORMATION: IL-2 mutein H9_REH

<400> SEQUENCE: 8

Ala Pro Thr Ser Ser Ser Thr Lys Lys Thr Gln Leu Gln Leu Glu His
 1               5                  10                  15

Leu Arg Leu Asp Leu Glu Met Ile Leu Asn Gly Ile Asn Asn Tyr Lys
                  20                  25                  30

Asn Pro Lys Leu Thr Arg Met Leu Thr Phe Lys Phe Tyr Met Pro Lys
                  35                  40                  45

Lys Ala Thr Glu Leu Lys His Leu Gln Cys Leu Glu Glu Glu Leu Lys
 50                  55                  60
```

-continued

```
Pro Leu Glu Glu Val Leu Asn Leu Ala Gln Ser Lys Asn Phe His Phe
 65                  70                  75                  80

Asp Pro Arg Asp Val Val Ser Asn Ile Asn Val Phe Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys His Ser Ile
        115                 120                 125

Ile Ser Thr Leu Thr
        130
```

<210> SEQ ID NO 9
<211> LENGTH: 133
<212> TYPE: PRT
<213> ORGANISM: Artificial Sequence
<220> FEATURE:
<223> OTHER INFORMATION: IL-2 mutein H9_REI

<400> SEQUENCE: 9

```
Ala Pro Thr Ser Ser Thr Lys Lys Thr Gln Leu Gln Leu Glu His
  1               5                  10                  15

Leu Arg Leu Asp Leu Glu Met Ile Leu Asn Gly Ile Asn Asn Tyr Lys
                 20                  25                  30

Asn Pro Lys Leu Thr Arg Met Leu Thr Phe Lys Phe Tyr Met Pro Lys
             35                  40                  45

Lys Ala Thr Glu Leu Lys His Leu Gln Cys Leu Glu Glu Glu Leu Lys
         50                  55                  60

Pro Leu Glu Glu Val Leu Asn Leu Ala Gln Ser Lys Asn Phe His Phe
 65                  70                  75                  80

Asp Pro Arg Asp Val Val Ser Asn Ile Asn Val Phe Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Ile Ser Ile
        115                 120                 125

Ile Ser Thr Leu Thr
        130
```

<210> SEQ ID NO 10
<211> LENGTH: 133
<212> TYPE: PRT
<213> ORGANISM: Artificial Sequence
<220> FEATURE:
<223> OTHER INFORMATION: IL-2 mutein H9_REK

<400> SEQUENCE: 10

```
Ala Pro Thr Ser Ser Thr Lys Lys Thr Gln Leu Gln Leu Glu His
  1               5                  10                  15

Leu Arg Leu Asp Leu Glu Met Ile Leu Asn Gly Ile Asn Asn Tyr Lys
                 20                  25                  30

Asn Pro Lys Leu Thr Arg Met Leu Thr Phe Lys Phe Tyr Met Pro Lys
             35                  40                  45

Lys Ala Thr Glu Leu Lys His Leu Gln Cys Leu Glu Glu Glu Leu Lys
         50                  55                  60

Pro Leu Glu Glu Val Leu Asn Leu Ala Gln Ser Lys Asn Phe His Phe
 65                  70                  75                  80

Asp Pro Arg Asp Val Val Ser Asn Ile Asn Val Phe Val Leu Glu Leu
                 85                  90                  95
```

```
Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Lys Ser Ile
        115                 120                 125

Ile Ser Thr Leu Thr
        130

<210> SEQ ID NO 11
<211> LENGTH: 133
<212> TYPE: PRT
<213> ORGANISM: Artificial Sequence
<220> FEATURE:
<223> OTHER INFORMATION: IL-2 mutein H9_REM

<400> SEQUENCE: 11

Ala Pro Thr Ser Ser Ser Thr Lys Lys Thr Gln Leu Gln Leu Glu His
1               5                   10                  15

Leu Arg Leu Asp Leu Glu Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Met Ser Ile
        115                 120                 125

Ile Ser Thr Leu Thr
        130

<210> SEQ ID NO 12
<211> LENGTH: 133
<212> TYPE: PRT
<213> ORGANISM: Artificial Sequence
<220> FEATURE:
<223> OTHER INFORMATION: IL-2 mutein H9_RER

<400> SEQUENCE: 12

Ala Pro Thr Ser Ser Ser Thr Lys Lys Thr Gln Leu Gln Leu Glu His
1               5                   10                  15

Leu Arg Leu Asp Leu Glu Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Met Ser Ile
```

Ile Ser Thr Leu Thr
    130

<210> SEQ ID NO 13
<211> LENGTH: 133
<212> TYPE: PRT
<213> ORGANISM: Artificial Sequence
<220> FEATURE:
<223> OTHER INFORMATION: IL-2 mutein H9_RER

<400> SEQUENCE: 13

Ala Pro Thr Ser Ser Ser Thr Lys Lys Thr Gln Leu Gln Leu Glu His
1               5                   10                  15

Leu Arg Leu Asp Leu Glu Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Arg Ser Ile
        115                 120                 125

Ile Ser Thr Leu Thr
    130

<210> SEQ ID NO 14
<211> LENGTH: 133
<212> TYPE: PRT
<213> ORGANISM: Artificial Sequence
<220> FEATURE:
<223> OTHER INFORMATION: IL-2 mutein H9_RES

<400> SEQUENCE: 14

Ala Pro Thr Ser Ser Ser Thr Lys Lys Thr Gln Leu Gln Leu Glu His
1               5                   10                  15

Leu Arg Leu Asp Leu Glu Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Ser Ser Ile
        115                 120                 125

Ile Ser Thr Leu Thr
    130

<210> SEQ ID NO 15
<211> LENGTH: 133
<212> TYPE: PRT
<213> ORGANISM: Artificial Sequence
<220> FEATURE:
<223> OTHER INFORMATION: IL-2 mutein WT_REH

<400> SEQUENCE: 15

```
Ala Pro Thr Ser Ser Ser Thr Lys Lys Thr Gln Leu Gln Leu Glu His
1               5                   10                  15

Leu Arg Leu Asp Leu Glu Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys His Ser Ile
        115                 120                 125

Ile Ser Thr Leu Thr
        130
```

<210> SEQ ID NO 16
<211> LENGTH: 133
<212> TYPE: PRT
<213> ORGANISM: Artificial Sequence
<220> FEATURE:
<223> OTHER INFORMATION: IL-2 mutein WT_REM

<400> SEQUENCE: 16

```
Ala Pro Thr Ser Ser Ser Thr Lys Lys Thr Gln Leu Gln Leu Glu His
1               5                   10                  15

Leu Arg Leu Asp Leu Glu Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Met Ser Ile
        115                 120                 125

Ile Ser Thr Leu Thr
        130
```

<210> SEQ ID NO 17
<211> LENGTH: 149
<212> TYPE: PRT
<213> ORGANISM: Homo sapiens
<220> FEATURE:
<223> OTHER INFORMATION: human IL-2, GenBank NP_000577.2

<400> SEQUENCE: 17

```
Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Phe Tyr
    50                  55                  60

Met Pro Lys Ala Thr Glu Leu His Leu Gln Cys Leu Glu Glu Glu Leu
65                  70                  75                  80

Lys Pro Leu Glu Glu Val Leu Asn Leu Ala Gln Ser Lys Asn Phe His
                85                  90                  95

Leu Arg Pro Arg Asp Leu Ile Ser Asn Ile Val Ile Val Leu Glu Leu
            100                 105                 110

Lys Gly Ser Glu Thr Thr Phe Met Cys Glu Tyr Ala Asp Glu Thr Ala
        115                 120                 125

Thr Ile Val Glu Phe Leu Asn Arg Trp Ile Thr Phe Cys Gln Ser Ile
    130                 135                 140

Ile Ser Thr Leu Thr
145
```

<210> SEQ ID NO 18
<211> LENGTH: 167
<212> TYPE: PRT
<213> ORGANISM: Mus musculus
<220> FEATURE:
<223> OTHER INFORMATION: murine IL-2

<400> SEQUENCE: 18

```
Met Tyr Ser Met Gln Leu Ala Ser Cys Val Thr Leu Thr Leu Val Leu
1               5                   10                  15

Leu Val Asn Ser Ala Pro Thr Ser Ser Ser Thr Ser Ser Ser Thr Ala
            20                  25                  30

Glu Ala Gln Gln Gln Gln Gln Gln Gln Gln Gln Gln Gln His Leu
        35                  40                  45

Glu Gln Leu Leu Met Asp Leu Gln Glu Leu Leu Ser Arg Met Glu Asn
    50                  55                  60

Tyr Arg Asn Leu Lys Leu Pro Arg Met Leu Thr Phe Lys Phe Tyr Leu
65                  70                  75                  80

Pro Gln Ala Thr Glu Leu Lys Asp Leu Gln Cys Leu Glu Asp Glu Leu
                85                  90                  95

Gly Pro Leu Arg His Val Leu Asp Leu Thr Gln Ser Lys Ser Phe Gln
            100                 105                 110

Leu Glu Asp Ala Glu Asn Phe Ile Ser Asn Ile Arg Val Thr Val Val
        115                 120                 125

Leu Lys Gly Ser Asp Asn Thr Phe Glu Cys Gln Phe Asp Asp Glu Ser
    130                 135                 140

Ala Thr Val Val Asp Phe Leu Arg Arg Trp Ile Ala Phe Cys Gln Ser
145                 150                 155                 160

Ile Ile Ser Thr Ser Pro Gln
                165
```

```
<210> SEQ ID NO 19
<211> LENGTH: 149
<212> TYPE: PRT
<213> ORGANISM: Mus musculus
<220> FEATURE:
<223> OTHER INFORMATION: mature murine IL-2

<400> SEQUENCE: 19

Ala Pro Thr Ser Ser Thr Ser Ser Thr Ala Glu Ala Gln Gln
1               5                   10                  15

Gln Gln Gln Gln Gln Gln Gln Gln His Leu Glu Gln Leu Leu
            20                  25                  30

Met Asp Leu Gln Glu Leu Leu Ser Arg Met Glu Asn Tyr Arg Asn Leu
            35                  40                  45

Lys Leu Pro Arg Met Leu Thr Phe Lys Phe Tyr Leu Pro Lys Gln Ala
    50                  55                  60

Thr Glu Leu Lys Asp Leu Gln Cys Leu Glu Asp Glu Leu Gly Pro Leu
65                  70                  75                  80

Arg His Val Leu Asp Leu Thr Gln Ser Lys Ser Phe Gln Leu Glu Asp
                85                  90                  95

Ala Glu Asn Phe Ile Ser Asn Ile Arg Val Thr Val Val Lys Leu Lys
            100                 105                 110

Gly Ser Asp Asn Thr Phe Glu Cys Gln Phe Asp Asp Glu Ser Ala Thr
        115                 120                 125

Val Val Asp Phe Leu Arg Arg Trp Ile Ala Phe Cys Gln Ser Ile Ile
    130                 135                 140

Ser Thr Ser Pro Gln
145

<210> SEQ ID NO 20
<211> LENGTH: 133
<212> TYPE: PRT
<213> ORGANISM: Artificial Sequence
<220> FEATURE:
<223> OTHER INFORMATION: mutein IL-2
<220> FEATURE:
<221> NAME/KEY: VARIANT
<222> LOCATION: (18)..(18)
<223> OTHER INFORMATION: Xaa = Leu or Arg
<220> FEATURE:
<221> NAME/KEY: misc_feature
<222> LOCATION: (18)..(18)
<223> OTHER INFORMATION: residue 18 can be either present or absent
<220> FEATURE:
<221> NAME/KEY: VARIANT
<222> LOCATION: (22)..(22)
<223> OTHER INFORMATION: Xaa = Gln or Glu
<220> FEATURE:
<221> NAME/KEY: misc_feature
<222> LOCATION: (22)..(22)
<223> OTHER INFORMATION: residue 22 can be either present or absent
<220> FEATURE:
<221> NAME/KEY: VARIANT
<222> LOCATION: (80)..(80)
<223> OTHER INFORMATION: Xaa = Leu or Phe or Val
<220> FEATURE:
<221> NAME/KEY: misc_feature
<222> LOCATION: (80)..(80)
<223> OTHER INFORMATION: residue 80 can be either present or absent
<220> FEATURE:
<221> NAME/KEY: VARIANT
<222> LOCATION: (81)..(81)
<223> OTHER INFORMATION: Xaa = Arg or Ile or Thr or Asp
<220> FEATURE:
<221> NAME/KEY: misc_feature
<222> LOCATION: (81)..(81)
<223> OTHER INFORMATION: residue 81 can be either present or absent
<220> FEATURE:
```

```
<221> NAME/KEY: VARIANT
<222> LOCATION: (85)..(85)
<223> OTHER INFORMATION: Xaa = Leu or Val
<220> FEATURE:
<221> NAME/KEY: misc_feature
<222> LOCATION: (85)..(85)
<223> OTHER INFORMATION: residue 85 can be either present or absent
<220> FEATURE:
<221> NAME/KEY: VARIANT
<222> LOCATION: (86)..(86)
<223> OTHER INFORMATION: Xaa = Ile or Val
<220> FEATURE:
<221> NAME/KEY: misc_feature
<222> LOCATION: (86)..(86)
<223> OTHER INFORMATION: residue 86 can be either present or absent
<220> FEATURE:
<221> NAME/KEY: VARIANT
<222> LOCATION: (92)..(92)
<223> OTHER INFORMATION: Xaa = Ile or Phe
<220> FEATURE:
<221> NAME/KEY: misc_feature
<222> LOCATION: (92)..(92)
<223> OTHER INFORMATION: residue 92 can be either present or absent
<220> FEATURE:
<221> NAME/KEY: VARIANT
<222> LOCATION: (126)..(126)
<223> OTHER INFORMATION: Xaa = Gln or His or Met or Lys or Cys or Asp or
      Glu or Gly or Ile or Arg or Ser or Thr
<220> FEATURE:
<221> NAME/KEY: misc_feature
<222> LOCATION: (126)..(126)
<223> OTHER INFORMATION: residue 126 can be either present or absent

<400> SEQUENCE: 20

Ala Pro Thr Ser Ser Ser Thr Lys Lys Thr Gln Leu Gln Leu Glu His
1               5                   10                  15

Leu Xaa Leu Asp Leu Xaa Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Xaa
65                  70                  75                  80

Xaa Pro Arg Asp Xaa Xaa Ser Asn Ile Asn Val Xaa Val Leu Glu Leu
            85                  90                  95

Lys Gly Ser Glu Thr Thr Phe Met Cys Glu Tyr Ala Asp Glu Thr Ala
        100                 105                 110

Thr Ile Val Glu Phe Leu Asn Arg Trp Ile Thr Phe Cys Xaa Ser Ile
    115                 120                 125

Ile Ser Thr Leu Thr
    130

<210> SEQ ID NO 21
<211> LENGTH: 133
<212> TYPE: PRT
<213> ORGANISM: Artificial Sequence
<220> FEATURE:
<223> OTHER INFORMATION: IL-2 mutein WT_ RETR

<400> SEQUENCE: 21

Ala Pro Thr Ser Ser Ser Thr Lys Lys Thr Gln Leu Gln Leu Glu His
1               5                   10                  15

Leu Arg Leu Asp Leu Glu Met Ile Leu Asn Gly Ile Asn Asn Tyr Lys
            20                  25                  30

Asn Pro Lys Leu Thr Arg Met Leu Thr Phe Lys Phe Tyr Met Pro Lys
```

```
                35                  40                  45
Lys Ala Thr Glu Leu Lys His Leu Gln Cys Leu Glu Glu Leu Lys
             50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Thr Ser Ile
                115                 120                 125

Ile Arg Thr Leu Thr
            130

<210> SEQ ID NO 22
<211> LENGTH: 133
<212> TYPE: PRT
<213> ORGANISM: Artificial Sequence
<220> FEATURE:
<223> OTHER INFORMATION: IL-2 mutein WT_REK

<400> SEQUENCE: 22

Ala Pro Thr Ser Ser Ser Thr Lys Lys Thr Gln Leu Gln Leu Glu His
 1               5                  10                  15

Leu Arg Leu Asp Leu Glu Met Ile Leu Asn Gly Ile Asn Asn Tyr Lys
                 20                  25                  30

Asn Pro Lys Leu Thr Arg Met Leu Thr Phe Lys Phe Tyr Met Pro Lys
             35                  40                  45

Lys Ala Thr Glu Leu Lys His Leu Gln Cys Leu Glu Glu Glu Leu Lys
             50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Lys Ser Ile
                115                 120                 125

Ile Ser Thr Leu Thr
            130
```

PARTIAL AGONISTS OF INTERLEUKIN-2

CROSS-REFERENCE TO RELATED APPLICATIONS

The present application is a continuation application of U.S. patent application Ser. No. 16/765,617, filed on May 20, 2020, which is a U.S. National Phase Application of PCT International Application No. PCT/US2018/062122, filed on Nov. 20, 2018, designating the United States of America, which is an International Application of and claims the benefit of priority to U.S. Provisional Patent Application Ser. No. 62/589,497, filed on Nov. 21, 2017. The disclosures of the above-referenced applications are herein expressly incorporated by reference it their entireties, including any drawings.

REFERENCE TO THE SEQUENCE LISTING

The present application is being filed along with a Sequence Listing in electronic format. The Sequence Listing is provided as a file entitled "Sequence_Listing_078430-503C01US.txt", created May 13, 2021, which is approximately 32 KB in size. The information in the electronic format of the Sequence Listing is incorporated herein by reference in its entirety.

STATEMENT REGARDING FEDERALLY SPONSORED R&D

The invention was made with government support under R37 AI051321 awarded by the National Institutes of Health. The government has certain rights in the present invention.

FIELD

Disclosed herein, inter alia, are interleukin-2 muteins that exhibit the properties of partial agonism of the IL-2 receptor signal as well as methods for using the same for the treatment of autoimmune diseases.

BACKGROUND

Interleukin 2 (IL-2) is a pluripotent cytokine produced primarily by activated CD4+ T cells, which plays a crucial role in producing a normal immune response. IL-2 promotes proliferation and expansion of activated T lymphocytes, potentiates B cell growth, and activates monocytes and natural killer cells.

In addition to its physiological role in the normal immune response, IL-2 can promote pathologic responses, and a therapeutic goal is to maintain desired actions of this cytokine while blocking unwanted autoimmune or immunosuppressive responses. Two monoclonal antibodies (mAbs) to human IL-2Rα, Daclizumab and Basiliximab, are approved by the FDA and exhibit efficacy in renal transplantation rejection (Vincenti et al., *N Engl J Med* 338: 161 (1998)), cardiac transplantation (Hershberger et al., *N Engl J Med* 352: 2705 (2005)), multiple sclerosis (Gold et al., *Lancet* 381: 2167 (2013)), and asthma (Bielekova et al., *Proc. Natl. Acad. Sci. USA* 101: 8705 (2004); and Busse et al., *Am J Respir Crit Care Med* 178: 1002 (2008)) but they do not block IL-2 signaling via intermediate affinity IL-2Rγ receptors expressed on NK and memory CD8+ cells (Tkaczuk et al., *Am J Transplant* 2: 31 (2002)). Although anti-human IL-2Rβ mAb Mikβ1 can block trans-presentation of IL-2 and IL-15 to cells expressing IL-2Rγ receptors (Morris et al., *Proc. Natl. Acad. Sci. USA* 103: 401 (2006)), it is relatively ineffective in blocking cis-signaling by IL-2 or IL-15 via their high affinity heterotrimeric receptor complexes (Morris et al., *Proc. Natl. Acad. Sci. USA* 103: 401 (2006); and Waldmann et al., *Blood* 121: 476 (2013)). Consequently, new IL-2 muteins are needed that can promote the therapeutically beneficial effects of this cytokine but that also block one or more IL-2 functions that are associated with unwanted autoimmune or immunosuppressive responses.

SUMMARY OF THE INVENTION

The present disclosure relates generally to the field of immunology and medicine, including compositions and methods for modulating signal transduction pathway mediated by interleukin 2 (IL-2) in a subject in need thereof. More particularly, in some embodiments, the disclosure provides novel IL-2 muteins with modulated affinity for at least one of the IL-2 receptors, e.g., interleukin 2 alpha receptor (IL-2Rα), interleukin 2 beta receptor (IL-2Rβ), interleukin-2 gamma receptor (IL-2Rγ). Some embodiments of the disclosure provide IL-2 partial agonists that do not promote activation of immune cells responsible for undesired adverse autoimmune events, such as inflammation. Some embodiments of the disclosure relate to compositions and methods useful for producing such IL-2 muteins, as well as methods for the treatment of health conditions and disorders associated with perturbations of signal transduction mediated by IL-2 signaling pathway.

In one aspect, there is provided an interleukin 2 (IL-2) mutein having: (a) reduced binding affinity for interleukin 2 receptor γ (IL-2Rγ) as compared to an IL-2 polypeptide encoded by SEQ ID NO: 2; and (b) 15-95% $E_{max}$ as compared to the polypeptide encoded by SEQ ID NO: 2. In some embodiments, the IL-2 mutein includes: (i) one or more amino acid substitutions that increase IL-2Rβ binding affinity compared to the polypeptide encoded by SEQ ID NO: 1, selected from L80F, R81D, L85V, I86V, and I92F, numbered in accordance with the amino acid sequence of SEQ ID NO: 1; and/or (ii) one or more amino acid substitutions that reduce IL-2Rγ receptor binding affinity and results in 15-95% of $E_{max}$ compared to the polypeptide encoded by SEQ ID NO: 2, selected from (A) L18R and Q22E; and (B) the amino acid position 126, numbered in accordance with the amino acid sequence of SEQ ID NO: 2. In some embodiments, the amino acid substitution at position 126 of SEQ ID NO: 2 is selected from the group consisting of Q126A, Q126C, Q126D, Q126E, Q126G, Q126H, Q126I, Q126K, Q126M, Q126R, Q126S, or Q126T. In some embodiments, the IL-2 mutein includes the amino acid substitution Q126H, Q126K, or Q126M. In some embodiments, the IL-2 mutein includes an amino acid substitution Q126H.

In some embodiments, the IL-2 mutein is structurally modified to increase half-life. In some embodiments, the modification includes one or more modifications selected from the group consisting of fusion to a human Fc antibody fragment, fusion to albumin, and PEGylation. In some embodiments, the IL-2 mutein causes expansion of $T_{reg}$ cells and does not promote expansion of potentially inflammatory T cells and Natural Killer (NK) cell or granulocytes. In some embodiments, the IL-2 mutein induces less proliferation of potentially inflammatory T cells compared to the polypeptide encoded by SEQ ID NO: 1 or SEQ ID NO: 2. In some embodiments, the IL-2 mutein increases proliferation of $T_{reg}$ cells by at least 3 fold and/or induces less IFNγ secretion compared to the polypeptide encoded by SEQ ID NO: 1 or SEQ ID NO: 2. In some embodiments, the potentially inflammatory T cells are CD4$^+$ IFNγ$^+$ T cells or are CD8$^+$ IFNγ$^+$ T cells. In some embodiments of any of the embodiments disclosed herein, the mutein does not induce IFNγ secretion from CD8$^+$ T cells and/or other inflammatory immune cell subsets. In some embodiments, the mutein has 70-95% $E_{max}$ as compared to the polypeptide encoded by SEQ ID NO: 1

In one aspect, provided herein is an interleukin 2 (IL-2) mutein having (a) reduced binding affinity for interleukin 2 receptor γ (IL-2Rγ); and (b) 15-95% $E_{max}$ as compared to a polypeptide encoded by SEQ ID NO: 1. In some embodiments, the mutein includes one or more amino acid substitutions that reduce IL-2Rγ receptor binding affinity and results in 15-95% $E_{max}$ as compared to a polypeptide encoded by SEQ ID NO: 1, selected from (A) L18R and Q22E; and (B) amino acid position 126, numbered in accordance with the amino acid sequence of SEQ ID NO: 1. In some embodiments, the IL-2 mutein includes an amino acid substitution at position 126 of SEQ ID NO: 1 selected from the group consisting of Q126A, Q126C, Q126D, Q126E, Q126G, Q126H, Q126I, Q126K, Q126M, Q126R, Q126S, or Q126T. In some embodiments, the IL-2 mutein includes an amino acid substitution Q126H, Q126K, or Q126M. In some embodiments, the IL-2 mutein includes an amino acid substitution Q126H. In some embodiments, the IL-2 mutein is structurally modified to increase half-life. In some embodiments, the modification includes one or more modifications selected from the group consisting of fusion to a human Fc antibody fragment, fusion to albumin, and PEGylation. In some embodiments, the IL-2 mutein of the disclosure increases proliferation of regulatory T ($T_{reg}$) cells and/or induces minimal proliferation of potentially inflammatory T cells. In some embodiments, the IL-2 mutein of the disclosure causes expansion of $T_{reg}$ cells and does not promote expansion of potentially inflammatory T cells and Natural Killer (NK) cell or granulocytes. In some embodiments, the IL-2 mutein induces less proliferation of potentially inflammatory T cells compared to the polypeptide encoded by SEQ ID NO: 1 or SEQ ID NO: 2. In some embodiments, the potentially inflammatory T cells are CD4$^+$ IFNγ$^+$ T cells or are CD8$^+$IFNγ$^+$ T cells. In some embodiments, the potentially inflammatory T cells are CD4$^+$ IFNγ$^+$ T cells or are CD8$^+$IFNγ$^+$ T cells. In some embodiments, the IL-2 mutein increases proliferation of $T_{reg}$ cells by at least 3 fold and/or induces less IFNγ secretion compared to the polypeptide encoded by SEQ ID NO: 1 or SEQ ID NO: 2. In some embodiments, the mutein does not induce IFNγ secretion from CD8$^+$ T cells and/or other inflammatory immune cell subsets. In some embodiments, the IL-2 mutein of the disclosure has 70-95% $E_{max}$ as compared to the polypeptide encoded by SEQ ID NO: 1.

In further aspects, provided herein are (i) nucleic acids encoding any one of the IL-2 muteins disclosed herein, (ii) vectors including the nucleic acids, (iii) host cells including the vectors or nucleic acids, and (iv) sterile pharmaceutical compositions including any one of the IL-2 muteins disclosed herein, and/or any of the nucleic acids or vectors disclosed herein and a pharmaceutically acceptable excipient.

In further aspects, also provided herein are syringes and catheters including a syringe including any one of the IL-2 muteins disclosed herein, any of the nucleic acids or vectors disclosed herein, and/or any of the pharmaceutical compositions disclosed herein.

In yet other aspects, provided herein are kits including: (i) any one of the IL-2 muteins disclosed herein, (ii) any one of the nucleic acids or vectors disclosed herein, (iii) any one of the syringes or catheters disclosed herein, and/or any one of the pharmaceutical compositions disclosed herein as well as written instructions for using the same.

In another aspect, provided herein are methods for treating an autoimmune disease in an individual in need thereof, the method including administering a therapeutically effective amount of (i) any one of the IL-2 muteins disclosed herein, (ii) any one of the nucleic acids or vectors disclosed herein, and/or (iii) any one of the pharmaceutical compositions disclosed herein to the individual. In some embodiments, the autoimmune disease is selected from the group consisting of rheumatoid arthritis, insulin-dependent diabetes mellitus, hemolytic anemias, rheumatic fever, thyroiditis, Crohn's disease, myasthenia gravis, glomerulonephritis, autoimmune hepatitis, multiple sclerosis, alopecia areata, psoriasis, vitiligo, dystrophic epidermolysis bullosa, systemic lupus erythematosus, and graft vs. host disease. In some embodiments, the autoimmune disease is graft vs. host disease. In some embodiments of the methods disclosed herein, the method further includes administering any of the IL-2 muteins or pharmaceutical compositions disclosed herein in combination with an antibody that targets the mutein to a specific cell type. In some embodiments, the cell type is a regulatory T ($T_{reg}$) cell. In some embodiments, the antibody is covalently or non-covalently linked to the Il-2 mutein.

In other aspects, provided herein are methods for producing any one of the muteins disclosed herein, the method including culturing any of the host cells disclosed herein under suitable conditions for the production of the mutein. In other embodiments, the method further includes isolating and/or purifying the mutein. In some embodiments, the method further includes structurally modifying the mutein to increase half-life. In other embodiments, the method further includes, the modification includes one or more modifications selected from the group consisting of fusion to a human Fc antibody fragment, fusion to albumin, and PEGylation.

Also provided herein, in some aspects, are methods for preventing the proliferation of potentially inflammatory T cells and/or preventing secretion of IFNγ from CD8$^+$ T cells or other inflammatory immune cell subsets, the methods including contacting a cell expressing an interleukin 2 receptor γ (IL-2Rγ) with any of the IL-2 muteins disclosed herein. In other embodiments, the potentially inflammatory T cells are CD4$^+$CD44$^+$IFNγ$^+$ T cells or are CD8$^+$CD44$^+$IFNγ$^+$ T cells. In some embodiments, the method is performed in vitro, in vivo, or ex vivo. In some embodiments of any of the embodiments disclosed herein, the IL-2 mutein is structurally modified to increase half-life. In some embodiments of any of the embodiments disclosed herein, the modification is one or more modifications selected from the group consisting of fusion to a human Fc antibody fragment, fusion to albumin, and PEGylation.

In another aspect, provided herein are methods for decreasing proliferation of regulatory T ($T_{reg}$) cells including contacting a $T_{reg}$ cell with an interleukin 2 (IL-2) mutein having: (i) reduced binding affinity for interleukin 2 receptor γ (IL-2Rγ) as compared to the polypeptide encoded by SEQ ID NO: 2; and (ii) 0-50% $E_{max}$ as compared to the polypeptide encoded by SEQ ID NO: 2. In some embodiments, the IL-2 mutein includes: (i) one or more amino acid substitutions that increase IL-2Rβ binding affinity compared to the polypeptide encoded by SEQ ID NO: 1, selected from L80F, R81D, L85V, I86V, and I92F, numbered in accordance with the amino acid sequence of SEQ ID NO: 1; and (ii) one or more amino acid substitutions that reduce IL-2Rγ receptor binding affinity and results in 0-50% of the $E_{max}$ compared to the polypeptide encoded by SEQ ID NO: 2, selected from (A) L18R and Q22E; and (B) the amino acid position 126, numbered in accordance with the amino acid sequence of SEQ ID NO: 2.

In another aspect, provided herein are methods for decreasing proliferation of regulatory T ($T_{reg}$) cells including contacting a $T_{reg}$ cell with an IL-2 mutein having: (i) reduced binding affinity for IL-2Rγ as compared to the polypeptide encoded by SEQ ID NO: 1; and (ii) 0-50% $E_{max}$ as compared to the polypeptide encoded by SEQ ID NO: 1. In some embodiments, the Il-2 mutein includes one or more amino acid substitutions that reduce IL-2Rγ receptor binding affinity and results in 0-50% $E_{max}$ as compared to a polypeptide encoded by SEQ ID NO: 1, selected from (A) L18R and Q22E; and (B) amino acid position 126, numbered in accordance with the amino acid sequence of SEQ ID NO: 1. In some embodiments, the amino acid substitution at position 126 of SEQ ID NO: 1 or SEQ ID NO: 2 is selected from the group consisting of Q126A, Q126C, Q126D, Q126E, Q126G, Q126H, Q126I, Q126K, Q126M, Q126R, Q126S, or Q126T. In some embodiments, the Il-2 mutein includes the amino acid substitution Q126H, Q126K, or Q126M. In some embodiments, the Il-2 mutein includes an amino acid substitution Q126H. In some embodiments of any of the embodiments disclosed herein, the method further includes administering the IL2 muteins with an antibody that targets the mutein to a $T_{reg}$ cell. In some embodiments of any of the embodiments disclosed herein, the antibody is covalently or non-covalently linked to the mutein. In some embodiments of any of the embodiments disclosed herein, the method is performed in vitro, in vivo, or ex vivo.

Each of the aspects and embodiments described herein are capable of being used together, unless excluded either explicitly or clearly from the context of the embodiment or aspect.

The foregoing summary is illustrative only and is not intended to be in any way limiting. In addition to the illustrative embodiments and features described herein, further aspects, embodiments, objects and features of the disclosure will become fully apparent from the drawings and the detailed description and the claims.

BRIEF DESCRIPTION OF THE DRAWINGS

FIG. 1. depicts the amino acid sequences of wild-type IL-2 and muteins constructed using the H9 background.

FIG. 2. depicts the amino acid sequences of wild-type IL-2 and muteins constructed using the wild-type background.

FIG. 4A depicts the results of a p-STAT5 signaling assay on YT cells stimulated for 15 min with indicated concentration of IL-2 partial agonists. The Y axis shows the ratio of p-STAT5 signal from each IL-2 variant normalized to p-STAT5 signal from WT IL-2 for each concentration. FIG. 4A depicts YT cells were stimulated at various time points with 1 μM of different IL-2 variants as indicated on the graph. The Y axis indicates the median fluorescence intensity (MFI) for p-STAT5 signal.

FIG. 6A depicts human NK-like YT cells while FIG. 6B depicts mouse starved T cell blasts (B) stimulated for 15 min with various human IL-2 variants fused to mouse serum albumin (MSA) at different concentrations as indicated on the graph (from 5 μM to 0 μM). The Y axis shows the ratio of p-STAT5 signal from each IL-2 variant normalized to p-STAT5 signal from WT IL-2 for each concentration.

FIG. 7A depicts changes in tumor volume. FIG. 7B, FIG. 7C, FIG. 7D, and FIG. 7E depict the frequency of the indicated immune cell subset for each condition normalized to the respective frequency in WT mice.

FIGS. 8A-8G graphically summarize the results from experiments performed to demonstrate that several exemplary IL-2R partial agonists can elicit cell type specific responses in vivo.

DETAILED DESCRIPTION OF THE DISCLOSURE

Figure 3:
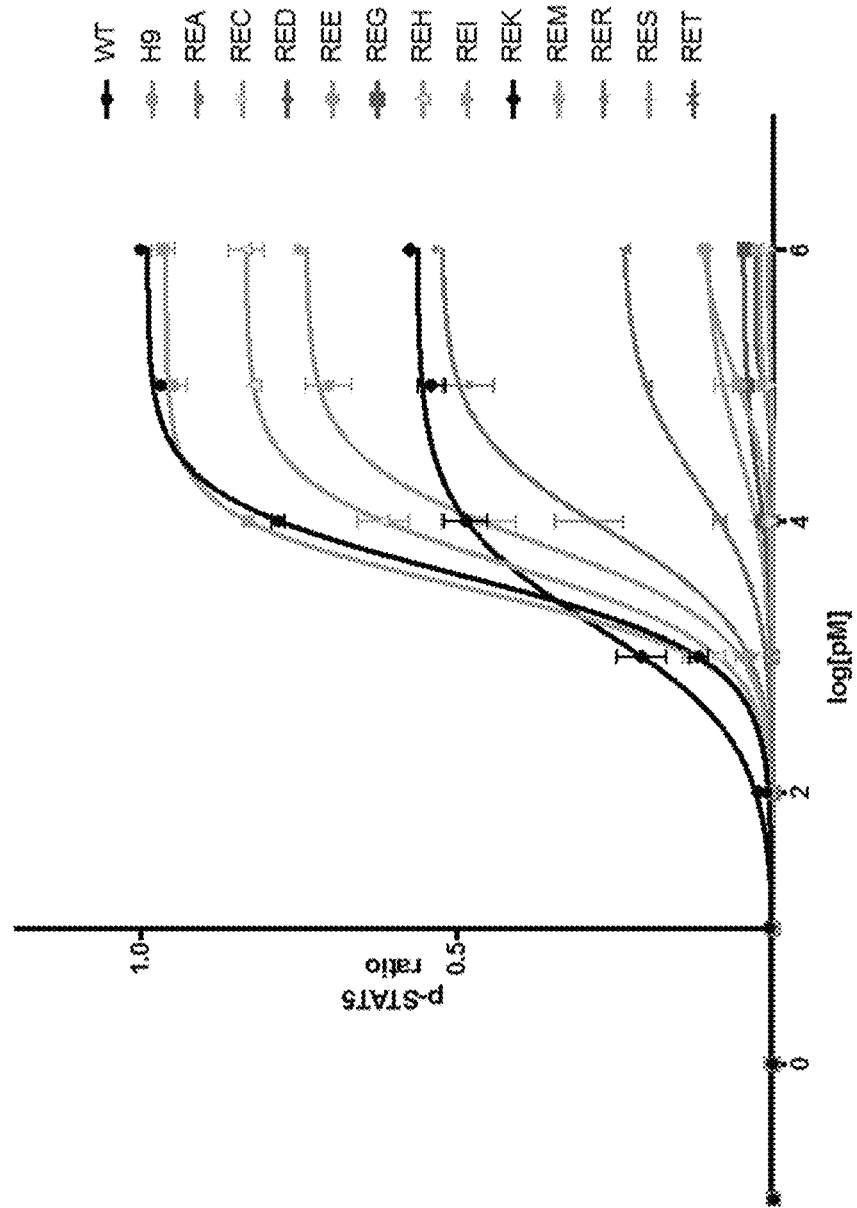
FIG. 3 depicts the results of a phospho-STAT5 signaling assay with dose response of IL-2 variants. Human NK-like YT cells were stimulated for 15 min with various human IL-2 variants fused to mouse serum albumin (MSA) at different concentrations as indicated on the graph (from 1 μM to 0 μM, 10-fold dilution). The Y axis shows the ratio of p-STAT5 signal from each IL-2 variant normalized to p-STAT5 signal from WT IL-2 for each concentration.

The present disclosure relates generally to the field of immunology and medicine, including compositions and methods for modulating signal transduction pathway mediated by interleukin 2 (IL-2) in a subject in need thereof. More particularly, in some embodiments, the disclosure provides novel IL-2 muteins with modulated affinity for at least one of the IL-2 receptors, e.g., interleukin 2 alpha receptor (IL-2Rα), interleukin 2 beta receptor (IL-2Rβ), interleukin-2 gamma receptor (IL-2Rγ), whereby either completely or partially antagonizing the downstream signal transduction mediated through the respective IL-2Rα, IL-2Rβ, and/or IL-2Rγ receptors. Some embodiments of the disclosure provide IL-2 partial agonists that do not promote activation of immune cells responsible for undesired adverse autoimmune events, such as inflammation. Some embodiments of the disclosure relate to compositions and methods useful for producing such IL-2 muteins, as well as methods for the treatment of health conditions and disorders associated with perturbations of signal transduction mediated by IL-2 signaling pathway.

IL-2 exerts a wide spectrum of effects on the immune system and it plays crucial roles in regulating both immune activation and homeostasis. As an immune system stimulator, IL-2 has found use in the treatment of cancer and chronic viral infections. However, the stimulatory effects of IL-2 can also cause havoc, mediating autoimmunity and transplant rejection. Because of its instrumental role in immune regulation and disease, the identification of new IL-2 molecules, such as IL-2 partial agonists, remains an active area of research.

In most circumstances, IL-2 works through three different receptors: the IL-2Rα, the IL-2Rβ, and the IL-2Rγ. Most cells, such as resting T cells, are not responsive to IL-2 since they only express the IL-2Rβ and the IL-2Rγ, which have low affinity for IL-2. Upon stimulation, resting T cells express the relatively high affinity IL-2Rα. Binding of IL-2 to the IL-2Rα causes this receptor to sequentially engage the IL-2Rβ, and the IL-2Rγ, bringing about T cell activation.

The disclosure described herein provides, inter alia, novel IL-2 compositions which are based on new insights into how IL-2 interacts with its cognate receptors, in particular, IL-2Rγ. The inventors have surprisingly discovered that mutations in the IL-2 binding site for IL-2Rγ result in partial agonists capable of activating regulatory T cells ($T_{regs}$). Further, these IL-2 partial agonists do not activate $CD8^+$ T cells and other potentially inflammatory immune cell subsets and do not induce inflammatory cells to secrete interferon-gamma (IFNγ). As such, these molecules can be used to treat autoimmune disorders and conditions.

I. General Techniques

The practice of the present disclosure will employ, unless otherwise indicated, conventional techniques of molecular biology, microbiology, cell biology, biochemistry, nucleic acid chemistry, and immunology, which are well known to those skilled in the art. Such techniques are explained fully in the literature, such as, *Molecular Cloning: A Laboratory Manual*, fourth edition (Sambrook et al., 2012) and *Molecular Cloning: A Laboratory Manual*, third edition (Sambrook and Russel, 2001), (jointly referred to herein as "Sambrook"); *Current Protocols in Molecular Biology* (F. M. Ausubel et al., eds., 1987, including supplements through 2014); *PCR: The Polymerase Chain Reaction*, (Mullis et al., eds., 1994); Beaucage et al. eds., *Current Protocols in Nucleic Acid Chemistry*, John Wiley & Sons, Inc., New York, 2000, (including supplements through 2014), *Gene Transfer and. Expression in Mammalian Cells* (Makrides, ed., Elsevier Sciences B.V., Amsterdam, 2003), and *Current Protocols in Immunology* (Horgan K and S. Shaw (1994) (including supplements through 2014). As appropriate, procedures involving the use of commercially available kits and reagents are generally carried out in accordance with manufacturer defined protocols and/or parameters unless otherwise noted.

II. Definition

Unless otherwise defined, all terms of art, notations and other scientific terms or terminology used herein are intended to have the meanings commonly understood by those of skill in the art to which this disclosure pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

The singular form "a", "an", and "the" include plural references unless the context clearly dictates otherwise. For example, the term "a cell" includes one or more cells, including mixtures thereof. "A and/or B" is used herein to include all of the following alternatives: "A", "B", "A or B", and "A and B".

The term "about", as used herein, has its ordinary meaning of approximately. If the degree of approximation is not otherwise clear from the context, "about" means either within plus or minus 10% of the provided value, or rounded to the nearest significant figure, in all cases inclusive of the provided value. Where ranges are provided, they are inclusive of the boundary values.

As used herein, the term "IL-2" means wild-type IL-2, whether native or recombinant. As such, an IL-2 polypeptide refers to any IL-2 polypeptide, including but not limited to, a recombinant produced IL-2 polypeptide, synthetically produced IL-2 polypeptide, IL-2 extracted from cells or tissues. Mature human IL-2 occurs as a 133 amino acid sequence (less the signal peptide, consisting of an additional 20 N-terminal amino acids), as described in Fujita, et al., *Proc. Natl. Acad. Sci. USA*, 80, 7437-7441 (1983). The amino acid sequence of human IL-2 (SEQ ID NO: 17) is found in Genbank under accession locator NP_000577.2. The amino acid sequence of mature human IL-2 is depicted in SEQ ID NO: 1. The murine (*Mus musculus*) IL-2 amino acid sequence is found in Genbank under accession locator (SEQ ID NO: 18). The amino acid sequence of mature murine IL-2 is depicted in SEQ ID NO: 19.

As used herein, "IL-2 mutein" means an IL-2 polypeptide wherein specific substitutions to the interleukin-2 protein have been made. The IL-2 muteins are characterized by amino acid insertions, deletions, substitutions and modifications at one or more sites in or at the other residues of the native IL-2 polypeptide chain. In accordance with this disclosure, any such insertions, deletions, substitutions and modifications result in an IL-2 mutein that retains the IL-2R binding activity. For example, the muteins disclosed herein can have high or low affinity for IL-2Rα and/or IL-2Rβ or can have an affinity for these receptors identical or similar to that of wild-type IL-2. Exemplary muteins can include substitutions of 1, 2, 3, 4, 5, 6, 7, 8, 9, 10 or more amino acids. Muteins can also include conservative modifications and substitutions at other positions of IL-2 (i.e., those that have a minimal effect on the secondary or tertiary structure of the mutein). Such conservative substitutions include those described by Dayhoff in The Atlas of Protein Sequence and Structure 5 (1978), and by Argos in *EMBO J*, 8:779-785 (1989). For example, amino acids belonging to one of the following groups represent conservative changes: Group I: Ala, Pro, Gly, Gln, Asn, Ser, Thr; Group II: Cys, Ser, Tyr, Thr; Group III: Val, Ile, Leu, Met, Ala, Phe; Group IV: Lys, Arg, His; Group V: Phe, Tyr, Trp, His; and Group VI: Asp, Glu.

The phrase "numbered in accordance with" means identifying a chosen amino acid with reference to the position at which that amino acid normally occurs in a given amino acid sequence, such as, the amino acid sequence of wild-type IL-2. For example, R81 refers to the eighty-first amino acid, arginine, that occurs in SEQ ID NO: 1.

The term "identity," as used herein in reference to polypeptide or DNA sequences, refers to the subunit sequence identity between two molecules. When a subunit position in both of the molecules is occupied by the same monomeric subunit (i.e., the same amino acid residue or nucleotide), then the molecules are identical at that position. The similarity between two amino acid or two nucleotide sequences is a direct function of the number of identical positions. In general, the sequences are aligned so that the highest order match is obtained. If necessary, identity can be calculated using published techniques and widely available computer programs, such as the GCS program package (Devereux et al., Nucleic Acids Res. 12:387, 1984), BLASTP, BLASTN, FASTA (Atschul et al., J. Molecular Biol. 215:403, 1990). Sequence identity can be measured using sequence analysis software such as the Sequence Analysis Software Package of the Genetics Computer Group at the University of Wisconsin Biotechnology Center (1710 University Avenue, Madison, Wis. 53705), with the default parameters thereof.

As used herein, the terms "protein" and "polypeptide" refer to a polymer of amino acid residues and are not limited to a minimum length of the product. Thus, polypeptides, peptides, fragments of polypeptides, fusion polypeptides, oligopeptides, and the like are encompassed within the definition. Both full-length proteins and fragments thereof are encompassed by the definition. The terms also include post-expression modifications of the polypeptide, for example, glycosylation, acetylation, phosphorylation and the like. Furthermore, for purposes of the present disclosure, a "polypeptide" refers to a protein which includes modifications, such as deletions, additions and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification. Thus, the term "IL-2 polypeptide" refers to native IL-2 sequences, as well as to IL-2 analogs, IL-2 muteins and fragments, unless excluded either explicitly or clearly from the context of the embodiment or aspect.

As used herein "potentially inflammatory T cells" or "inflammatory immune cell subsets" refer to one or more T cells that produce, secrete, or are capable of producing or secreting interferon gamma. In some embodiments, potentially inflammatory T cells express CD44 on their cell surface and produce or secrete interferon gamma. In other embodiments, potentially inflammatory T cells express CD44 and CD4 on their cell surface and produce or secrete interferon gamma. In further embodiments, potentially inflammatory T cells express CD44 and CD8 on their cell surface and produce or secrete interferon gamma. In yet other embodiments, potentially inflammatory T cells express CD4 and CD8 on their cell surface and produce or secrete interferon gamma.

As used herein, "regulatory T cells" or "$T_{reg}$ cells" refer to T cells (T lymphocytes) that regulate the activity of other T cell(s) and/or other immune cells, usually by suppressing their activity. In some embodiments, the $T_{reg}$ cells are CD4$^+$ and FoxP3$^+$ cells (but it will be appreciated by persons skilled in the art that $T_{reg}$ cells are not fully restricted to this phenotype).

"$E_{max}$," as referred to herein, is the maximal p-STAT5 signal that can be generated by IL-2 muteins measured at a highest concentration. $E_{max}$ from WT IL-2 is used as a reference to calculate a ratio of p-STAT5 signal from IL-2 muteins normalized to p-STAT5 signal from WT IL-2 at the highest concentration.

An "agonist" is a compound that interacts with a target to cause or promote an increase in the activation of the target.

A "partial agonist" is a compound that interacts with the same target as an agonist but does not produce as great a magnitude of a biochemical and/or physiological effect as the agonist, even by increasing the dosage of the partial agonist.

A "super agonist" is a type of agonist that is capable of producing a maximal response greater than the endogenous agonist for the target receptor, and thus has an efficacy of more than 100%.

An "antagonist" is a compound that opposes the actions of an agonist, e.g. by preventing, reducing, inhibiting, or neutralizing the activity of an agonist. An "antagonist" can also prevent, inhibit, or reduce constitutive activity of a target, e.g., a target receptor, even where there is no identified agonist.

"Operably linked" is intended to mean that the nucleotide sequence of interest (i.e., a sequence encoding an IL-2 mutein) is linked to the regulatory sequence(s) in a manner that allows for expression of the nucleotide sequence (e.g., in an in vitro transcription/translation system or in a host cell when the vector is introduced into the host cell). "Regulatory sequences" include promoters, enhancers, and other expression control elements (e.g., polyadenylation signals). See, for example, Goeddel (1990) in *Gene Expression Technology: Methods in Enzymology* Vol. 185 (Academic Press, San Diego, Calif). Regulatory sequences include those that direct constitutive expression of a nucleotide sequence in many types of host cells and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression constructs of the present disclosure can be introduced into host cells to thereby produce the human IL-2 muteins disclosed herein or to produce biologically active variants thereof.

The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell but are still included within the scope of the term as used herein.

The term "vector" is used herein to refer to a nucleic acid molecule or sequence capable transferring or transporting another nucleic acid molecule. The transferred nucleic acid is generally linked to, e.g., inserted into, the vector nucleic acid molecule. A vector may include sequences that direct autonomous replication in a cell, or may include sequences sufficient to allow integration into host cell DNA. Useful vectors include, for example, plasmids (e.g., DNA plasmids or RNA plasmids), transposons, cosmids, bacterial artificial chromosomes, and viral vectors. Useful viral vectors include, e.g., replication defective retroviruses and lentiviruses. In one aspect, a vector is a gene delivery vector. In one aspect, a vector is used as a gene delivery vehicle to transfer a gene into a cell.

As used herein, the terms "transformation" and "transfection" refer to a variety of art-recognized techniques for introducing foreign nucleic acid (e.g., DNA) into a host cell, including calcium phosphate or calcium chloride co-precipitation, DEAE-dextran-mediated transfection, lipofection, particle gun, or electroporation.

As used herein, a "subject" or an "individual" or a "patient" includes animals, such as human (e.g., human subjects) and non-human animals. The term "non-human animals" includes all vertebrates, e.g., mammals, e.g., rodents, e.g., mice, and non-mammals, such as non-human primates, e.g., sheep, dogs, cows, chickens, amphibians, reptiles, etc.

As used herein, the term "pharmaceutically acceptable carrier" includes, but is not limited to, saline, solvents, dispersion media, coatings, antibacterial and antifungal agents, isotonic and absorption delaying agents, and the like, compatible with pharmaceutical administration. Supplementary active compounds (e.g., antibiotics) can also be incorporated into the compositions.

It is understood that aspects and embodiments of the disclosure described herein include "comprising," "consisting," and "consisting essentially of" aspects and embodiments.

As will be understood by one having ordinary skill in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

Headings, e.g., (a), (b), (i) etc., are presented merely for ease of reading the specification and claims. The use of headings in the specification or claims does not require the steps or elements be performed in alphabetical or numerical order or the order in which they are presented.

III. Compositions of the Disclosure

Some aspects of the disclosure relate to novel IL-2 muteins with modulated affinity, e.g., increased or reduced binding affinity for one or more IL-2 receptors (e.g., IL-2Rα, IL-2Rβ, and/or IL-2Rγ) as compared to a wild-type IL-2 polypeptide. In particular, some embodiments of the disclosure relate to L-2 muteins, in which one or more molecular alterations that confer reduced binding affinity for IL-2Rα, IL-2Rβ, and/or IL-2Rγ. Stated differently, some of the novel IL-2 muteins disclosed herein partial agonists of the IL-2 mediated signaling pathway. In some embodiments, the IL-2 partial agonists disclosed herein do not promote activation of immune cells responsible for undesired adverse autoimmune events, such as inflammation.

A. IL-2 Partial Agonists

In one aspect, some embodiments of the disclosure provide IL-2 muteins that are partial agonists. In some embodiments, provided herein are IL-2 muteins that contain one or more mutations that reduces the binding affinity of the IL-2 mutein for IL-2Rγ$_c$ receptor as compared to wild-type IL-2 (e.g., human IL-2, SEQ ID NO: 2). As used herein, the terms, "common gamma chain," "γ$_c$," "IL-2Rγ$_c$," "Yc,", "IL-2Rγ," "IL-2 receptor subunit gamma," and "IL-2RG" (Genbank accession numbers: NM_000206 and NP_000197 (human) and NM_013563 and NP_038591 (mouse)) all refer to a member of the type I cytokine receptor family that is a cytokine receptor subunit to the receptor complexes for at least six different interleukin receptor including, but not limited to, IL-2, IL-4, IL-7, IL-9, IL-15, and IL-21 receptors. IL-2Rγ$_c$ interacts with IL-2Rβ to form an intermediate affinity IL-2 receptor primarily on memory T cells and natural killer (NK) cells and interacts with IL-2Rα and IL-2Rβ to form a high affinity IL-2 receptor on activated T cells and Tregs.

In some embodiments, the IL-2 muteins as disclosed herein artificial recombinant IL-2 muteins, and can be, for example, any recombinant IL-2 polypeptide, engineered IL-2 polypeptide, or naturally-occurring IL-2 polypeptide which has a modulated binding affinity to a IL-2 receptor (e.g., IL-2Rα, IL-2Rβ, and/or IL-2Rγ).

Exemplary subject IL-2 muteins are at least about 50%, at least about 65%, at least about 70%, at least about 80%, at least about 85%, at least about 87%, at least about 90%, at least about 91%, at least about 92%, at least about 93%, at least about 94%, at least about 95%, at least about 96%, at least about 97%, at least about 98%, or at least about 99% identical to the corresponding wild-type IL-2 (WT IL-2). The mutation can consist of a change in the number or content of amino acid residues. For example, the mutant IL-2 can have a greater or a lesser number of amino acid residues than the corresponding wild-type IL-2. Alternatively, or in addition, an exemplary mutant polypeptide can contain a substitution of one or more amino acid residues that are present in the wild-type IL-2. In various embodiments, the mutant IL-2 polypeptide can differ from wild-type IL-2 by the addition, deletion, or substitution of a single amino acid residue.

By way of non-limiting illustration, an IL-2 mutein that includes an amino acid sequence that is at least 95% identical to the reference amino acid sequence SEQ ID NO: 1 is a polypeptide that includes a sequence that is identical to the reference sequence except for the inclusion of up to five alterations of the reference amino acid sequence of SEQ ID NO: 2. Accordingly, in some embodiments, the IL-2 mutein of the disclosure includes an amino acid sequence that is at least 95% identical to the reference amino acid sequence SEQ ID NO: 1 is a polypeptide that includes a sequence that is identical to the reference sequence except for the inclusion of 1, 2, 3, 4, or 5 alterations of the reference amino acid sequence. For example, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence can occur at the amino (N−) or carboxy (C−) terminal positions of the reference amino acid sequence or anywhere between those terminal positions, interspersed either individually among residues in the reference sequence or in one or more contiguous groups within the reference sequence.

In some embodiments, the IL-2 mutein of the disclosure binds IL-2Rγ with an affinity that is at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99% less than wild-type IL-2, inclusive of any value falling in between these percentages. The binding affinity of IL-2 mutein can also be expressed as 1.2, 1.4, 1.5, 2, 5, 10, 15, 20, 25, 50, 100, 200, 250 or more fold lower affinity for the IL-2γ than wild-type IL-2. The binding affinity of a subject IL-2 mutein for IL-2Rγ can be measured using any suitable method known in the art. Suitable methods for measuring IL-2Rγ binding, include, but are not limited to, radioactive ligand binding assays (e.g., saturation binding, scatchard plot, nonlinear curve fitting programs and competition binding assays); non-radioactive ligand binding assays (e.g., fluorescence polarization (FP), fluorescence resonance energy transfer (FRET) and surface plasmon resonance assays (see, e.g., Drescher et al., *Methods Mol Biol* 493:323-343 (2009)); liquid phase ligand binding assays (e.g., real-time polymerase chain reaction (RT-qPCR), and immunoprecipitation); and solid phase ligand binding assays (e.g., multi-well plate assays, on-bead ligand binding assays, on-column ligand binding assays, and filter assays). Without being bound to theory, it is believed that partial agonists constructed thorough mutations in the IL-2Rγ receptor binding site would be less dose-dependent compared to wild-type or other variants of IL-2.

In some embodiments, the IL-2 mutein disrupts the association of the IL-2Rβ with the IL-2Rγ such that this IL-2Rβ/IL-2Rγ interaction is reduced by about 2%, about 5%, about 10%, about 15%, about 20%, about 50%, about 75%, about 90%, about 95% or more (inclusive of any value falling in between these percentages) relative to wild-type IL-2.

In some embodiments, the one or more mutations reducing the binding affinity of the IL-2 mutein for IL-2Rγ receptor is an amino acid substitution. In some embodiments, the subject IL-2 mutein consists of 1, 2, 3, 4, 5, 6, 7, 8, 9, 10, 11, 12, 13, 14, or 15 amino acid substitutions as compared to a wild-type IL-2 (SEQ ID NO: 1). The substituted amino acid residue(s) can be, but are not necessarily, conservative substitutions, which typically include substitutions within the following groups: glycine, alanine; valine, isoleucine, leucine; aspartic acid, glutamic acid; asparagine, glutamine; serine, threonine; lysine, arginine; and phenylalanine, tyrosine. In particular embodiments, the substitutions are at amino acid residues of IL-2 that contact the IL-2Rγ binding interface.

In some embodiments, the amino acid substitutions are substitutions at one or more amino acid positions of wild-type IL-2 selected from positions: 18, 22, and 126, numbered in accordance with wild-type hIL-2 (e.g., SEQ ID NO: 1). In some embodiments, the amino acid substitutions that decrease IL-2Rγ receptor binding affinity include amino acid substitutions Leu-to-Arg (L18R), Gln-to-Glu (Q22E), and/or one of Gln-to-His (Q126H), Gln-to-Met (Q126M) or Gln-to-Lys (Q126K) or combinations thereof.

In further embodiments, the amino acid substitution that decreases IL-2Rγ receptor binding affinity includes L18R and Q22E and any of Q126A, Q126C, Q126D, Q126E, Q126G, Q126H, Q126I, Q126K, Q126M, Q126R, Q126S, or Q126T. In yet other embodiments, the IL-2 mutein can have additional amino acid substitutions at one or more amino acid positions of wild-type IL-2 selected from positions: 80, 81, 85, 86, and 192, numbered in accordance with wild-type hIL-2 (e.g., SEQ ID NO: 1). In another embodiment, the IL-2 mutein can have additional amino acid substitutions selected from one or more of L80F, R81D, L85V, I86V, and/or I92F.

In some embodiments, the IL-2 mutein can further have an increased binding affinity for the IL-2Rβ receptor and can further include 1, 2, 3, 4, 5, 6, 7, 8, 9, or 10 or more mutations that increase IL-2Rβ binding affinity. As used herein, the terms "IL-2Rβ" and "CD122" (Genbank accession number NM_000878 and NP_000869 (human)) both refer to a member of the type I cytokine receptor family that interacts with IL-2Rγ to form an intermediate affinity IL-2 receptor primarily on memory T cells and natural killer (NK) cells and interacts with IL-2Rα and IL-2Rγ to form a high affinity IL-2 receptor on activated T cells and regulator T cells ($T_{regs}$). In some embodiments, the subject IL-2 mutein includes at least one mutation (e.g., a deletion, addition, or substitution of 1, 2, 3, 4, 5, 6, 7, 8, 9, 10, 11, 12, 13, 14, 15, 16, 17, 18, 19, 20, or more amino acid residues) relative to a wild-type IL-2 (e.g., SEQ ID NO: 1), and binds the IL-2Rβ with higher affinity than a wild-type IL-2. In some embodiments, the IL-2 mutein binds IL-2Rβ with an affinity that is at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99% greater than wild-type IL-2 (inclusive of any value falling in between these percentages). The binding affinity of IL-2 mutein can also be expressed as 1.2, 1.4, 1.5, 2, 5, 10, 15, 20, 25, 50, 100, 200, 250 or more fold greater affinity for the IL-2Rβ than wild-type IL-2. Binding of the subject IL-2 mutein to IL-2Rβ can be assessed by any suitable method known to those in the art, including, but not limited to the methods described above. In some embodiments, the at least one mutation increasing IL-2Rβ binding affinity is an amino acid substitution. In some embodiments, the amino acid substitutions that increase IL-2Rβ binding affinity include substitutions at amino acid positions I24, P65, Q74, L80, R81, L85, I86, I89, I92, and/or V93 numbered in accordance with wild-type hIL-2 (SEQ ID NO: 1): In some embodiments, the substitutions include I24V, P65H, Q74R, Q74H, Q74N, Q74S, L80F, L80V, R81I, R81T, R81D, L85V, I86V, I89V, I92F, and/or V93I or combinations thereof. In some embodiments, the substitutions include Q74N, Q74H, Q74S, L80F, L80V, R81D, R81T, L85V, I86V, I89V, and/or I93V or combinations thereof.

In some embodiments, the IL-2 mutein can further have a decreased binding affinity for the IL-2Rβ receptor and can further include 1, 2, 3, 4, 5, 6, 7, 8, 9, or 10 or more mutations that decrease IL-2Rβ binding affinity. In some embodiments, the subject IL-2 mutein includes at least one mutation (e.g., a deletion, addition, or substitution of 1, 2, 3, 4, 5, 6, 7, 8, 9, 10, 11, 12, 13, 14, 15, 16, 17, 18, 19, 20, or more amino acid residues) relative to a wild-type IL-2 (e.g., SEQ ID NO: 1), and binds the IL-2Rβ with decreased affinity compared to a wild-type IL-2. In some embodiments, the IL-2 mutein binds IL-2Rβ with an affinity that is at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99% less than wild-type IL-2 (inclusive of any value falling in between these percentages). The binding affinity of IL-2 mutein can also be expressed as 1.2, 1.4, 1.5, 2, 5, 10, 15, 20, 25, 50, 100, 200, 250 or more fold less affinity for the IL-2Rβ than wild-type IL-2.

In further embodiments, any of the IL-2 muteins disclosed herein can bind to the IL-2Rβ receptor with an affinity similar (for example, varying by less than a percent) or identical to a wild-type IL-2 (e.g., SEQ ID NO: 1).

In additional embodiments, the IL-2 mutein can further have an increased binding affinity for the IL-2Rα receptor and can further include 1, 2, 3, 4, 5, 6, 7, 8, 9, or 10 or more mutations that increase IL-2Rα binding affinity. As used herein, the terms "IL-2Rα" and "CD25" (Genbank accession number NM_000417 and NP_000408 (human)) both refer to a member of the type I cytokine receptor family that interacts with IL-2Rβ and IL-2Rγ to form a high affinity IL-2 receptor on activated T cells and regulator T cells (Tregs). In some embodiments, the subject IL-2 mutein includes at least one mutation (e.g., a deletion, addition, or substitution of 1, 2, 3, 4, 5, 6, 7, 8, 9, 10, 11, 12, 13, 14, 15, 16, 17, 18, 19, 20, or more amino acid residues) relative to a wild-type IL-2 (e.g., SEQ ID NO: 1), and binds the IL-2Rα with higher affinity than a wild-type IL-2. In some embodiments, the IL-2 mutein binds IL-2Rα with an affinity that is at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99% greater than wild-type IL-2 (inclusive of any value falling in between these percentages). The binding affinity of IL-2 mutein can also be expressed as 1.2, 1.4, 1.5, 2, 5, 10, 15, 20, 25, 50, 100, 200, 250 or more fold greater affinity for the IL-2Rβ than wild-type IL-2. Binding of the subject IL-2 mutein to IL-2Rα can be assessed by any suitable method known to those in the art, including, but not limited to the methods described above. In some embodiments, the at least one mutation increasing IL-2Rβ binding affinity is an amino acid substitution.

In yet other embodiments, the IL-2 mutein can further have a decreased binding affinity for the IL-2Rα receptor and can further include 1, 2, 3, 4, 5, 6, 7, 8, 9, or 10 or more mutations that decrease IL-2Rα binding affinity. In some embodiments, the subject IL-2 mutein includes at least one mutation (e.g., a deletion, addition, or substitution of 1, 2, 3, 4, 5, 6, 7, 8, 9, 10, 11, 12, 13, 14, 15, 16, 17, 18, 19, 20, or more amino acid residues) relative to a wild-type IL-2 (e.g., SEQ ID NO: 1), and binds the IL-2Rα with less affinity than a wild-type IL-2. In some embodiments, the IL-2 mutein binds IL-2Rα with an affinity that is at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99% less than wild-type IL-2 (inclusive of any value falling in between these percentages). The binding affinity of IL-2 mutein can also be expressed as 1.2, 1.4, 1.5, 2, 5, 10, 15, 20, 25, 50, 100, 200, 250 or more fold less affinity for the IL-2Rα than wild-type IL-2.

In further embodiments, any of the IL-2 muteins disclosed herein can bind to the IL-2Rα receptor with an affinity similar (for example, varying by less than a percent) or identical to a wild-type IL-2 (e.g., SEQ ID NO: 1).

In some embodiments, the Il-2 mutein includes amino acid substitutions L80F, R81D, L85V, I86V, I92F, L18R, Q22E, and Q126H. In some embodiments, the IL-2 mutein has the following amino acid sequence:

```
                                          (SEQ ID NO: 8)
APTSSSTKKTQLQLEHLRLDLEMILNGINNYKNPKLTRMLTFKFYMPKK

ATELKHLQCLEEELKPLEEVLNLAQSKNFHFDPRDVVSNINVFVLELKG

SETTFMCEYADETATIVEFLNRWITFCHSIISTLT
```

In other embodiments, the Il-2 mutein includes amino acid substitutions L80F, R81D, L85V, I86V, I92F, L18R, Q22E, and Q126K. In some embodiments, the IL-2 mutein has the following amino acid sequence:

```
                                         (SEQ ID NO: 10)
APTSSSTKKTQLQLEHLRLDLEMILNGINNYKNPKLTRMLTFKFYMPKK

ATELKHLQCLEEELKPLEEVLNLAQSKNFHFDPRDVVSNINVFVLELKG

SETTFMCEYADETATIVEFLNRWITFCKSIISTLT
```

In further embodiments, the Il-2 mutein includes amino acid substitutions L80F, R81D, L85V, I86V, I92F, L18R, Q22E, and Q126M. In some embodiments, the IL-2 mutein has the following amino acid sequence:

```
                                         (SEQ ID NO: 11)
APTSSSTKKTQLQLEHLRLDLEMILNGINNYKNPKLTRMLTFKFYMPKK

ATELKHLQCLEEELKPLEEVLNLAQSKNFHFDPRDVVSNINVFVLELKG

SETTFMCEYADETATIVEFLNRWITFCMSIISTLT.
```

In another embodiment, the Il-2 mutein includes amino acid substitutions L18R, Q22E, and Q126H. In some embodiments, the IL-2 mutein has the following amino acid sequence:

```
                                         (SEQ ID NO: 15)
APTSSSTKKTQLQLEHLRLDLEMILNGINNYKNPKLTRMLTFKFYMPKK

ATELKHLQCLEEELKPLEEVLNLAQSKNFHLRPRDLISNINVIVLELKG

SETTFMCEYADETATIVEFLNRWITFCHSIISTLT
```

In another embodiment, the Il-2 mutein includes amino acid substitutions L18R, Q22E, and Q126M. In some embodiments, the IL-2 mutein has the following amino acid sequence:

```
                                         (SEQ ID NO: 16)
APTSSSTKKTQLQLEHLRLDLEMILNGINNYKNPKLTRMLTFKFYMPKK

ATELKHLQCLEEELKPLEEVLNLAQSKNFHLRPRDLISNINVIVLELKG

SETTFMCEYADETATIVEFLNRWITFCMSIISTLT.
```

In various embodiments, the subject IL-2 mutein has an amino acid sequence according to the formula:

A-P-T-S-S-S-T-K-K-T-Q-L-Q-L-E-H-L-$(X^1)_n$-L-D-L-$(X^2)_n$-M-I-L-N-G-I-N-N-Y-K-N-P-K-L-T-R-M-L-T-F-K-F-Y-M-P-K-K-A-T-E-L-K-H-L-Q-C-L-E-E-E-L-K-P-L-E-E-V-L-N-L-A-Q-S-K-N-F-H-$(X^3)_n$-$(X^4)_n$-P-R-D-$(X^5)_n$-$(X^6)_n$-S-N-I-N-V-$(X^7)_n$-V-L-E-L-K-G-S-E-T-T-F-M-C-E-Y-A-D-E-T-A-T-I-V-E-F-L-N-RW-I-T-F-C-$(X^{13})_n$-S-I-I-S-T-L-T, wherein:
  each n is individually selected from 0 or 1;
  $X^1$ is L (wild-type) or R;
  $X^2$ is Q (wild-type) or E;
  $X^3$ is L (wild-type), F or V;
  $X^4$ is R (wild-type), I, T or D;
  $X^5$ is L (wild-type) or V;
  $X^6$ is I (wild-type) or V;
  $X^7$ is I (wild-type) or F;
  $X^{13}$ is Q (wild-type) or H, M, K, C, D, E, G, I, R, S, or T (SEQ ID NO: 20).

In some embodiments of the IL-2 mutein according to SEQ ID NO: 20, an amino acid at least at one of $X^1$, $X^2$, $X^3$, $X^4$, $X^5$, $X^6$, $X^7$, $X^8$, $X^9$, $X^{10}$, $X^{11}$, $X^{12}$, or $X^{13}$ is not a wild-type amino acid. In some embodiments, an amino acid at least at two, three, four, five, six, seven, eight, nine, ten, eleven, twelve, thirteen, or fourteen of $X^1$, $X^2$, $X^3$, $X^4$, $X^5$, $X^6$, $X^7$, $X^8$, $X^9$, $X^{10}$, $X^{11}$, $X^{12}$, or $X^{13}$ is not a wild-type amino acid. In some embodiments, the IL-2 mutein has at least about 95%, at least about 96%, at least about 97%, at least about 98%, at least about 99% or about 100% homology with the IL-2 mutein of SEQ ID NO: 20.

In some embodiments, the subject IL-2 muteins that are partial agonists have one or more reduced functions, as compared to wild-type IL-2, such as (i) reduced $E_{max}$, (ii) reduced capability to stimulate signaling pathways that are dependent on IL-2Rβ/IL-2Rγ heterodimerization, (iii) reduced production and/or secretion of interferon-gamma (IFNγ) from potentially inflammatory immune cells, (iv) reduced proliferation of potentially inflammatory T cells.

In some embodiments, the IL-2 mutein has reduced capabilities to stimulate one or more signaling pathways that are dependent on IL-2Rβ/IL-2Rγ heterodimerization. In some embodiments, the subject IL-2 mutein has a reduced capability to stimulate STAT5 phosphorylation in a T cell as compared to wild-type hIL-2 (see, e.g., Example 1 and FIGS. 4A-4B). In some embodiments, the IL-2 mutein stimulates STAT5 phosphorylation in an a T cell at a level that is 1%, 5%, 10%, 15%, 20%, 25%, 30%, 35%, 40%, 45%, 50%, 55%, 60%, 65%, 70%, 75%, 80%, 85%, 90%, 95% (inclusive of values in between these percentages) of the level that wild-type IL-2 stimulates STAT5 phosphorylation in the same cell. In some embodiments, the T cell is a natural killer (NK) cell. STAT5 signaling can be measure, for example, by phosphorylation of STAT5 using any suitable method known in the art. For example, STAT5 phosphorylation can be measured using antibodies specific for the phosphorylated version of this molecule in combination with flow cytometry analysis.

In further embodiments, the IL-2 muteins disclosed herein have a reduced $E_{max}$ compared to the $E_{max}$ of wild-type IL-2. In some embodiments, the muteins have any of about 15-95%, such as about 20-95%, about 30-95%, about 40-95%, about 50-95%, about 60-95%, about 70-95%, about 80-95%, or about 90-95% $E_{max}$ compared wild-type IL-2 (such as, the polypeptide encoded by SEQ ID NO: 1). In some embodiments, the IL-2 muteins disclosed herein have 15-95% $E_{max}$ compared to the $E_{max}$ of wild-type IL-2. In some embodiments, the IL-2 muteins disclosed herein have 70-95% $E_{max}$ compared to the $E_{max}$ of wild-type IL-2. In another embodiment, the IL-2 muteins discloses herein have any of about 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, or 95% $E_{max}$ compared wild-type IL-2 (such as, the polypeptide encoded by SEQ ID NO: 1). In one non-limiting embodiment, $E_{max}$ is calculated based on the ratio of maximal level of STAT5 phosphorylation (pSTAT5) induced in an immune cell by the IL-2 mutein relative to the maximal p-STAT5 signal generated by wild-type IL-2.

In yet other embodiments, the IL-2 muteins disclosed herein can results in less interferon-gamma (IFNγ) production and/or secretion from potentially inflammatory immune cells compared to the amount of IFNγ production and/or secretion induced by wild-type IL-2 (such as, the polypeptide encoded by SEQ ID NO: 1) (see, e.g., Example 2 and FIGS. 5A-5D). The reduction in IFNγ production and/or secretion can be at a level that is about 1%, 5%, 10%, 15%, 20%, 25%, 30%, 35%, 40%, 45%, 50%, 55%, 60%, 65%, 70%, 75%, 80%, 85%, 90%, 95%, or 100% (inclusive of values in between these percentages) of the level that wild-type IL-2 stimulates in potentially inflammatory immune cells at comparable concentrations and under similar conditions. In some embodiments, the IL-2 muteins disclosed herein do not induce IFNγ secretion from potentially inflammatory immune cells. In a non-limiting embodiment, the potentially inflammatory immune cell is a CD8$^+$ T cell and/or other inflammatory immune cell subset. In another non-limiting embodiment, the potentially inflammatory immune cell is a CD4$^+$ IFNγ$^+$ T cell or a CD8$^+$IFNγ$^+$ T cell.

In further embodiments, the IL-2 muteins disclosed herein can results in less proliferation of potentially inflammatory T cells compared to the proliferation of potentially inflammatory T cells induced by wild-type IL-2 (such as, the polypeptide encoded by SEQ ID NO: 1). Non-limiting exemplifications of potentially inflammatory T cells include CD4$^+$IFNγ$^+$ T cell or a CD8$^+$IFNγ$^+$ T cells. In some embodiments, the reduction in proliferation of potentially inflammatory T cells can be at a level that is 1%, 5%, 10%, 15%, 20%, 25%, 30%, 35%, 40%, 45%, 50%, 55%, 60%, 65%, 70%, 75%, 80%, 85%, 90%, 95%, or 100% (inclusive of values in between these percentages) or less of the level that wild-type IL-2 stimulates at comparable concentrations and under similar conditions. In some embodiments, the IL-2 muteins disclosed herein do not induce any proliferation of potentially inflammatory immune cells. In a non-limiting embodiment, the potentially inflammatory immune cell is a CD8$^+$ T cell and/or other inflammatory immune cell subset. In another non-limiting embodiment, the potentially inflammatory immune cell is a CD4$^+$IFNγ$^+$ T cell or a CD8$^+$IFNγ$^+$ T cell.

In still other embodiments, the IL-2 muteins disclosed herein can have increased functions such as, for example increased proliferation of $T_{reg}$ cells. In some embodiments, the IL-2 muteins disclosed herein can increase the proliferation of $T_{reg}$ cells by any of 1, 2, 3, 4, 5, 6, 7, 8, 9, or 10 fold compared to the amount of proliferation of $T_{reg}$ cells induced by wild-type IL-2 (such as, the polypeptide encoded by SEQ ID NO: 1). In some embodiments, the IL-2 muteins disclosed herein can increase the proliferation of $T_{reg}$ cells by any of about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, or 95% compared to the amount of proliferation of $T_{reg}$ cells induced by wild-type IL-2 (such as, the polypeptide encoded by SEQ ID NO: 1). In some embodiments, the $T_{reg}$ cell is a CD4$^+$Foxp3$^+$ cell.

As described in greater detail below, in some embodiments of the disclosure, the IL-2 muteins disclosed herein and nucleic acids encoding such IL-2 muteins can be incorporated into compositions, including pharmaceutical compositions. Such compositions typically include the polypeptide or nucleic acid molecule and a pharmaceutically acceptable carrier.

B. Nucleic Acids

In one aspect, some embodiments disclosed herein relate to nucleic acid molecules encoding the IL-2 mutein the disclosure, including expression cassettes, and expression vectors containing these nucleic acid molecules operably linked to heterologous nucleic acid sequences such as, for example, regulator sequences which allow in vivo expression of the IL-2 mutein in a host cell or ex-vivo cell-free expression system.

In various embodiments, polypeptides used in the practice of the instant disclosure are synthetic, or are produced by expression of a recombinant nucleic acid molecule. In the event the polypeptide is a chimera (e.g., a fusion protein containing at least a mutant IL-2 polypeptide and a heterologous polypeptide), it can be encoded by a hybrid nucleic acid molecule containing one sequence that encodes all or part of the mutant IL-2, and a second sequence that encodes all or part of the heterologous polypeptide. For example, subject IL-2 muteins described herein may be fused to a hexa-histidine tag to facilitate purification of bacterially expressed protein, or to a hemagglutinin tag to facilitate purification of protein expressed in eukaryotic cells.

The terms "nucleic acid molecule" and "polynucleotide" are used interchangeably herein, and refer to both RNA and DNA molecules, including nucleic acid molecules comprising cDNA, genomic DNA, synthetic DNA, and DNA or RNA molecules containing nucleic acid analogs. A nucleic acid molecule can be double-stranded or single-stranded (e.g., a sense strand or an antisense strand). A nucleic acid molecule may contain unconventional or modified nucleotides. The terms "polynucleotide sequence" and "nucleic acid sequence" as used herein interchangeably refer to the sequence of a polynucleotide molecule. The nomenclature for nucleotide bases as set forth in 37 CFR § 1.822 is used herein.

Nucleic acid molecules of the present disclosure can be nucleic acid molecules of any length, including nucleic acid molecules that are preferably between about 0.5 Kb and about 50 Kb, or example between about 0.5 Kb and about 10 Kb, between about 1 Kb and about 8 Kb, between about 2 Kb and about 7 Kb, or between about 2 Kb and about 20 Kb, for example between about 2 Kb to 10 Kb, between about 3 Kb and about 15 Kb, between about 4 Kb and about 10 Kb, about 5 Kb and about 15 Kb, or about 3 Kb and about 9 Kb. In some embodiments, the nucleic acid molecules of the present disclosure can be between 5 Kb to 50 Kb, for example between about 5 Kb and about 40 Kb, between about 5 Kb and about 30 Kb, between about 5 Kb and about 20 Kb, or between about 10 Kb and about 50 Kb, for example between about 15 Kb to 30 Kb, between about 20 Kb and about 50 Kb, between about 20 Kb and about 40 Kb, about 5 Kb and about 25 Kb, or about 30 Kb and about 50 Kb.

Methods for constructing a DNA sequence encoding the IL-2 muteins and expressing those sequences in a suitably transformed host include, but are not limited to, using a PCR-assisted mutagenesis technique. Mutations that consist of deletions or additions of amino acid residues to an IL-2 polypeptide can also be made with standard recombinant techniques. In the event of a deletion or addition, the nucleic acid molecule encoding IL-2 is optionally digested with an appropriate restriction endonuclease. The resulting fragment can either be expressed directly or manipulated further by, for example, ligating it to a second fragment. The ligation may be facilitated if the two ends of the nucleic acid molecules contain complementary nucleotides that overlap one another, but blunt-ended fragments can also be ligated. PCR-generated nucleic acids can also be used to generate various mutant sequences.

The complete amino acid sequence can be used to construct a back-translated gene. A DNA oligomer containing a nucleotide sequence coding for IL-2 mutein can be synthesized. For example, several small oligonucleotides coding for portions of the desired polypeptide can be synthesized and then ligated. The individual oligonucleotides typically contain 5' or 3' overhangs for complementary assembly.

In addition to generating mutant polypeptides via expression of nucleic acid molecules that have been altered by recombinant molecular biological techniques, subject IL-2 muteins can be chemically synthesized. Chemically synthesized polypeptides are routinely generated by those of skill in the art.

Once assembled (by synthesis, site-directed mutagenesis or another method), the DNA sequences encoding an IL-2 mutein will be inserted into an expression vector and operatively linked to an expression control sequence appropriate for expression of the IL-2 mutein in the desired transformed host. Proper assembly can be confirmed by nucleotide sequencing, restriction mapping, and expression of a biologically active polypeptide in a suitable host. As is well known in the art, in order to obtain high expression levels of a transfected gene in a host, the gene must be operatively linked to transcriptional and translational expression control sequences that are functional in the chosen expression host.

The DNA sequence encoding the IL-2 mutein, whether prepared by site directed mutagenesis, chemical synthesis or other methods, can also include DNA sequences that encode a signal sequence. Such signal sequence, if present, should be one recognized by the cell chosen for expression of the IL-2 mutein. It can be prokaryotic, eukaryotic or a combination of the two. It can also be the signal sequence of native IL-2. The inclusion of a signal sequence depends on whether it is desired to secrete the IL-2 mutein from the recombinant cells in which it is made. If the chosen cells are prokaryotic, it generally is preferred that the DNA sequence not encode a signal sequence. If the chosen cells are eukaryotic, it generally is preferred that a signal sequence be encoded and most preferably that the wild-type IL-2 signal sequence be used.

In some embodiments the subject IL-2 mutein, either alone or as a part of a chimeric polypeptide, such as those described above, can be obtained by expression of a nucleic acid molecule. Just as IL-2 muteins can be described in terms of their identity with wild-type IL-2 polypeptides, the nucleic acid molecules encoding them will necessarily have a certain identity with those that encode wild-type IL-2. For example, the nucleic acid molecule encoding a subject IL-2 mutein can be at least 50%, at least 65%, preferably at least 75%, more preferably at least 85%, and most preferably at least 95% (e.g., 99%) identical to the nucleic acid encoding wild-type IL-2. Thus, in some embodiments, the nucleic acid molecule encoding a subject IL-2 mutein disclosed herein is at least 50%, at least 65%, preferably at least 75%, more preferably at least 85%, and most preferably at least 95% (e.g., 96%, 97%, 98%, or 99%) identical to the nucleic acid encoding a wild-type IL-2 having the amino acid set forth in SEQ ID NO: 1. In some embodiments, the nucleic acid molecule encoding a subject IL-2 mutein disclosed herein is at least 50%, at least 65%, preferably at least 75%, more preferably at least 85%, and most preferably at least 95% (e.g., 96%, 97%, 98%, or 99%) identical to the nucleic acid encoding a wild-type IL-2 having the amino acid set forth in SEQ ID NO: 2.

The nucleic acid molecules provided can contain naturally occurring sequences, or sequences that differ from those that occur naturally, but, due to the degeneracy of the genetic code, encode the same polypeptide. These nucleic acid molecules can consist of RNA or DNA (for example, genomic DNA, cDNA, or synthetic DNA, such as that produced by phosphoramidite-based synthesis), or combinations or modifications of the nucleotides within these types of nucleic acids. In addition, the nucleic acid molecules can be double-stranded or single-stranded (i.e., either a sense or an antisense strand).

The nucleic acid molecules are not limited to sequences that encode polypeptides; some or all of the non-coding sequences that lie upstream or downstream from a coding sequence (e.g., the coding sequence of IL-2) can also be included. Those of ordinary skill in the art of molecular biology are familiar with routine procedures for isolating nucleic acid molecules. They can, for example, be generated by treatment of genomic DNA with restriction endonucleases, or by performance of the polymerase chain reaction (PCR). In the event the nucleic acid molecule is a ribonucleic acid (RNA), molecules can be produced, for example, by in vitro transcription.

Exemplary isolated nucleic acid molecules of the present disclosure can include fragments not found as such in the natural state. Thus, this disclosure encompasses recombinant molecules, such as those in which a nucleic acid sequence (for example, a sequence encoding a mutant IL-2) is incorporated into a vector (e.g., a plasmid or viral vector) or into the genome of a heterologous cell (or the genome of a homologous cell, at a position other than the natural chromosomal location).

As described above, the subject IL-2 mutein may exist as a part of a chimeric polypeptide. In addition to, or in place of, the heterologous polypeptides described above, a subject nucleic acid molecule can contain sequences encoding a "marker" or "reporter." Examples of marker or reporter genes include β-lactamase, chloramphenicol acetyltransferase (CAT), adenosine deaminase (ADA), aminoglycoside phosphotransferase (neo$^R$, G418), dihydrofolate reductase (DHFR), hygromycin-B-phosphotransferase (HPH), thymidine kinase (TK), lacz (encoding β-galactosidase), and xanthine guanine phosphoribosyltransferase (XGPRT). One of skill in the art will be aware of additional useful reagents, for example, of additional sequences that can serve the function of a marker or reporter.

The subject nucleic acid molecules can be obtained by introducing a mutation into IL-2-encoding DNA obtained from any biological cell, such as the cell of a mammal. Thus, the subject nucleic acids (and the polypeptides they encode) can be those of a mouse, rat, guinea pig, cow, sheep, horse, pig, rabbit, monkey, baboon, dog, or cat. In some embodiments, the nucleic acid molecules will be those of a human.

C. Vectors and Host Cells

Also provided herein are vectors, plasmids or viruses containing one or more of the nucleic acid molecules encoding any of the IL-2 mutein polypeptides disclosed herein. The nucleic acid molecules described above can be contained within a vector that is capable of directing their expression in, for example, a cell that has been transduced with the vector. Accordingly, in addition to the subject IL-2 muteins, expression vectors containing a nucleic acid molecule encoding a subject IL-2 mutein and cells transfected with these vectors are among the preferred embodiments. Suitable vectors for use in eukaryotic and prokaryotic cells are known in the art and are commercially available or readily prepared by a skilled artisan. Additional vectors can also be found, for example, in Ausubel, F. M., et al., *Current Protocols in Molecular Biology*, (Current Protocol, 1994) and Sambrook et al., "*Molecular Cloning: A Laboratory Manual*," 2nd ED. (1989).

It should of course be understood that not all vectors and expression control sequences will function equally well to express the DNA sequences described herein. Neither will all hosts function equally well with the same expression system. However, one of skill in the art may make a selection among these vectors, expression control sequences and hosts without undue experimentation. For example, in selecting a vector, the host must be considered because the vector must replicate in it. The vector's copy number, the ability to control that copy number, and the expression of any other proteins encoded by the vector, such as antibiotic markers, should also be considered. For example, vectors that can be used include those that allow the DNA encoding the IL-2 muteins to be amplified in copy number. Such amplifiable vectors are well known in the art. They include, for example, vectors able to be amplified by DHFR amplification (see, e.g., Kaufman, U.S. Pat. No. 4,470,461, Kaufman and Sharp, "Construction of a Modular Dihydrafolate Reductase cDNA Gene: Analysis of Signals Utilized for Efficient Expression", Mol. Cell. Biol., 2, pp. 1304-19 (1982)) or glutamine synthetase ("GS") amplification (see, e.g., U.S. Pat. No. 5,122,464 and European published application 338,841).

In some embodiments, the human IL-2 muteins of the present disclosure will be expressed from vectors, preferably expression vectors. The vectors are useful for autonomous replication in a host cell or may be integrated into the genome of a host cell upon introduction into the host cell, and thereby are replicated along with the host genome (e.g., non-episomal mammalian vectors). Expression vectors are capable of directing the expression of coding sequences to which they are operably linked. In general, expression vectors of utility in recombinant DNA techniques are often in the form of plasmids (vectors). However, other forms of expression vectors, such as viral vectors (e.g., replication defective retroviruses, adenoviruses, and adeno-associated viruses) are included also.

Exemplary recombinant expression vectors can include one or more regulatory sequences, selected on the basis of the host cells to be used for expression, operably linked to the nucleic acid sequence to be expressed.

The expression constructs or vectors can be designed for expression of an IL-2 mutein or variant thereof in prokaryotic or eukaryotic host cells.

Vector DNA can be introduced into prokaryotic or eukaryotic cells via conventional transformation or transfection techniques. Suitable methods for transforming or transfecting host cells can be found in Sambrook et al. (1989) Molecular Cloning: A Laboratory Manual (2nd ed., Cold Spring Harbor Laboratory Press, Plainview, N.Y.) and other standard molecular biology laboratory manuals.

Expression of proteins in prokaryotes is most often carried out in *Escherichia coli* with vectors containing constitutive or inducible promoters. Strategies to maximize recombinant protein expression in *E. coli* can be found, for example, in Gottesman (1990) in *Gene Expression Technology: Methods in Enzymology* Vol. 185 (Academic Press, San Diego, Calif.), pp. 119-128 and Wada et al. (1992) Nucleic Acids Res. 20:2111-2118. Processes for growing, harvesting, disrupting, or extracting the IL-2 mutein or variant thereof from cells are substantially described in, for example, U.S. Pat. Nos. 4,604,377; 4,738,927; 4,656,132; 4,569,790; 4,748,234; 4,530,787; 4,572,798; 4,748,234; and 4,931,543, herein incorporated by reference in their entireties.

In some embodiments the recombinant IL-2 muteins or biologically active variants thereof can also be made in eukaryotes, such as yeast or human cells. Suitable eukaryotic host cells include insect cells (examples of Baculovirus vectors available for expression of proteins in cultured insect cells (e.g., Sf9 cells) include the pAc series (Smith et al. (1983) Mol. Cell Biol. 3:2156-2165) and the pVL series (Lucklow and Summers (1989) Virology 170:31-39)); yeast cells (examples of vectors for expression in yeast *S. cerevisiae* include pYepSec1 (Baldari et al. (1987) *EMBO J.* 6:229-234), pMFa (Kurjan and Herskowitz (1982) Cell 30:933-943), pJRY88 (Schultz et al. (1987) Gene 54:113-123), pYES2 (Invitrogen Corporation, San Diego, Calif.), and pPicZ (Invitrogen Corporation, San Diego, Calif.)); or mammalian cells (mammalian expression vectors include pCDM8 (Seed (1987) Nature 329:840) and pMT2PC (Kaufman et al. (1987) EMBO J. 6:187:195)). Suitable mammalian cells include Chinese hamster ovary cells (CHO) or COS cells. In mammalian cells, the expression vector's control functions are often provided by viral regulatory elements. For example, commonly used promoters are derived from polyoma, Adenovirus 2, cytomegalovirus, and Simian Virus 40. For other suitable expression systems for both prokaryotic and eukaryotic cells, see Chapters 16 and 17 of Sambrook et al. (1989) *Molecular Cloning: A Laboratory Manual* (2nd ed., Cold Spring Harbor Laboratory Press, Plainview, N.Y.). See, Goeddel (1990, supra).

The sequences encoding the human IL-2 muteins of the present disclosure can be optimized for expression in the host cell of interest. The G-C content of the sequence can be adjusted to levels average for a given cellular host, as calculated by reference to known genes expressed in the host cell. Methods for codon optimization are well known in the art. Codons within the IL-2 mutein coding sequence can be optimized to enhance expression in the host cell, such that about 1%, about 5%, about 10%, about 25%, about 50%, about 75%, or up to 100% of the codons within the coding sequence have been optimized for expression in a particular host cell.

Vectors suitable for use include T7-based vectors for use in bacteria (see, for example, Rosenberg et al., Gene 56:125, 1987), the pMSXND expression vector for use in mammalian cells (Lee and Nathans, J. Biol. Chem. 263:3521, 1988), and baculovirus-derived vectors (for example, the expression vector pBacPAK9 from Clontech, Palo Alto, Calif.) for use in insect cells.

In some embodiments nucleic acid inserts, which encode the subject IL-2 muteins in such vectors, can be operably linked to a promoter, which is selected based on, for example, the cell type in which expression is sought.

In selecting an expression control sequence, a variety of factors should also be considered. These include, for example, the relative strength of the sequence, its controllability, and its compatibility with the actual DNA sequence encoding the subject IL-2 mutein, particularly as regards potential secondary structures. Hosts should be selected by consideration of their compatibility with the chosen vector, the toxicity of the product coded for by the DNA sequences of this disclosure, their secretion characteristics, their ability to fold the polypeptides correctly, their fermentation or culture requirements, and the ease of purification of the products coded for by the DNA sequences.

Within these parameters one of skill in the art may select various vector/expression control sequence/host combinations that will express the desired DNA sequences on fermentation or in large scale animal culture, for example, using CHO cells or COS 7 cells.

The choice of expression control sequence and expression vector, in some embodiments, will depend upon the choice of host. A wide variety of expression host/vector combinations can be employed. Useful expression vectors for eukaryotic hosts, include, for example, vectors with expression control sequences from SV40, bovine papilloma virus, adenovirus and cytomegalovirus. Useful expression vectors for bacterial hosts include known bacterial plasmids, such as plasmids from *E. coli*, including col E1, pCRI, pER32z, pMB9 and their derivatives, wider host range plasmids, such as RP4, phage DNAs, e.g., the numerous derivatives of phage lambda, e.g., NM989, and other DNA phages, such as M13 and filamentous single stranded DNA phages. Useful expression vectors for yeast cells include the 2μ plasmid and derivatives thereof. Useful vectors for insect cells include pVL 941 and pFastBac™ 1 (Gibco BRL, Gaithersburg, Md.). Cate et al., Cell, 45, pp. 685-98 (1986).

In addition, any of a wide variety of expression control sequences can be used in these vectors. Such useful expression control sequences include the expression control sequences associated with structural genes of the foregoing expression vectors. Examples of useful expression control sequences include, for example, the early and late promoters of SV40 or adenovirus, the lac system, the trp system, the TAC or TRC system, the major operator and promoter regions of phage lambda, for example PL, the control regions of fd coat protein, the promoter for 3-phosphoglycerate kinase or other glycolytic enzymes, the promoters of acid phosphatase, e.g., PhoA, the promoters of the yeast a-mating system, the polyhedron promoter of Baculovirus, and other sequences known to control the expression of genes of prokaryotic or eukaryotic cells or their viruses, and various combinations thereof.

A T7 promoter can be used in bacteria, a polyhedrin promoter can be used in insect cells, and a cytomegalovirus or metallothionein promoter can be used in mammalian cells. Also, in the case of higher eukaryotes, tissue-specific and cell type-specific promoters are widely available. These promoters are so named for their ability to direct expression of a nucleic acid molecule in a given tissue or cell type within the body. Skilled artisans are well aware of numerous promoters and other regulatory elements which can be used to direct expression of nucleic acids.

In addition to sequences that facilitate transcription of the inserted nucleic acid molecule, vectors can contain origins of replication, and other genes that encode a selectable marker. For example, the neomycin-resistance (neoR) gene imparts G418 resistance to cells in which it is expressed, and thus permits phenotypic selection of the transfected cells. Those of skill in the art can readily determine whether a given regulatory element or selectable marker is suitable for use in a particular experimental context.

Viral vectors that can be used in the disclosure include, for example, retroviral, adenoviral, and adeno-associated vectors, herpes virus, simian virus 40 (SV40), and bovine papilloma virus vectors (see, for example, Gluzman (Ed.), *Eukaryotic Viral Vectors*, CSH Laboratory Press, Cold Spring Harbor, N.Y.).

Prokaryotic or eukaryotic cells that contain and express a nucleic acid molecule that encodes a subject IL-2 mutein disclosed herein are also features of the disclosure. A cell of the disclosure is a transfected cell, i.e., a cell into which a nucleic acid molecule, for example a nucleic acid molecule encoding a mutant IL-2 polypeptide, has been introduced by means of recombinant DNA techniques. The progeny of such a cell are also considered within the scope of the disclosure.

The precise components of the expression system are not critical. For example, an IL-2 mutein can be produced in a prokaryotic host, such as the bacterium *E. coli*, or in a eukaryotic host, such as an insect cell (e.g., an Sf21 cell), or mammalian cells (e.g., COS cells, NIH 3T3 cells, or Hela cells). These cells are available from many sources, including the American Type Culture Collection (Manassas, Va.). In selecting an expression system, it matters only that the components are compatible with one another. Artisans or ordinary skill are able to make such a determination. Furthermore, if guidance is required in selecting an expression system, skilled artisans may consult Ausubel et al. (Current Protocols in Molecular Biology, John Wiley and Sons, New York, N.Y., 1993) and Pouwels et al. (*Cloning Vectors: A Laboratory Manual*, 1985 Suppl. 1987).

The expressed polypeptides can be purified from the expression system using routine biochemical procedures, and can be used, e.g., as therapeutic agents, as described herein.

In some embodiments, IL-2 muteins obtained will be glycosylated or unglycosylated depending on the host organism used to produce the mutein. If bacteria are chosen as the host then the IL-2 mutein produced will be unglycosylated. Eukaryotic cells, on the other hand, will glycosylate the IL-2 muteins, although perhaps not in the same way as native-IL-2 is glycosylated. The IL-2 mutein produced by the transformed host can be purified according to any suitable method. Various methods are known for purifying IL-2. See, e.g. *Current Protocols in Protein Science*, Vol 2. Eds: John E. Coligan, Ben M. Dunn, Hidde L. Ploehg, David W. Speicher, Paul T. Wingfield, Unit 6.5 (Copyright 1997, John Wiley and Sons, Inc. IL-2 muteins can be isolated from inclusion bodies generated in *E. coli*, or from conditioned medium from either mammalian or yeast cultures producing a given mutein using cation exchange, gel filtration, and or reverse phase liquid chromatography.

Another exemplary method of constructing a DNA sequence encoding the IL-2 muteins is by chemical synthesis. This includes direct synthesis of a peptide by chemical means of the protein sequence encoding for an IL-2 mutein exhibiting the properties described. This method can incorporate both natural and unnatural amino acids at positions that affect the interactions of IL-2 with the IL-2Rα, the IL-2Rβ and/or the IL-2Rγ. Alternatively, a gene which encodes the desired IL-2 mutein can be synthesized by chemical means using an oligonucleotide synthesizer. Such oligonucleotides are designed based on the amino acid sequence of the desired IL-2 mutein, and preferably selecting those codons that are favored in the host cell in which the recombinant mutein will be produced. In this regard, it is well recognized that the genetic code is degenerate—that an amino acid may be coded for by more than one codon. For example, Phe (F) is coded for by two codons, TIC or TTT, Tyr (Y) is coded for by TAC or TAT and his (H) is coded for by CAC or CAT. Trp (W) is coded for by a single codon, TGG. Accordingly, it will be appreciated that for a given DNA sequence encoding a particular IL-2 mutein, there will be many DNA degenerate sequences that will code for that IL-2 mutein. For example, it will be appreciated that in addition to the preferred DNA sequence for mutein 5-2 shown in FIG. 2, there will be many degenerate DNA sequences that code for the IL-2 mutein shown. These degenerate DNA sequences are considered within the scope of this disclosure. Therefore, "degenerate variants thereof in the context of this disclosure means all DNA sequences that code for and thereby enable expression of a particular mutein.

The biological activity of the IL-2 muteins can be assayed by any suitable method known in the art. Such assays include PHA-blast proliferation and NK cell proliferation.

D. Fusion Proteins

Any of the IL-2 muteins disclosed herein can be prepared as fusion or chimeric polypeptides that include a subject IL-2 muteins and a heterologous polypeptide (i.e., a polypeptide that is not IL-2 or a mutant thereof) (see, e.g., U.S. Pat. No. 6,451,308). Exemplary heterologous polypeptides can increase the circulating half-life of the chimeric polypeptide in vivo, and may, therefore, further enhance the properties of the mutant IL-2 polypeptides. In various embodiments, the polypeptide that increases the circulating half-life may be a serum albumin, such as human serum albumin, or the Fc region of the IgG subclass of antibodies that lacks the IgG heavy chain variable region. Exemplary Fc regions can include a mutation that inhibits complement fixation and Fc receptor binding, or it may be lytic, i.e., able to bind complement or to lyse cells via another mechanism, such as antibody-dependent complement lysis (ADCC; U.S. Ser. No. 08/355,502 filed Dec. 12, 1994).

The "Fc region" can be a naturally occurring or synthetic polypeptide that is homologous to the IgG C-terminal domain produced by digestion of IgG with papain. IgG Fc has a molecular weight of approximately 50 kDa. The mutant IL-2 polypeptides can include the entire Fc region, or a smaller portion that retains the ability to extend the circulating half-life of a chimeric polypeptide of which it is a part. In addition, full-length or fragmented Fc regions can be variants of the wild-type molecule. That is, they can contain mutations that may or may not affect the function of the polypeptides; as described further below, native activity is not necessary or desired in all cases. In some embodiments, the IL-2 mutein fusion protein (e.g., an IL-2 partial agonist or antagonist as described herein) includes an IgG1, IgG2, IgG3, or IgG4 Fc region.

The Fc region can be "lytic" or "non-lytic," but is typically non-lytic. A non-lytic Fc region typically lacks a high affinity Fc receptor binding site and a C'1q binding site. The high affinity Fc receptor binding site of murine IgG Fc includes the Leu residue at position 235 of IgG Fc. Thus, the Fc receptor binding site can be destroyed by mutating or deleting Leu 235. For example, substitution of Glu for Leu 235 inhibits the ability of the Fc region to bind the high affinity Fc receptor. The murine C'1q binding site can be functionally destroyed by mutating or deleting the Glu 318, Lys 320, and Lys 322 residues of IgG. For example, substitution of Ala residues for Glu 318, Lys 320, and Lys 322 renders IgG1 Fc unable to direct antibody-dependent complement lysis. In contrast, a lytic IgG Fc region has a high affinity Fe receptor binding site and a C'1q binding site. The high affinity Fc receptor binding site includes the Leu residue at position 235 of IgG Fc, and the C'1q binding site includes the Glu 318, Lys 320, and Lys 322 residues of IgG1. Lytic IgG Fc has wild-type residues or conservative amino acid substitutions at these sites. Lytic IgG Fc can target cells for antibody dependent cellular cytotoxicity or complement directed cytolysis (CDC). Appropriate mutations for human IgG are also known (see, e.g., Morrison et al., *The Immunologist* 2:119-124, 1994; and Brekke et al., *The Immunologist* 2: 125, 1994).

In other embodiments, the chimeric polypeptide can include a subject IL-2 mutein and a polypeptide that functions as an antigenic tag, such as a FLAG sequence. FLAG sequences are recognized by biotinylated, highly specific, anti-FLAG antibodies, as described herein (see also Blanar et al., *Science* 256:1014, 1992; LeClair et al., *Proc. Natl. Acad. Sci. USA* 89:8145, 1992). In some embodiments, the chimeric polypeptide further includes a C-terminal c-myc epitope tag.

In other embodiments, the chimeric polypeptide includes the mutant IL-2 polypeptide and a heterologous polypeptide that functions to enhance expression or direct cellular localization of the mutant IL-2 polypeptide, such as the Aga2p agglutinin subunit (see, e.g., Boder and Wittrup, *Nature Biotechnol.* 15:553-7, 1997).

In other embodiments, a chimeric polypeptide including a mutant IL-2 and an antibody or antigen-binding portion thereof can be generated. The antibody or antigen-binding component of the chimeric protein can serve as a targeting moiety. For example, it can be used to localize the chimeric protein to a particular subset of cells or target molecule. Methods of generating cytokine-antibody chimeric polypeptides are described, for example, in U.S. Pat. No. 6,617,135.

In some embodiments, the mutant IL-2 can be modified with one or more polyethylene glycol (PEG) molecules to increase its half-life. The term "PEG" as used herein means a polyethylene glycol molecule. In its typical form, PEG is a linear polymer with terminal hydroxyl groups and has the formula $HO-CH_2CH_2-(CH_2CH_2O)n-CH_2CH_2-OH$, where n is from about 8 to about 4000.

Typically, n is not a discrete value but constitutes a range with approximately Gaussian distribution around an average value. The terminal hydrogen may be substituted with a capping group such as an alkyl or alkanol group. PEG can have at least one hydroxy group, more preferably it is a terminal hydroxy group. This hydroxy group is can be attached to a linker moiety which can react with the peptide to form a covalent linkage. Numerous derivatives of PEG exist in the art. (See, e.g., U.S. Pat. Nos. 5,445,090; 5,900,461; 5,932,462; 6,436,386; 6,448,369; 6,437,025; 6,448,369; 6,495,659; 6,515,100 and 6,514,491 and Zalipsky, S. *Bioconjugate Chem.* 6: 150-165, 1995). The PEG molecule covalently attached to the IL-2 muteins of the present disclosure may be approximately 10,000, 20,000, 30,000, or 40,000 daltons average molecular weight. PEGylation reagents may be linear or branched molecules and may be present singularly or in tandem. The PEGylated IL-2 mutein peptides of the present disclosure can have tandem PEG molecules attached to the C-terminus and/or the N-terminus of the peptide. The term "PEGylation" as used herein means the covalent attachment of one or more PEG molecules, as described above, to a molecule such as the IL-2 muteins of the present disclosure.

E. Pharmaceutical Compositions

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™. (BASF, Parsippany, N.J.) or phosphate buffered saline (PBS). In all cases, the composition should be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants, e.g., sodium dodecyl sulfate. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions, if used, generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel™, or corn starch; a lubricant such as magnesium stearate or Sterotes™; a glidant such as colloidal silicon dioxide; a sweetening agent such as sucrose or saccharin; or a flavoring agent such as peppermint, methyl salicylate, or orange flavoring.

In the event of administration by inhalation, subject IL-2 muteins, or the nucleic acids encoding them, are delivered in the form of an aerosol spray from pressured container or dispenser which contains a suitable propellant, e.g., a gas such as carbon dioxide, or a nebulizer. Such methods include those described in U.S. Pat. No. 6,468,798.

Systemic administration of the subject IL-2 muteins or nucleic acids can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In some embodiments, compounds (mutant IL-2 polypeptides or nucleic acids) can also be prepared in the form of suppositories (e.g., with conventional suppository bases such as cocoa butter and other glycerides) or retention enemas for rectal delivery.

In some embodiments, compounds (subject IL-2 muteins or nucleic acids) can also be administered by transfection or infection using methods known in the art, including but not limited to the methods described in McCaffrey et al. (Nature 418:6893, 2002), Xia et al. (*Nature Biotechnol.* 20: 1006-1010, 2002), or Putnam (*Am. J. Health Syst. Pharm.* 53: 151-160, 1996, erratum at *Am. J. Health Syst. Pharm.* 53:325, 1996).

In some embodiments, the subject IL-2 muteins or nucleic acids are prepared with carriers that will protect the mutant IL-2 polypeptides against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

IV. Methods of the Disclosure

Some aspects of the disclosure relate to methods and related materials useful for producing the IL-2 muteins, e.g., the IL-2 partial agonists described herein, as well as methods for the treatment of health conditions and disorders associated with perturbations of signal transduction mediated by IL-2 signaling pathway. More particularly, some embodiments of the disclosure relate to modulating signal transduction pathway mediated by interleukin 2 (IL-2) in a subject in need thereof. In some embodiments of the disclosure, IL-2 mediated signaling is modulated via selective reduction of IL-2 binding to one, two, or three of its receptors, e.g., interleukin 2 alpha receptor (IL-2Rα), interleukin 2 beta receptor (IL-2Rβ), interleukin-2 gamma receptor (IL-2Rγ).

In one aspect, some embodiments of the disclosure relate to compositions and methods useful for producing the IL-2 mutein disclosed herein, the method includes culturing the host cell as described herein under suitable conditions for the production of the IL-2 muteins.

In some embodiments, the method further includes isolation of the produced mutein. In some embodiments, the method further includes purification of the produced mutein. Techniques, systems, and related materials suitable for isolation and purification of proteins recombinant produced in prokaryotic and eukaryotic host cells are known in the art.

In some embodiments, the produced IL-2 muteins can be further modified to prolong their half-life in vivo and/or ex vivo. Non-limiting examples of known strategies and methodologies suitable for modifying the IL-2 muteins of the disclosure include (1) chemical modification of a IL-2 mutein polypeptide described herein with highly soluble macromolecules such as polyethylene glycol ("PEG") which prevents the polypeptides from contacting with proteases; (2) covalently linking or conjugating a IL-2 mutein described herein with antibody or antibody fragment such as, for example, a human Fc antibody fragment; and (3) covalently linking or conjugating a IL-2 mutein described herein with a stable protein such as, for example, albumin. Accordingly, in some embodiments, the IL-2 muteins of the disclosure can be fused to a stable protein, such as, albumin. For example, human albumin is known as one of the most effective proteins for enhancing the stability of polypeptides fused thereto and there are many such fusion proteins reported.

In some embodiments, the produced IL-2 muteins of the disclosure are chemically modified with one or more polyethylene glycol moieties, e.g., PEGylated; or with similar modifications, e.g. PASylated. In some embodiments, the PEG molecule or PAS molecule is conjugated to one or more amino acids of the IL-2 mutein. In some embodiments, the PEGylated or PASylated IL-2 mutein contains a PEG or PAS moiety on only one amino acid. In other embodiments, the PEGylated or PASylated IL-2 mutein contains a PEG or PAS moiety on two or more amino acids, e.g., attached to two or more, five or more, ten or more, fifteen or more, or twenty or more different amino acid residues. In some embodiments, the PEG or PAS chain is 2000, greater than 2000, 5000, greater than 5,000, 10,000, greater than 10,000, greater than 10,000, 20,000, greater than 20,000, and 30,000 Da. The produced IL-2 mutein may be coupled directly to PEG or PAS (e.g., without a linking group) through an amino group, a sulfhydryl group, a hydroxyl group, or a carboxyl group.

In one aspect, some embodiments of the disclosure relate to compositions and methods useful for the treatment of health conditions and disorders associated with perturbations of signal transduction mediated by IL-2 signaling pathway. More particularly, some embodiments of the disclosure relate to modulating signal transduction pathway mediated by interleukin 2 (IL-2) in a subject in need thereof.

In some embodiments, the IL-2 muteins of the disclosure, and/or nucleic acids expressing them scan be administered to a subject to treat a disorder associated with unwanted autoimmune or immunosuppressive responses. In the treatment of such diseases, the IL-2 muteins disclosed herein may possess advantageous properties, such as stimulating regulatory T cells while at the same time minimally activating or not activating potentially inflammatory immune cells.

In some embodiments, the IL-2 muteins of the disclosure can be used to treat patients who have, who are suspected of having, or who may be at high risk for developing an autoimmune disease. The method including administering a therapeutically effective amount of (i) any one of the IL-2 muteins disclosed herein, (ii) any one of the nucleic acids or vectors disclosed herein, and/or (iii) any one of the pharmaceutical compositions disclosed herein to the individual. In some embodiments, the autoimmune disease is selected from the group consisting of rheumatoid arthritis, insulin-dependent diabetes mellitus, hemolytic anemias, rheumatic fever, thyroiditis, Crohn's disease, myasthenia gravis, glomerulonephritis, autoimmune hepatitis, multiple sclerosis, alopecia areata, psoriasis, vitiligo, dystrophic epidermolysis bullosa, systemic lupus erythematosus, and graft vs. host disease. In some embodiments, the autoimmune disease is graft vs. host disease.

In some embodiments, the IL-2 muteins, nucleic acids or vectors, and/or pharmaceutical compositions are administered to the subject as a single therapeutic agent or in combination with one or more additional therapeutic agents. In some embodiments, the one or more additional therapeutic agents includes an antibody that targets the mutein to a specific cell type. In some embodiments, the cell type is a regulatory T ($T_{reg}$) cell. In some embodiments, the antibody is covalently or non-covalently linked to the IL-2 mutein.

In one aspect, also provided herein are methods for preventing the proliferation of potentially inflammatory T cells and/or preventing secretion of IFNγ from CD8+ T cells or other inflammatory immune cell subsets, the methods including contacting a cell expressing an interleukin 2 receptor γ (IL-2Rγ) with any of the IL-2 muteins disclosed herein. In other embodiments, the potentially inflammatory T cells are $CD4^+CD44^+IFN\gamma^+$ T cells or are $CD8^+CD44^+IFN\gamma^+$ T cells. In some embodiments, the method is performed in vitro, in vivo, or ex vivo.

As discussed above, in some embodiments, the IL-2 mutein is structurally modified to increase half-life. In some embodiments of any of the embodiments disclosed herein, the modification is one or more modifications selected from the group consisting of fusion to a human Fc antibody fragment, fusion to albumin, and PEGylation.

In another aspect, provided herein are methods for decreasing proliferation of regulatory T ($T_{reg}$) cells including contacting a $T_{reg}$ cell with an interleukin 2 (IL-2) mutein having: (i) reduced binding affinity for interleukin 2 receptor γ (IL-2Rγ) as compared to the polypeptide encoded by SEQ ID NO: 2; and (ii) 0-50% $E_{max}$ as compared to the polypeptide encoded by SEQ ID NO: 2. In some embodiments, the IL-2 mutein includes: (i) one or more amino acid substitutions that increase IL-2Rβ binding affinity compared to the polypeptide encoded by SEQ ID NO: 1, selected from L80F, R81D, L85V, I86V, and I92F, numbered in accordance with the amino acid sequence of SEQ ID NO: 1; and (ii) one or more amino acid substitutions that reduce IL-2Rγ receptor binding affinity and results in 0-50% of the $E_{max}$ compared to the polypeptide encoded by SEQ ID NO: 2, selected from (A) L18R and Q22E; and (B) the amino acid position 126, numbered in accordance with the amino acid sequence of SEQ ID NO: 2.

In another aspect, provided herein are methods for decreasing proliferation of regulatory T ($T_{reg}$) cells including contacting a $T_{reg}$ cell with an IL-2 mutein having: (i) reduced binding affinity for IL-2Rγ as compared to the polypeptide encoded by SEQ ID NO: 1; and (ii) 0-50% $E_{max}$ as compared to the polypeptide encoded by SEQ ID NO: 1. In some embodiments, the Il-2 mutein includes one or more amino acid substitutions that reduce IL-2Rγ receptor binding affinity and results in 0-50% $E_{max}$ as compared to a polypeptide encoded by SEQ ID NO: 1, selected from (A) L18R and Q22E; and (B) amino acid position 126, numbered in accordance with the amino acid sequence of SEQ ID NO: 1. In some embodiments, the amino acid substitution at position 126 of SEQ ID NO: 1 or SEQ ID NO: 2 is selected from the group consisting of Q126A, Q126C, Q126D, Q126E, Q126G, Q126H, Q126I, Q126K, Q126M, Q126R, Q126S, or Q126T. In some embodiments, the Il-2 mutein includes the amino acid substitution Q126H, Q126K, or Q126M. In some embodiments, the Il-2 mutein includes an amino acid substitution Q126H. In some embodiments of any of the embodiments disclosed herein, the method further includes administering the IL2 muteins with an antibody that targets the mutein to a $T_{reg}$ cell. In some embodiments of any of the embodiments disclosed herein, the antibody is covalently or non-covalently linked to the mutein. In some embodiments of any of the embodiments disclosed herein, the method is performed in vitro, in vivo, or ex vivo.

A pharmaceutical composition is formulated to be compatible with its intended route of administration. The terms "administration" and "administering", as used herein, refer to the delivery of a bioactive composition or formulation by an administration route comprising, but not limited to, oral, intravenous, intra-arterial, intramuscular, intraperitoneal, subcutaneous, intramuscular, and topical administration, or combinations thereof. The term includes, but is not limited to, administering by a medical professional and self-administering. In some embodiments, the mutant IL-2 polypeptides of the disclosure may be given orally or by inhalation, but it is more likely that they will be administered through a parenteral route. Examples of parenteral routes of administration include, for example, intravenous, intradermal, subcutaneous, transdermal (topical), transmucosal, and rectal administration. Solutions or suspensions used for parenteral application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as mono- and/or di-basic sodium phosphate, hydrochloric acid or sodium hydroxide (e.g., to a pH of about 7.2-7.8, e.g., 7.5). The parenteral preparation can be enclosed in ampoules, disposable syringes or multiple dose vials made of glass or plastic.

Dosage, toxicity and therapeutic efficacy of such subject IL-2 muteins or nucleic acids compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the disclosure, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a "therapeutically effective amount" of a subject IL-2 mutein (i.e., an effective dosage) depends on the polypeptide selected. For instance, single dose amounts in the range of approximately 0.001 to 0.1 mg/kg of patient body weight can be administered; in some embodiments, about 0.005, 0.01, 0.05 mg/kg may be administered. In some embodiments, 600,000 IU/kg is administered (IU can be determined by a lymphocyte proliferation bioassay and is expressed in International Units (IU) as established by the World Health Organization 1st International Standard for Interleukin-2 (human)). The dosage may be similar to, but is expected to be less than, that prescribed for PROLEUKIN®. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the subject IL-2 muteins can include a single treatment or, can include a series of treatments. In some embodiments, the compositions are administered every 8 hours for five days, followed by a rest period of 2 to 14 days, e.g., 9 days, followed by an additional five days of administration every 8 hours.

Also provided herein are methods for preventing, reducing, or not promoting the proliferation of potentially inflammatory T cells and/or preventing secretion of IFNγ from CD8$^+$ T cells or other inflammatory immune cell subsets. The method is performed by contacting a cell expressing an interleukin 2 receptor γ (IL-2Rγ) with any of the IL-2 muteins disclosed herein. Proliferation of the potentially inflammatory T cells and/or preventing secretion of IFNγ from CD8$^+$ T cells or other inflammatory immune cell subsets can be decreased by any of about 1%, 5%, 10%, 15%, 20%, 25%, 30%, 35%, 40%, 45%, 50%, 55%, 60%, 65%, 70%, 75%, 80%, 85%, 90%, 95%, or 100% (inclusive of values in between these percentages) compared to the proliferation and/or secretion of IFNγ that wild-type IL-2 stimulates at comparable concentrations and under similar conditions. In some embodiments, the potentially inflammatory T cells are CD4$^+$CD44$^+$IFNγ$^+$ T cells or are CD8$^+$CD44$^+$IFNγ$^+$ T cells. The method can additionally be performed in vitro, in vivo, or ex vivo.

V. Systems and Kits

Systems and/or kits of the present disclosure include one or more of any of the IL-2 muteins, nucleic acids, vectors, or pharmaceutical compositions disclosed herein as well as syringes (including pre-filled syringes) and/or catheters (including pre-filled syringes) used to administer any of the IL-2 muteins, nucleic acids, vectors, or pharmaceutical compositions to an individual. The kits also include written instructions for using of any of the IL-2 muteins, nucleic acids, vectors, or pharmaceutical compositions disclosed herein as well as syringes and/or catheters for use with their administration.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

All publications and patent applications mentioned in this disclosure are herein incorporated by reference to the same extent as if each individual publication or patent application was specifically and individually indicated to be incorporated by reference.

No admission is made that any reference cited herein constitutes prior art. The discussion of the references states what their authors assert, and the inventors reserve the right to challenge the accuracy and pertinence of the cited documents. It will be clearly understood that, although a number of information sources, including scientific journal articles, patent documents, and textbooks, are referred to herein; this reference does not constitute an admission that any of these documents forms part of the common general knowledge in the art.

The discussion of the general methods given herein is intended for illustrative purposes only. Other alternative methods and alternatives will be apparent to those of skill in the art upon review of this disclosure, and are to be included within the spirit and purview of this application.

EXAMPLES

Example 1

This Example shows the ability of various human IL-2 variants to stimulate the phosphorylation of STAT5. Human NK-like YT cells were stimulated for 15 min with various human IL-2 variants fused to mouse serum albumin (MSA) at different concentrations as indicated on the graph depicted in FIG. 3 (from 1 µM to 0 µM, 10-fold dilution). All IL-2 variants were purified from transduced HEK 293 cells except IL-2 REK (SEQ ID NO: 10) which was purified from insect cells. The Y axis on the graph depicted in FIG. 3 shows the ratio of p-STAT5 signal from each IL-2 variant normalized to p-STAT5 signal from WT IL-2 for each concentration. As shown, the substitution of residue Q126 by specific amino acids in IL-2 H9 (SEQ ID NO: 2) background results in a wide range of IL-2 efficacies.

Figure 4B:
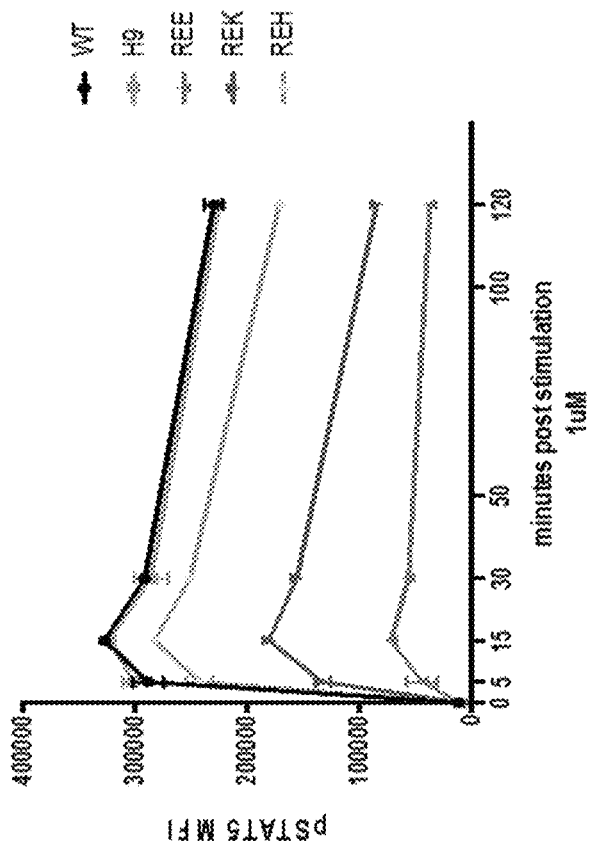
FIG. 4A-B depict the time course for the phospho-STAT5 signaling assay.
Figure 4A:
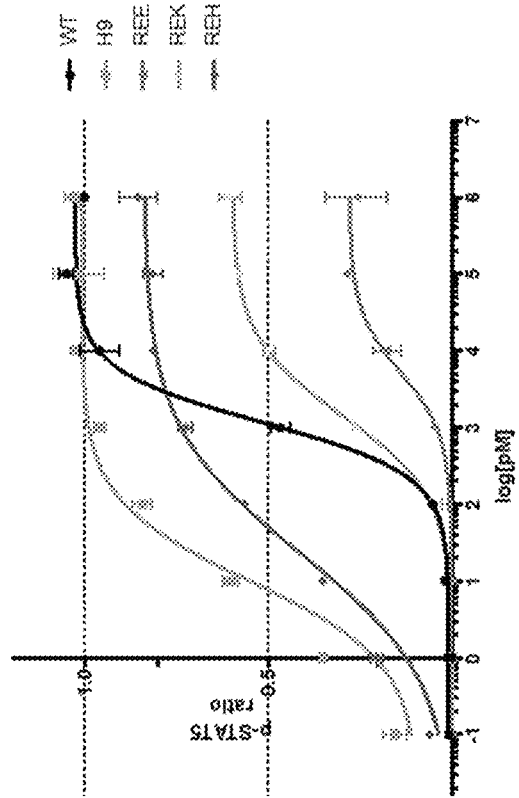

Next, a time course phospho-STAT5 signaling assay was performed by stimulating YT cells for 15 min with the concentration of IL-2 partial agonists indicated on the graph depicted in FIG. 4A. The Y axis of the graph in FIG. 4A shows the ratio of p-STAT5 signal from each IL-2 variant normalized to p-STAT5 signal from WT IL-2 for each concentration. As shown in FIG. 4B, YT cells were stimulated at various time points with 1 µM of different IL-2 variants as indicated on the graph. In this figure, the Y axis indicates the median fluorescence intensity (MFI) for p-STAT5 signal.

This data in FIG. 4B demonstrates that the magnitude of p-STAT5 signal for WT (SEQ ID NO: 1), H9 (SEQ ID NO: 2) and new partial agonists REE (SEQ ID NO: 6), REH (SEQ ID NO: 8) and REK (SEQ ID NO: 10) (all on H9 background) are constant over time with REE, REK and REH signaling at 25%, 50% and 75% respectively.

Example 2

Figure 5A:
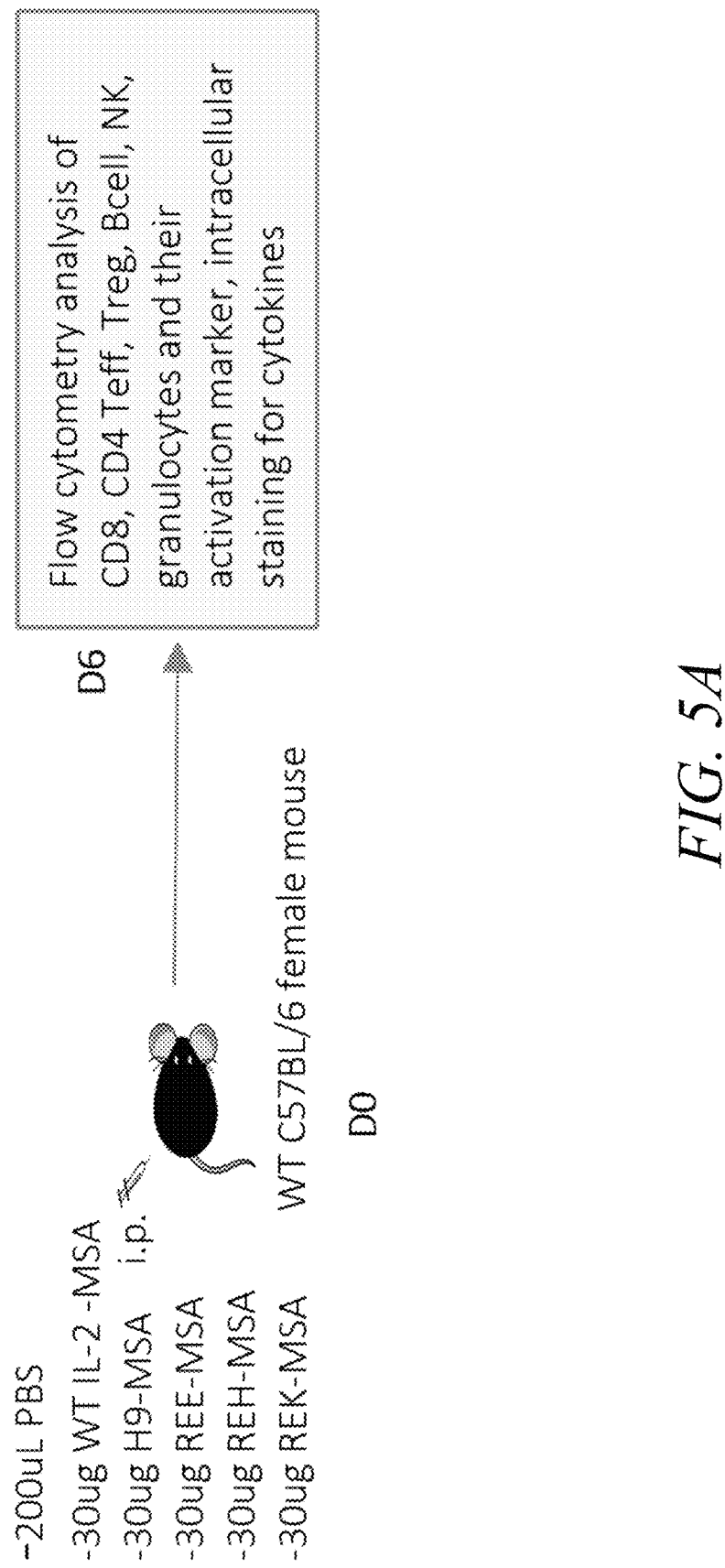
FIG. 5A depicts the experimental protocol for administration of IL2 agonists in mice.
Figure 5B:
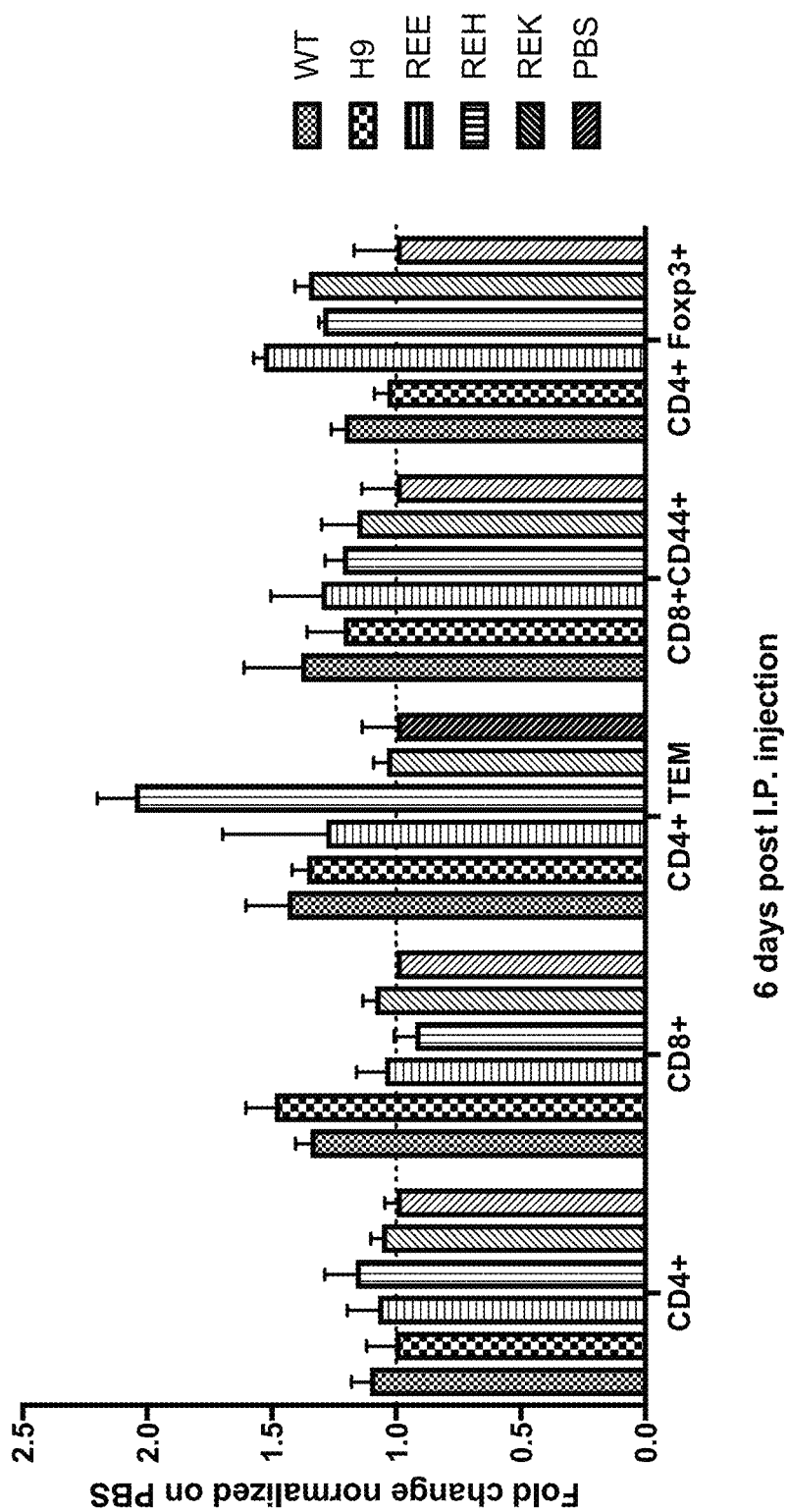
FIG. 5B, FIG. 5C, and FIG. 5D depict the frequency of the indicated immune cell subset for each condition normalized to the respective frequency in PBS-treated mice. B cells were defined by cells gated on CD3$^-$CD19$^+$. NK cells were gated on CD3$^-$NK1.1$^+$. Cells gated on Ly6g (Gr1)$^+$CD3$^+$CD11b$^+$ were defined as granulocytes.
Figure 5C:
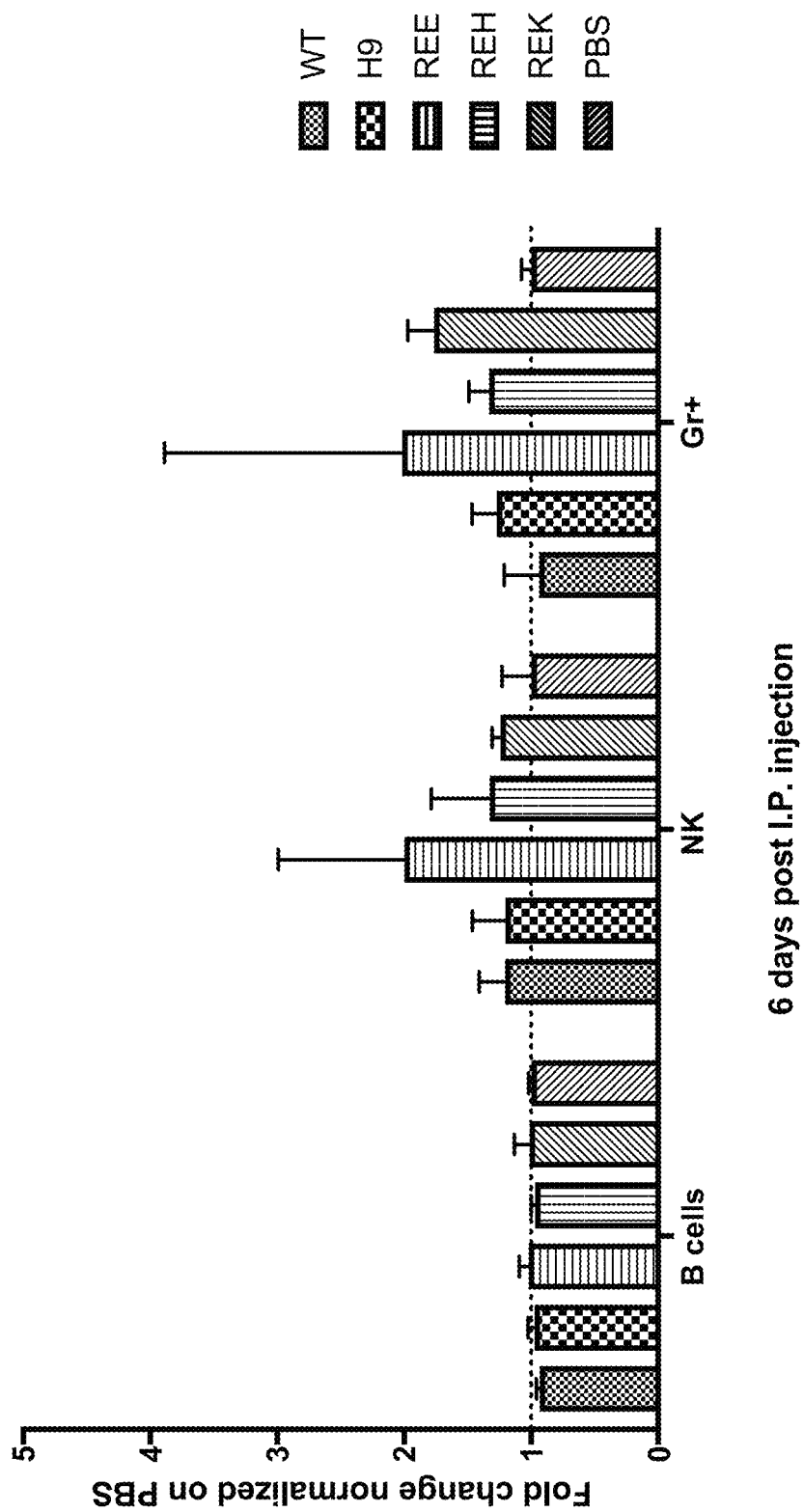
Figure 5D:
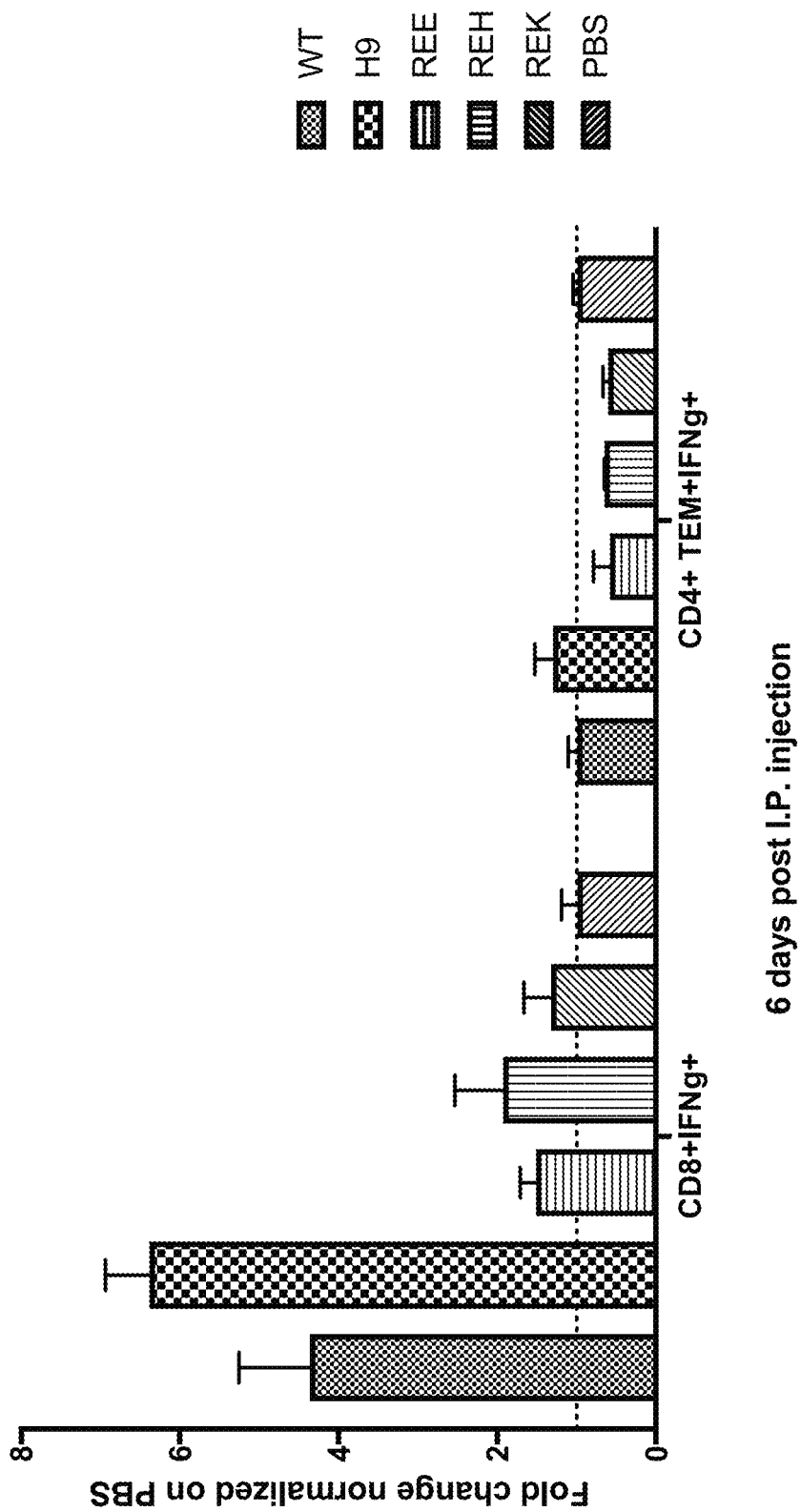

This Example shows in vivo administration of IL-2 variants in mice. On Day 0, female WT C57BL/6c mice received 30 µg of each MSA fused IL-2 variant by intraperitoneal (IP) injection. On Day 6, spleens were harvested and analyzed by flow cytometry for cell surface marker expression and intracellular cytokine (n=3/group) (see FIG. 5A). The graphs depicted in FIG. 5B, FIG. 5C and FIG. 5D represent the frequency of indicated cell subset for each condition normalized to the respective frequency in PBS-treated mice. B cells were defined by cells gated on CD3$^-$CD19$^+$. NK cells were gated on CD3$^-$ NK1.1$^+$. Cells gated on Ly6g (Gr1)$^+$ CD3$^+$CD11b$^+$ were defined as granulocytes.

As shown in FIG. 5B-5D, IL-2 variant administration resulted in mild change in other immune cell types, IL-2 H9_REH (REH; SEQ ID NO: 8) initiated a preferential expansion of CD4 effector memory T (TEM) cells. Notably, while WT (SEQ ID NO: 1) and H9 IL-2 (SEQ ID NO: 2) treatment resulted in a significant increase in IFNγ-secreting CD8 T cell frequency, this increase was not observed when mice were treated with either REE (SEQ ID NO: 6), REH (SEQ ID NO: 8) and REK (SEQ ID NO: 10).

Example 3

Figures 6A, 6B:
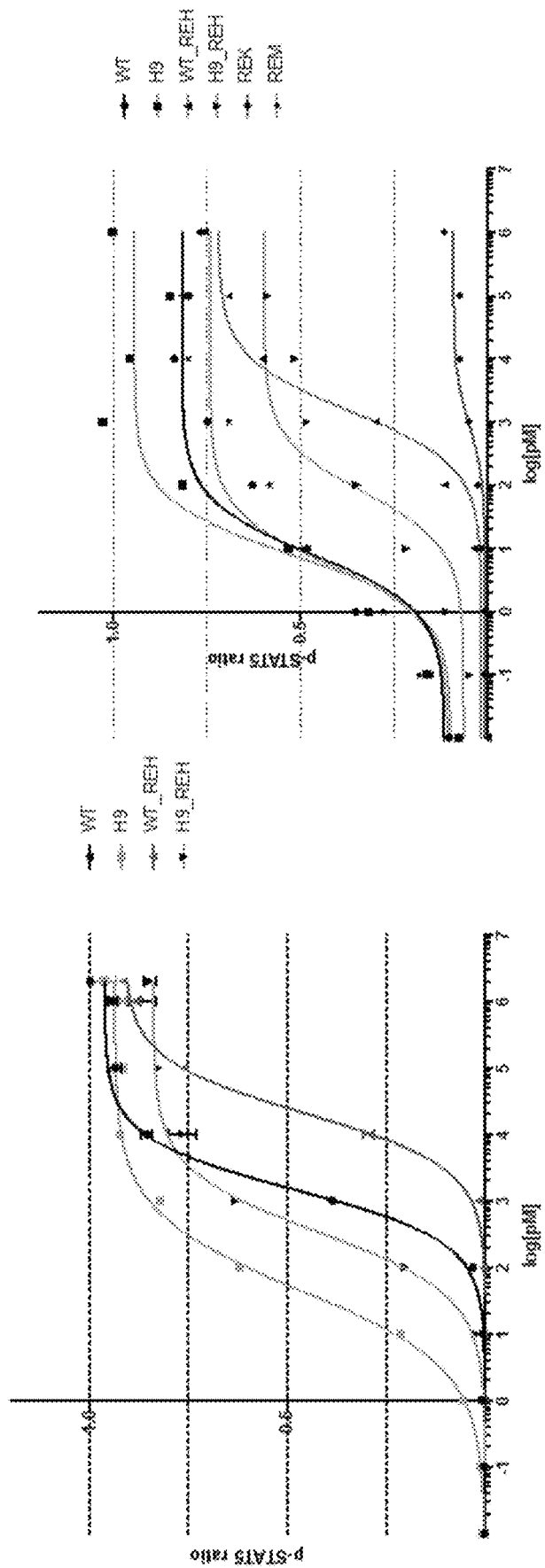
FIG. 6A-B depict the results of a phospho-STAT5 signaling assay with dose response of IL-2 variants.

This Example discloses the generation and characterization of IL-2 muteins on a wild-type background. The ability of these variants to stimulate the phosphorylation of STAT5 was measured using a Phospho-STAT5 signaling assay. Human NK-like YT cells (FIG. 6A) or mouse starved T cell blasts (FIG. 6B) were stimulated for 15 min with various human IL-2 variants fused to mouse serum albumin (MSA) at different concentrations as indicated on the graph (from 5 µM to 0 µM). All IL-2 variants were purified from insect cells. The Y axis of the graphs depicted in FIG. 6A and FIG. 6B shows the ratio of p-STAT5 signal from each IL-2 variant normalized to p-STAT5 signal from WT IL-2 for each concentration. As shown, the WT_REH (SEQ ID NO: 15) new partial agonist seems to exhibit a lower EC50 and higher $E_{max}$ compared to H9_REH (SEQ ID NO: 8). Both new partial agonists WT_REH (SEQ ID NO: 1). and H9_REH (SEQ ID NO: 8). show lower efficacies ($E_{max}$) than WT or H9 IL-2.

The wild-type background IL-2 muteins were then administered to a B16 melanoma mouse model. On D0, $10^6$ B16F10 cells were injected subcutaneously in C57BL/6 female mice. On D5, D9 and D14, mice were treated with 30 µg of each MSA-IL2 variants by IP injection. Tumor size were measured every other day from D5 using a caliper. Tumor volume in mm$^3$ was calculated as follows: (length*(width)$^2$)/2. On D19, spleens were harvested and analyzed by flow cytometry for cell surface and intracellular marker expression. (n=5/group).

Figure 7A:
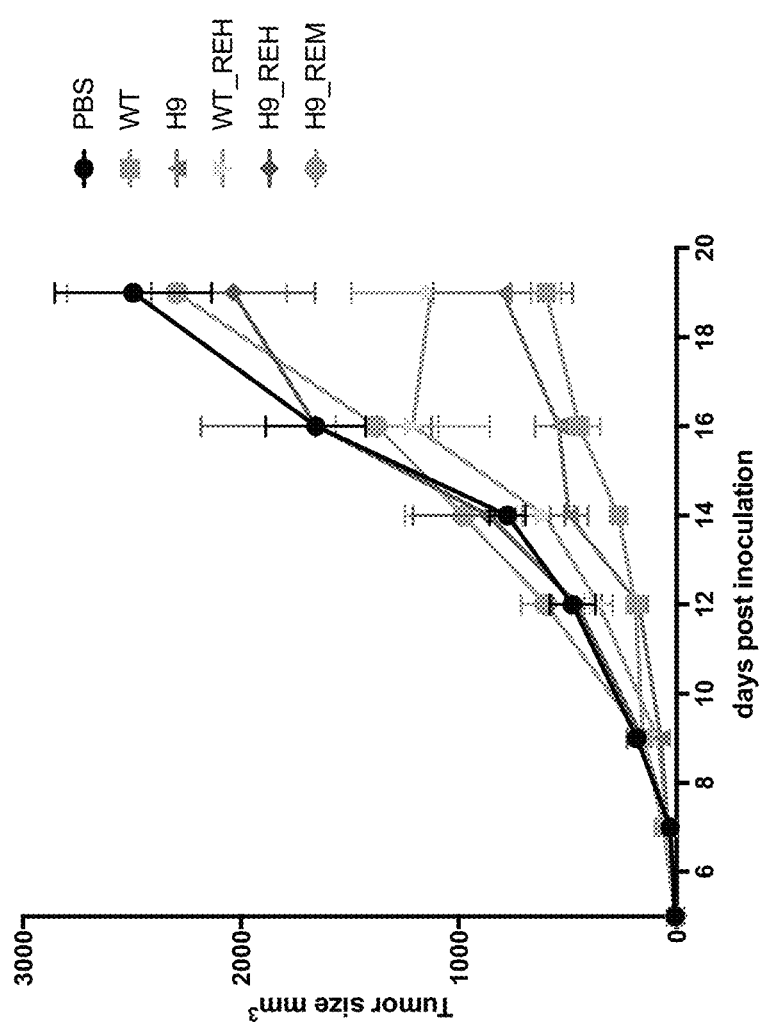
FIG. 7A-E depict the results of IL-2 variant administration on a B16 melanoma mouse model.
Figure 7B:
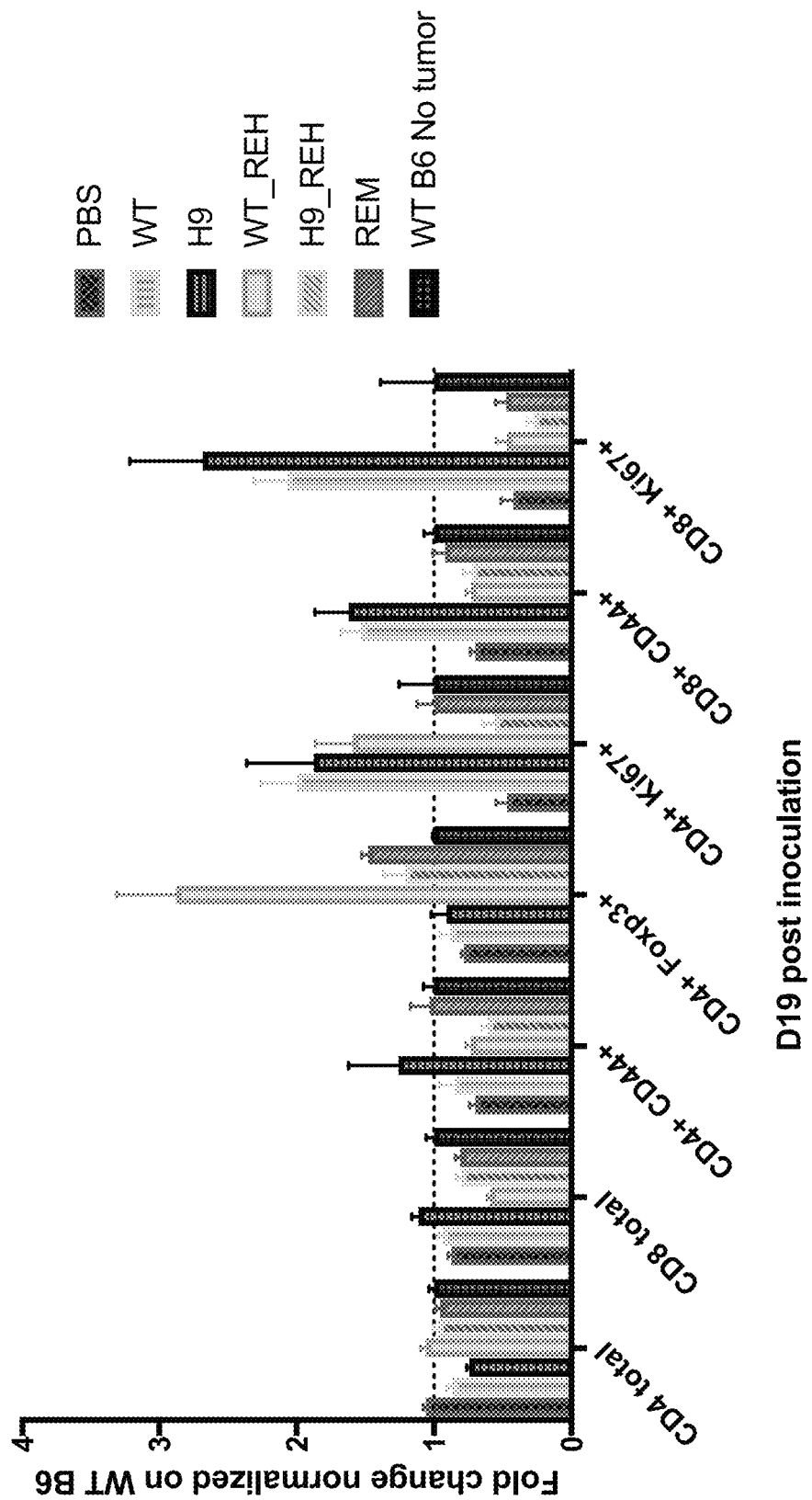
Figure 7C:
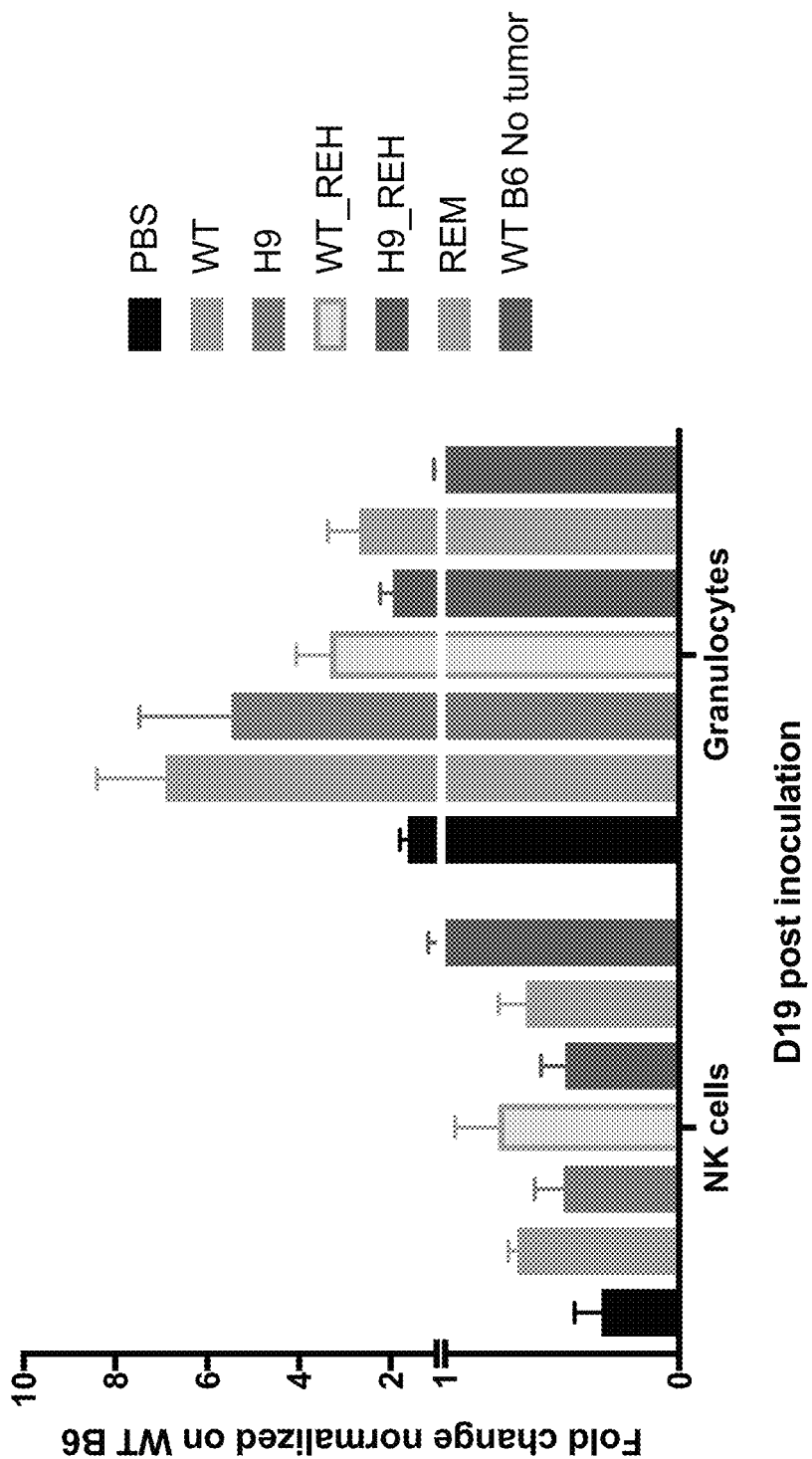
Figure 7D:
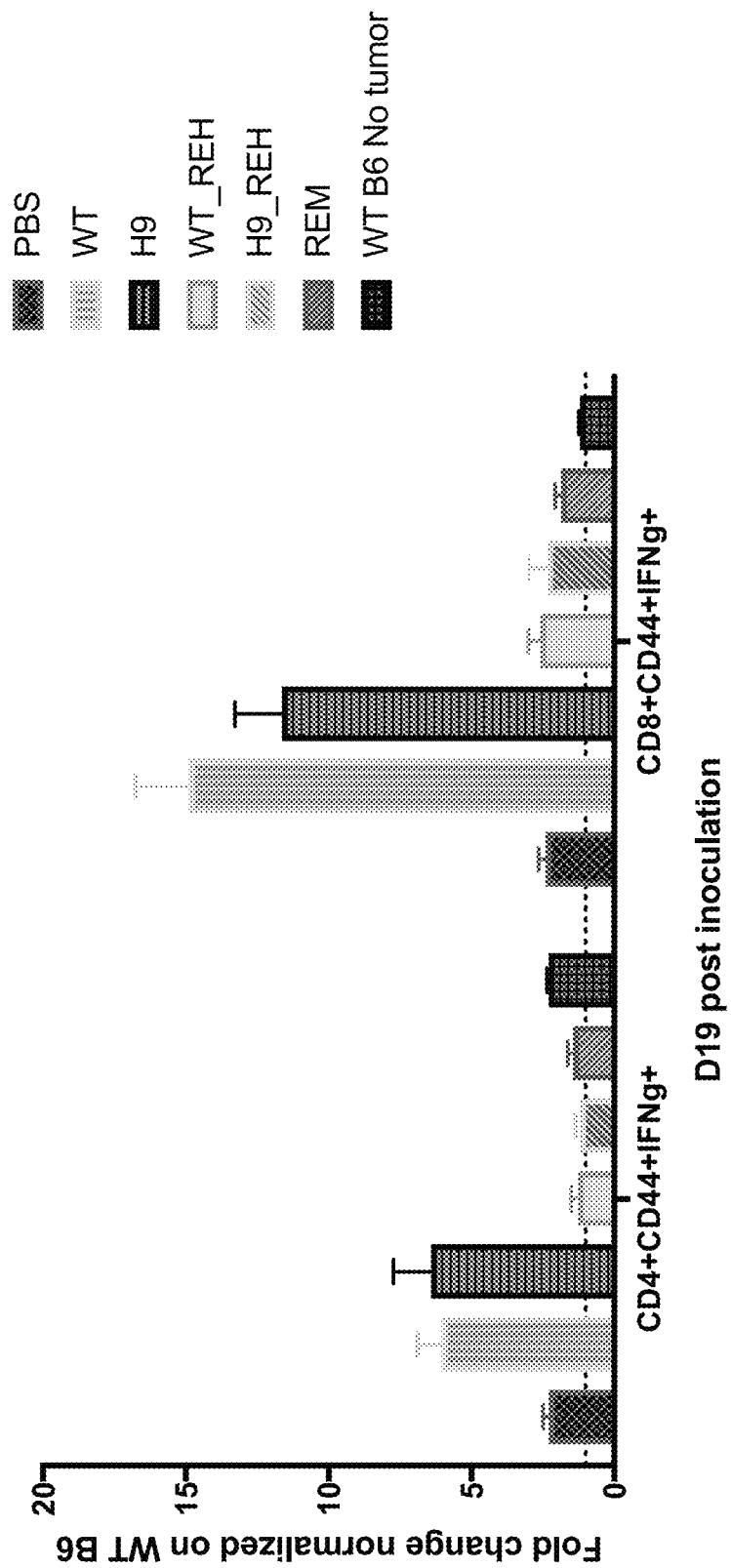
Figure 7E:
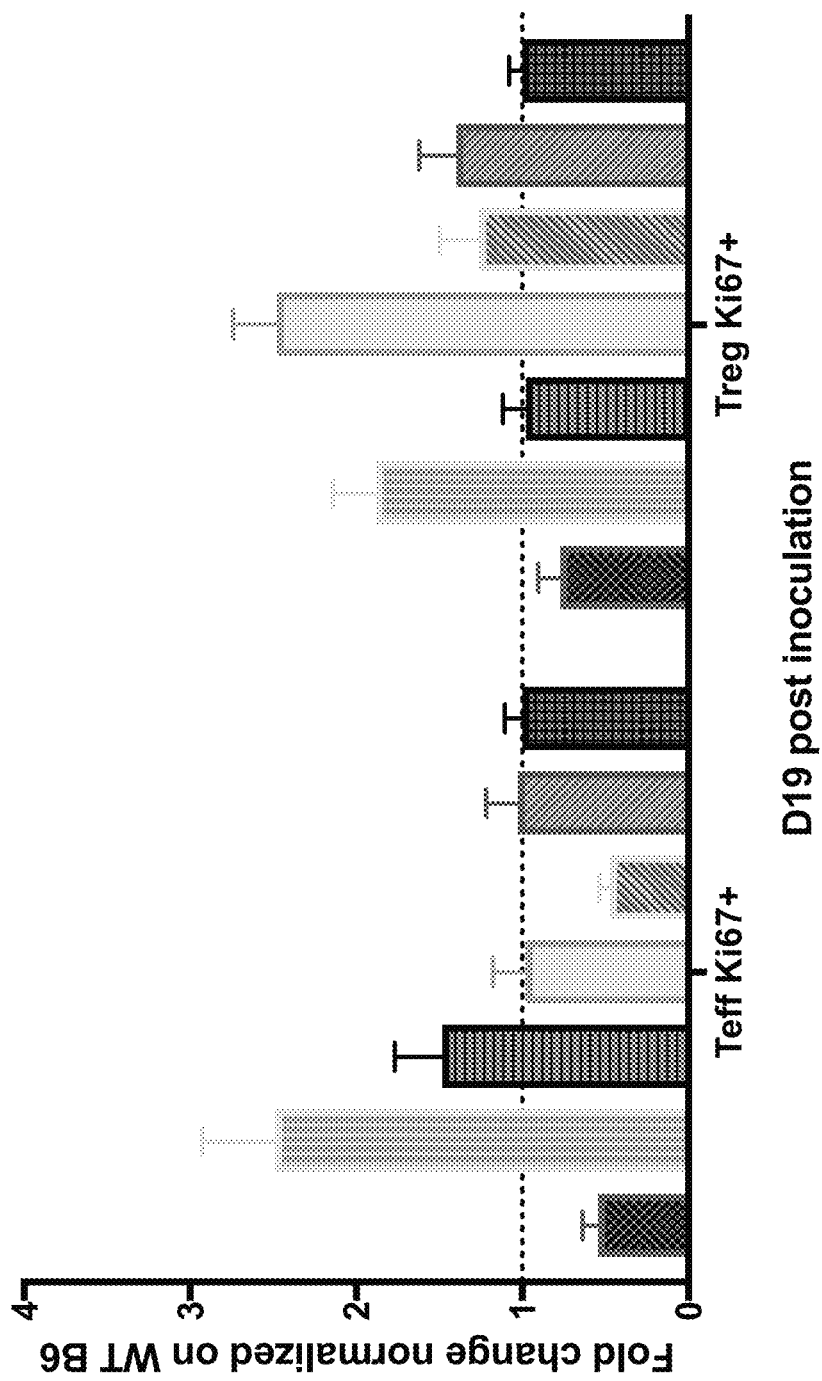

As depicted in FIG. 7A, tumor sizes were substantially smaller in mice treated with WT (SEQ ID NO: 1) or H9 (SEQ ID NO: 2) compared to PBS treated mice. H9_REH (SEQ ID NO: 8) and H9_REM (REM) (SEQ ID NO: 11) administration resulted in an increase of tumor size as comparable as PBS treated mice. Mice treated with WT_REH (SEQ ID NO: 15) exhibit larger tumor size compared to WT (SEQ ID NO: 1) or H9 (SEQ ID NO: 2) treated mice. An augmented frequency in Foxp3+ regulatory T ($T_{reg}$) cells was observed in REM (SEQ ID NO: 11) treated mice and a 3-fold increase in Foxp3+$T_{reg}$ cell number was observed when mice were treated with WT_REH (SEQ ID NO: 15) compared to PBS mice (FIG. 7B). WT and H9 treated mice exhibited an expansion of CD44 CD8 memory cells secreting IFNγ but not with new partial agonists WT_REH (SEQ ID NO: 15), H9_REH (SEQ ID NO: 8) or REM (SEQ ID NO: 11). FIG. 7C depicts the effect on NK cells and granulocytes. The same trend was observed with IFNγ secreting CD4 CD44+ memory T cells (FIG. 7D). Finally, while WT IL-2 (SEQ ID NO: 1) triggered the proliferation of CD4+ effector T cell (Teff Ki67+ cells) and $T_{reg}$ cells, WT_REH (SEQ ID NO: 1) induced a specific expansion of Treg cells but not of Teff cells FIG. 7E).

Example 4

This Example describes experiments performed to demonstrate that IL-2R partial agonists in the wild type background can elicit cell type specific responses in vivo.

In these experiments, female C57/BL6 mice were administered 3×30 µg intraperitoneal doses (Days 0, 3, and 6) of wild-type (WT) IL-2 (SEQ ID NO: 1), partial agonist WT_REH (SEQ ID NO: 15), partial agonist WT_RETR (SEQ ID NO: 21), partial agonist WT_REK (SEQ ID NO: 22), or PBS control. All cytokines were formatted as an N-terminal fusion to mouse serum albumin (MSA). On Day 7, spleen and peripheral lymph nodes were harvested and analyzed by flow cytometry and expressed as secreted proteins in insect cells.

The IL-2 muteins WT_RETR and WT_REK used in these experiments included the following amino acid sequences:

```
                              (WT_RETR; SEQ ID NO: 21)
APTSSSTKKTQLQLEHLRLDLEMILNGINNYKNPKLTRMLTFKFYMPKK

ATELKHLQCLEEELKPLEEVLNLAQSKNFHLRPRDLISNINVIVLELKG

SETTFMCEYADETATIVEFLNRWITFCTSIIRTLT.
```

```
                               (WT_REK; SEQ ID NO: 22)
APTSSSTKKTQLQLEHLRLDLEMILNGINNYKNPKLTRMLTFKFYMPKK

ATELKHLQCLEEELKPLEEVLNLAQSKNFHLRPRDLISNINVIVLELKG

SETTFMCEYADETATIVEFLNRWITFCKSIISTLT.
```

Figure 8B:
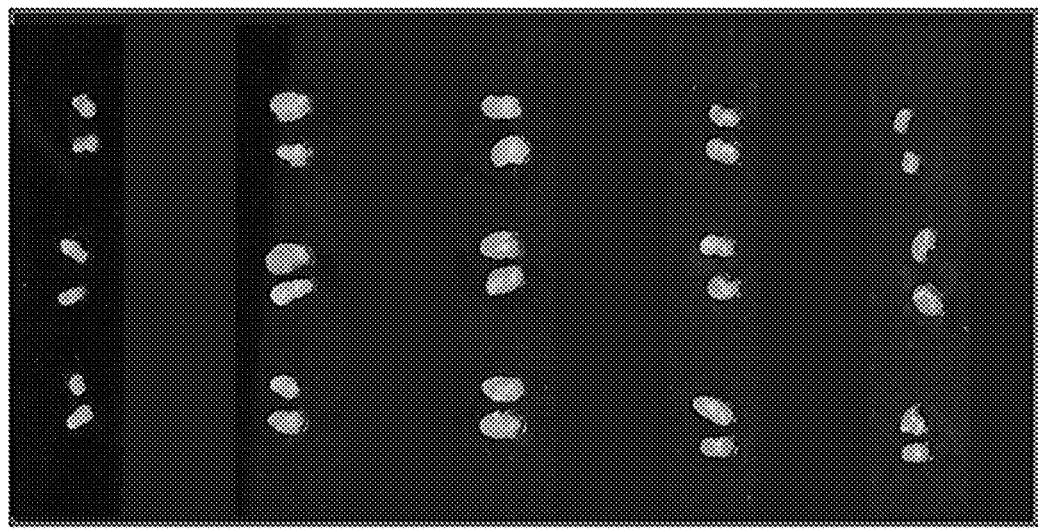
Figure 8A:
Figure 8C:
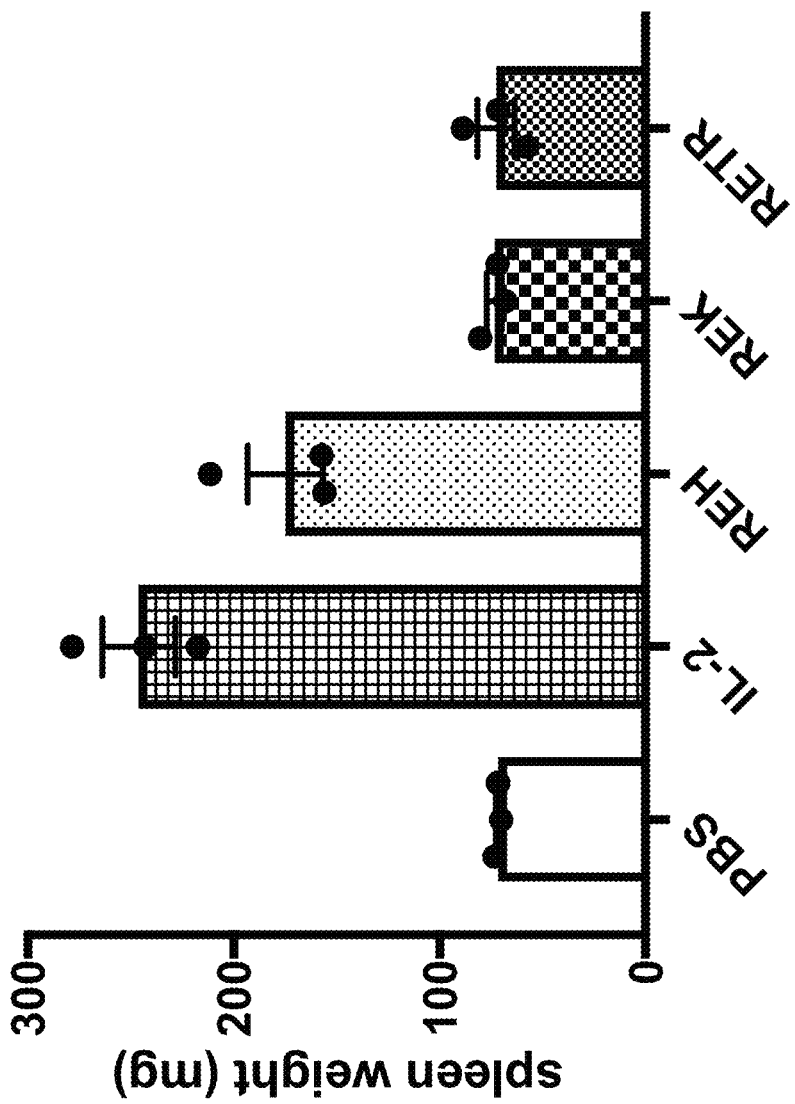
Figure 8G:
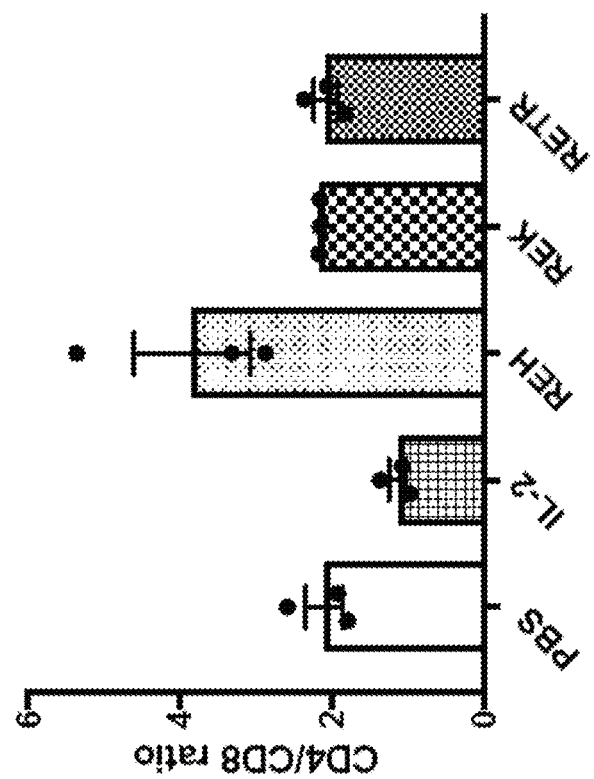
Figure 8F:
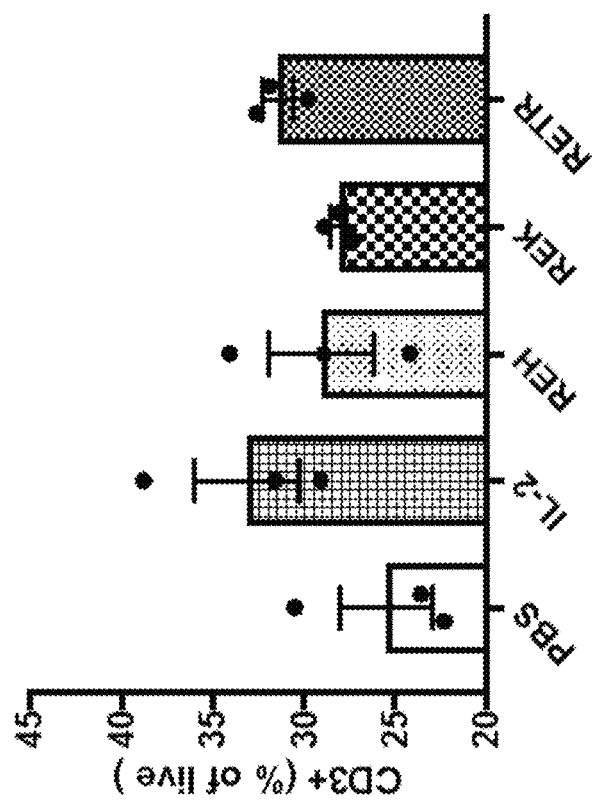
Figure 9A:
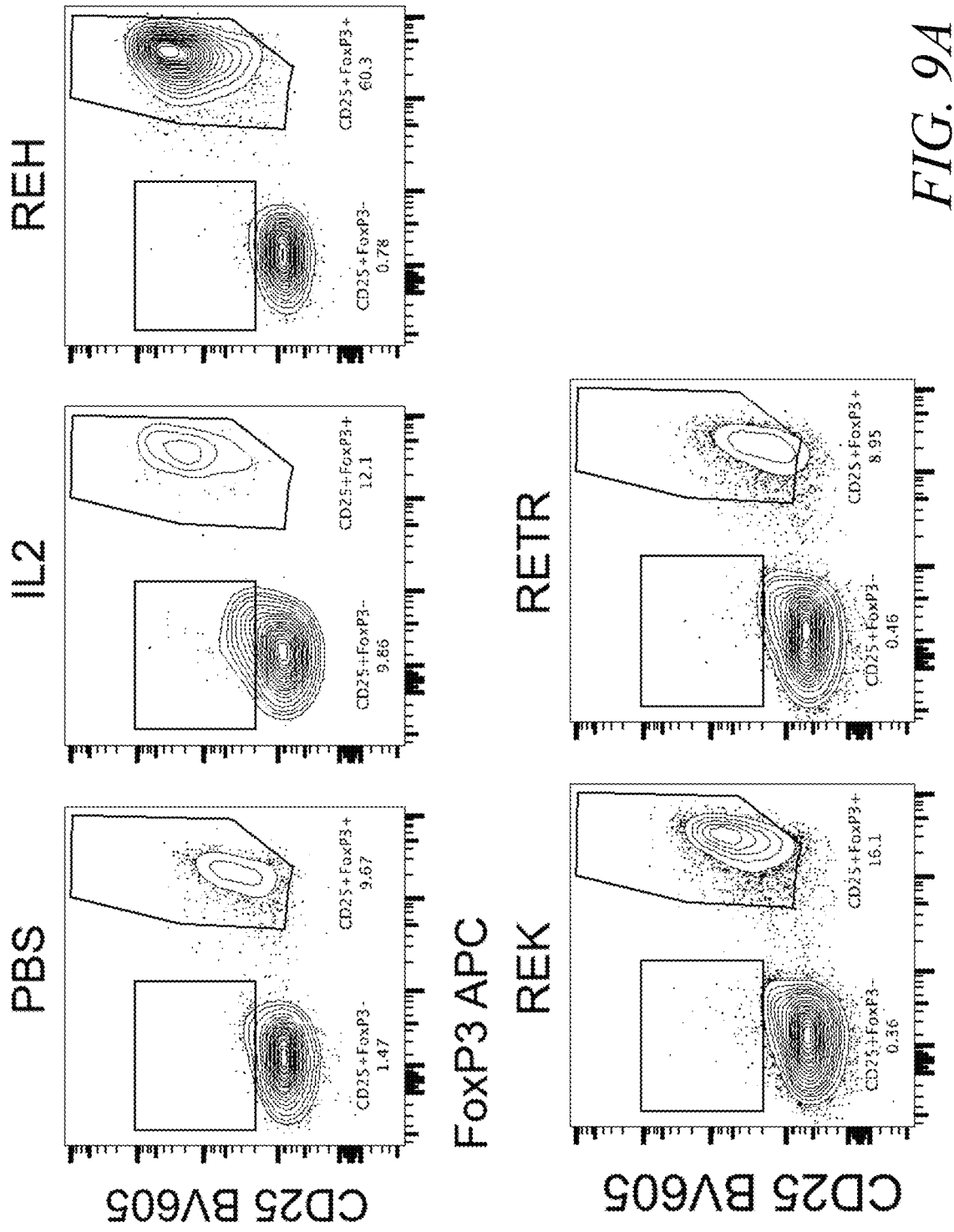
FIGS. 9A-9C graphically summarize experimental results from performed to illustrate that the IL-2R partial agonist REH increases the frequency of FoxP3$^+$ regulatory T cells.
Figure 9C:
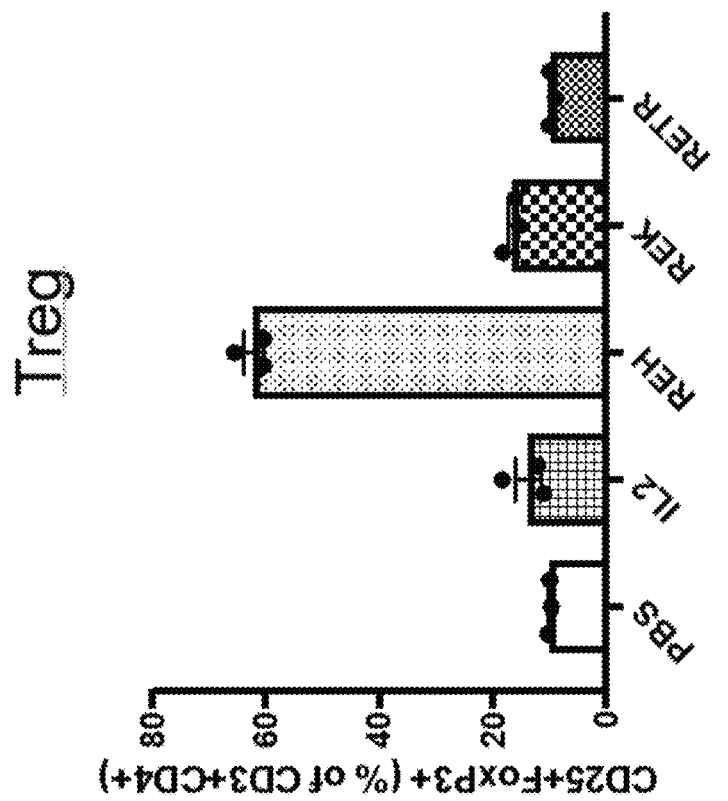
Figure 9B:
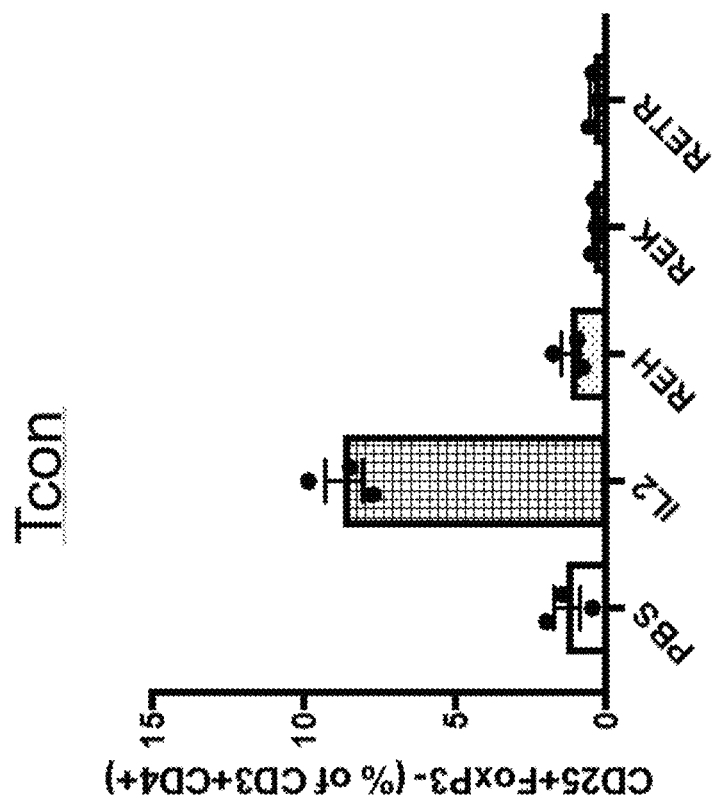
Figure 10:
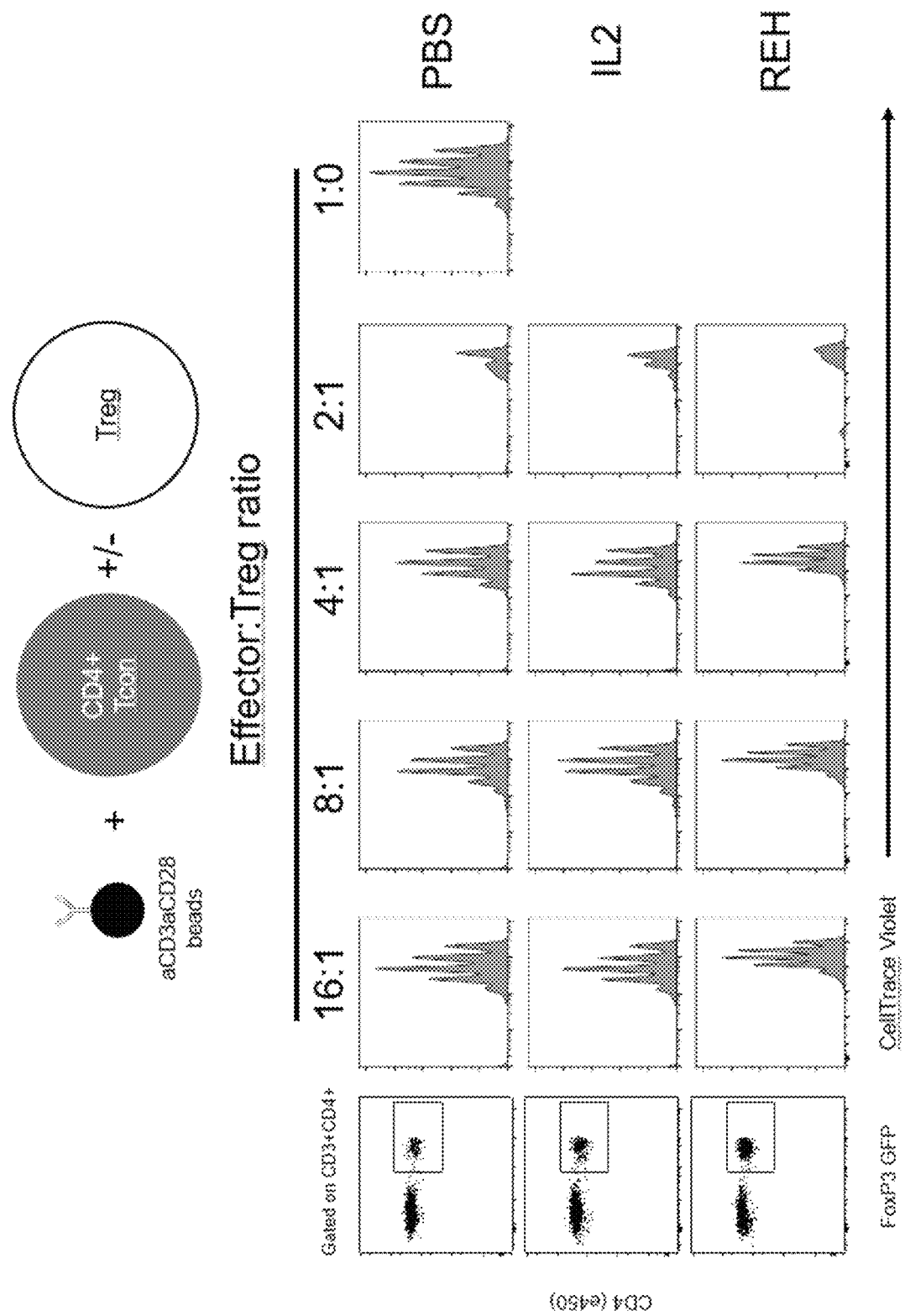
FIG. 10 is a graphical summary of the results from experiments performed to demonstrate that Tregs from mice treated with the IL-2R partial agonist REH suppress the proliferation of CD4+ conventional T cells.
Figure 11:
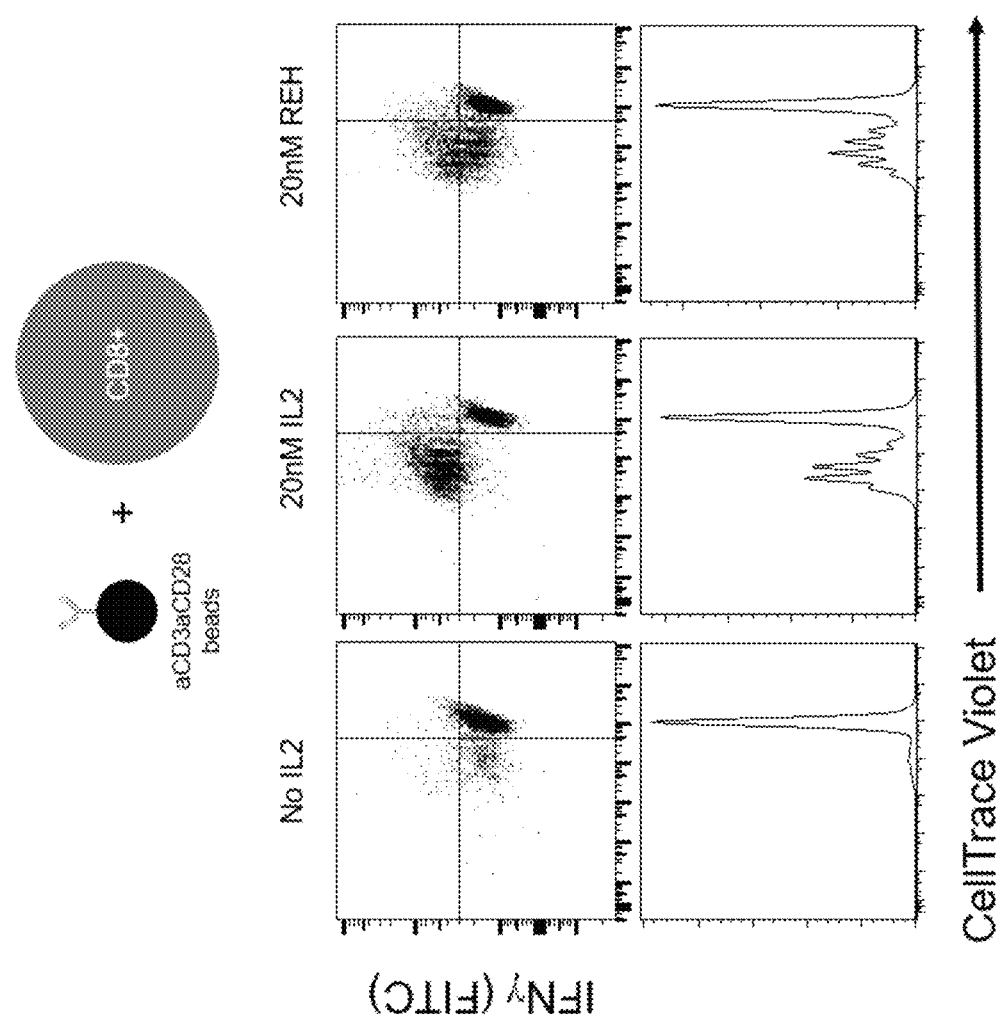
FIG. 11 is a graphical summary of the results from experiments performed to illustrate that the IL-2R partial agonist REH supports CD8$^+$ T cell proliferation but not IFNγ production.
Figure 12:
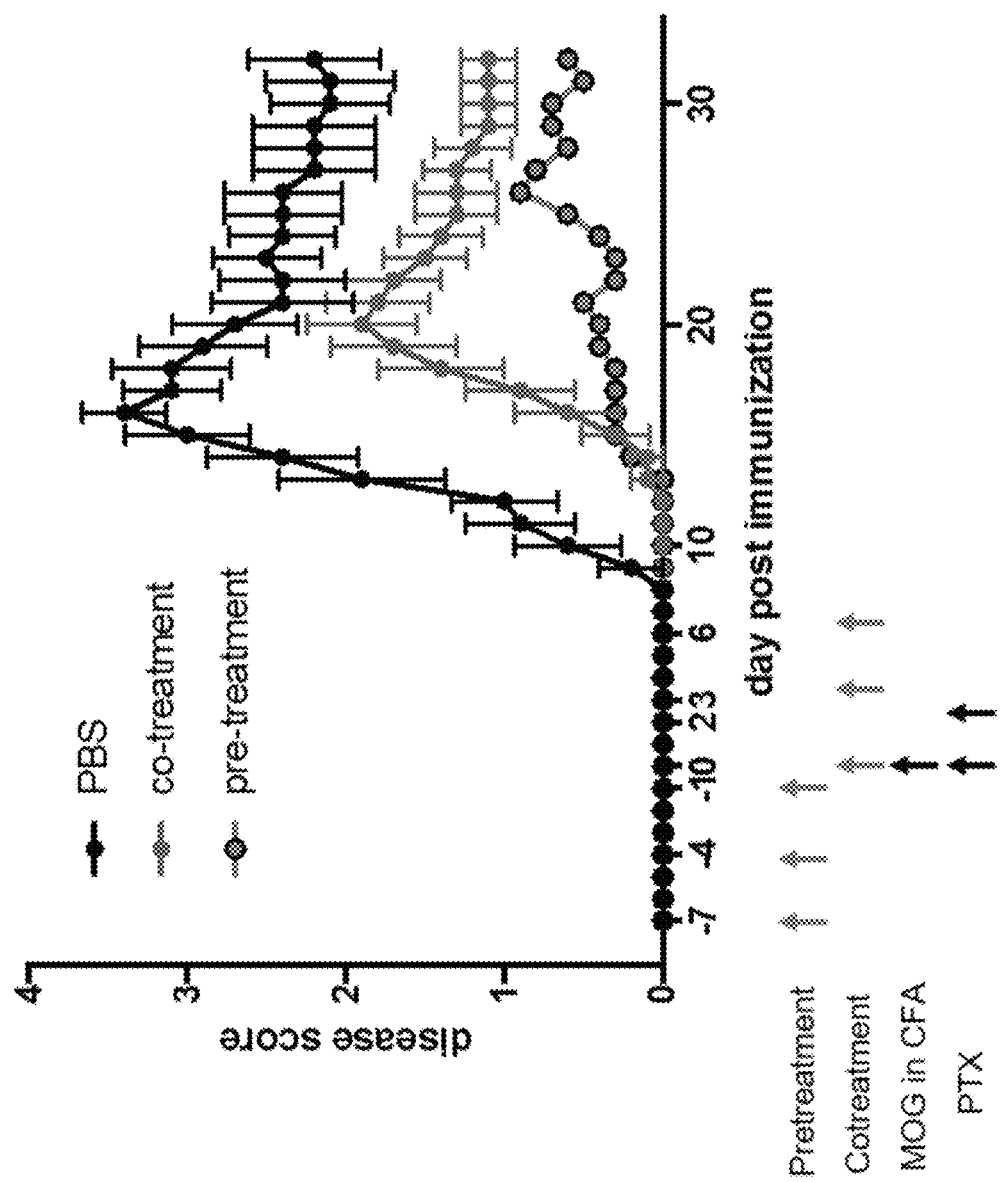
FIG. 12 is a graphical summary of the results from experiments performed to demonstrate that pre-treatment and co-treatment of the IL-2R partial agonist REH are protective of various autoimmune symptoms in rodent EAE model (an animal model of brain inflammation). Disease scores were as follows: 0—healthy; 1—limp tail; 2—partial hind limb paralysis; 3—complete hind limb paralysis; 4—whole body paralysis; 5—death.

It was observed that partial agonists of IL-2R induce enlargement of lymphoid organs was in accordance with their agonist activity (spleen and inguinal lymph nodes were photographed). As shown in FIGS. 8A-8B, administration of the partial agonists was found to induce an enlargement of lymphoid organs. IL-2 and partial agonists showed little effect on the frequency of NK cells (CD3-NK1.1+) while IL-2 but not the partial agonists showed a reduction in the frequency of B cells (CD3-CD19+). It was also observed that IL-2 and partial agonists did not alter the frequency of T cells (CD3+), however, IL-2 resulted in a decrease in the ratio of CD4 to CD8 T cells while one partial agonist, REH, caused an increase in the CD4 to CD8 T cell ratio.

Example 5

This Example describes experiments performed to demonstrate that treatment with an exemplary IL-2R partial agonist, REH, increased the frequency of FoxP3+ regulatory T cells with reduced activation of conventional CD4+ T cells.

In these experiments, female C57/BL6 mice were administered 3×30 µg intraperitoneal doses (Days 0, 3, and 6) of wild-type WT IL-2 (SEQ ID NO: 1), partial agonist WT_REH (SEQ ID NO: 15), partial agonist partial agonist WT_RETR (SEQ ID NO: 21), partial agonist WT_REK (SEQ ID NO: 22), or PBS control. All cytokines were formatted as an N-terminal fusion to mouse serum albumin (MSA) and expressed as secreted proteins in insect cells. On Day 7, spleen and peripheral lymph nodes were harvested and analyzed by flow cytometry to assess the frequency of Tregs (CD25+FoxP3+) and activation of conventional CD4+ T cells (CD25+FoxP3−).

It was observed that the IL-2R partial agonist REH increased the frequency of CD25$^+$FoxP3$^+$ regulatory T cells without inducing CD25$^+$ conventional cells.

Example 6

This Example describes experiments performed to demonstrate that Tregs from mice treated with the IL-2R partial agonist REH suppress the proliferation of CD4+ conventional T cells.

In these experiments, female B6.FoxP3 GFP mice were administered 3×30 µg intraperitoneal doses (Days 0, 3, and 6) of wild-type WT (SEQ ID NO: 1), partial agonist WT_REH (SEQ ID NO: 15) or PBS control. On Day 7, spleen and lymph nodes were harvested and CD4 T cells were isolated by magnetic sorting (MACS). Purified CD4+ T cells were sorted by fluorescent activated cell sorting (FACS) on the basis of GFP expression to isolate $T_{regs}$ (GFP+) and Tcons (GFP−). FoxP3 GFP+ cells from cytokine treated mice were co-cultured with CellTrace Violet labeled Tcons from PBS treated mice and aCD3aCD28 coated beads (1:1 bead to Tcon ratio). Proliferation of CTV loaded Tcons was assessed after 72 hours.

It was observed that FoxP3+ cells from REH treated mice were able to suppress proliferation of FoxP3− effector cells.

Example 7

This Example describes experiments performed to illustrate that the IL-2R partial agonist REH supports CD8+ T cell proliferation but not IFNγ production.

In these experiments, CD8+ T cells were isolated from spleen and lymph nodes of C57/BL6 mice by magnetic isolation (MACS), loaded with CellTrace Violet and co-cultured with aCD3aCD28 coated beads in the presence or absence of 20 nM WT (SEQ ID NO: 1) or WT_REH (SEQ ID NO: 15) for three days. Four hours prior to harvest, GolgiStop was added to the cells to prevent further cytokine secretion. At 72 hours, cells were fixed, permeabilized and stained with antibodies against interferon gamma (IFNγ).

It was observed that IL-2R partial agonist REH and IL-2 both could support proliferation but only IL-2 could induce robust IFNγ production by proliferating cells.

Example 8

This Example describes experiments performed to demonstrate that treatment and co-treatment of the IL-2R partial agonist REH are protective of various autoimmune symptoms in rodent EAE model (an animal model of brain inflammation).

In these experiments, B6 mice were pretreated (Day−7, −4, −1) or co-treated (Day 0, 3, and 7) with 10 μg of MSA fused WT_REH (SEQ ID NO: 15). On Day 0, mice were immunized with myelin oligodendrocyte glycoprotein (MOG 35-55) in complete Freund's adjuvant (CFA) and pertussis toxin (PTX) followed by a PTX boost on Day 2. Disease score progression was tracked by weight loss and disease score. Disease scores were as follows: 0—healthy; 1—limp tail; 2—partial hind limb paralysis; 3—complete hind limb paralysis; 4—whole body paralysis; 5—death.

It was observed that IL-2R partial agonist REH pretreatment was protective while REH co-treatment delays disease onset in a manner consistent with previous experiments examining the kinetics of Tregs in REH treated mice.

While particular alternatives of the present disclosure have been disclosed, it is to be understood that various modifications and combinations are possible and are contemplated within the true spirit and scope of the appended claims. There is no intention, therefore, of limitations to the exact abstract and disclosure herein presented.

What is claimed is:

1. A human interleukin 2 (hIL-2) mutein, wherein the hIL-2 mutein is a hIL-2 partial agonist and has an amino acid sequence identical to SEQ ID NO: 1, except for:
   (i) the L18R and Q22E substitutions;
   (ii) an amino acid substitution at position Q126 selected from the group consisting of Q126H and Q126K; and
   (iii) an N-terminal deletion of 0, 1, 2, or 3 amino acids.

2. The hIL-2 mutein of claim 1, wherein the amino acid substitution at position Q126 is Q126H.

3. The hIL-2 mutein of claim 1, wherein the amino acid substitution at position Q126 is Q126K.

4. The hIL-2 mutein of claim 3, wherein the hIL-2 mutein comprises a deletion of the alanine residue at position 1 of SEQ ID NO: 1.

5. The hIL-2 mutein of claim 4, wherein the hIL-2 mutein is N-terminally PEGylated with a branched PEG having an average molecular weight of about 40,000 daltons.

6. The hIL-2 mutein of claim 4, wherein the hIL-2 mutein is PEGylated at the N-terminal residue with a 40 kDa branched chain PEG molecule via a linker.

7. The hIL-2 mutein of claim 1, wherein the hIL-2 mutein comprises a deletion of the alanine residue at position 1 of SEQ ID NO: 1.

8. The hIL-2 mutein of claim 1, wherein the hIL-2 mutein is covalently linked to a molecule selected from the group consisting of (a) a human Fc antibody fragment, (b) human serum albumin, and (c) a polyethylene glycol (PEG) molecule.

9. The hIL-2 mutein of claim 8, wherein the molecule covalently linked to the hIL-2 mutein is a polyethylene glycol (PEG) molecule.

10. The hIL-2 mutein of claim 9, wherein the PEG comprises at least one linear or branched PEG having an average molecular weight of about 10,000 daltons to about 40,000 daltons.

11. The hIL-2 mutein of claim 10, wherein the PEG is a PEG having an average molecular weight of about 40,000 daltons.

12. The hIL-2 mutein of claim 9, wherein said the PEG is attached to the hIL-2 mutein via a linker.

13. The hIL-2 mutein of claim 9, wherein the PEG is attached to the N-terminus of the hIL-2 mutein.

14. The hIL-2 mutein of claim 9, wherein the PEG is a branched PEG.

15. The hIL-2 mutein of claim 9, wherein the hIL2 mutein is PEGylated at the N-terminal amino acid residue with a 40 kDa branched chain PEG molecule.

16. The hIL-2 mutein of claim 9, wherein the hIL2 mutein is PEGylated at the N-terminal amino acid residue with a 40 kDa branched chain PEG molecule via a linker.

17. A pharmaceutical composition comprising: (a) the hIL-2 mutein of claim 1; and (b) one or more pharmaceutically acceptable carriers.

18. The pharmaceutical composition of claim 17, wherein the amino acid substitution at position Q126 is Q126K and the N-terminal deletion is a deletion of 1 amino acid.

19. The pharmaceutical composition of claim 18, wherein the hIL-2 mutein is PEGylated at the N-terminal residue with a 40 kDa branched chain PEG molecule via a linker.

\* \* \* \* \*